United States Patent
Bosworth et al.

(10) Patent No.: US 12,350,277 B2
(45) Date of Patent: **\*Jul. 8, 2025**

(54) COMPOSITIONS AND METHODS OF USE FOR TREATING ABERRANT INFLAMMATION IN PERI-OCULAR SECRETORY GLANDS OR AT THE OCULAR SURFACE

(71) Applicant: CS Pharmaceuticals Limited, London (GB)

(72) Inventors: Charles F. Bosworth, Trabuco Canyon, CA (US); Achim H. Krauss, San Marcos, CA (US)

(73) Assignee: CS Pharmaceuticals Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/229,105

(22) Filed: Aug. 1, 2023

(65) Prior Publication Data

US 2023/0372360 A1  Nov. 23, 2023

Related U.S. Application Data

(63) Continuation of application No. 16/221,135, filed on Dec. 14, 2018, now Pat. No. 11,759,472, which is a continuation of application No. PCT/US2018/062298, filed on Nov. 21, 2018.

(60) Provisional application No. 62/589,493, filed on Nov. 21, 2017.

(51) Int. Cl.
| | |
|---|---|
| *A61P 27/02* | (2006.01) |
| *A61K 9/00* | (2006.01) |
| *A61K 9/06* | (2006.01) |
| *A61K 31/568* | (2006.01) |
| *A61K 31/573* | (2006.01) |
| *A61K 47/02* | (2006.01) |
| *A61K 47/06* | (2006.01) |
| *A61K 47/10* | (2017.01) |
| *A61K 47/12* | (2006.01) |
| *A61K 47/34* | (2017.01) |
| *A61K 47/18* | (2017.01) |

(52) U.S. Cl.
CPC .......... *A61K 31/573* (2013.01); *A61K 9/0014* (2013.01); *A61K 9/0048* (2013.01); *A61K 9/06* (2013.01); *A61K 31/568* (2013.01); *A61K 47/02* (2013.01); *A61K 47/06* (2013.01); *A61K 47/10* (2013.01); *A61K 47/12* (2013.01); *A61K 47/34* (2013.01); *A61P 27/02* (2018.01); *A61K 47/186* (2013.01)

(58) Field of Classification Search
CPC ........ A61K 9/0048; A61K 9/06; A61K 31/56; A61K 31/568; A61P 27/02
See application file for complete search history.

(56) References Cited

U.S. PATENT DOCUMENTS

| | | |
|---|---|---|
| 6,659,985 B2 | 12/2003 | Connor |
| 7,291,609 B2 | 11/2007 | Biggadike |
| 9,034,830 B2 | 5/2015 | Nanduri et al. |
| 9,463,201 B2 | 10/2016 | Alster et al. |
| 2003/0144635 A1 | 7/2003 | Connor |
| 2006/0247219 A1 | 11/2006 | Biggadike et al. |
| 2008/0312194 A1 | 12/2008 | Ousler, III et al. |
| 2010/0016264 A1 | 1/2010 | Connor et al. |
| 2015/0148711 A1 | 5/2015 | Bujak et al. |
| 2016/0092513 A1 | 3/2016 | Goodwin et al. |
| 2016/0243116 A1 | 8/2016 | Sandeep et al. |

FOREIGN PATENT DOCUMENTS

| | | |
|---|---|---|
| CN | 103429295 | 12/2013 |
| CN | 104125830 | 10/2014 |
| CN | 104224709 | 12/2014 |
| CN | 107427459 | 12/2017 |
| JP | 2010-520210 | 6/2010 |
| TW | 201637648 | 11/2016 |
| WO | WO-2008/106228 | 9/2008 |
| WO | WO-2016/092513 | 6/2016 |
| WO | WO-2017/196881 | 11/2017 |

OTHER PUBLICATIONS

Abelson et al., "Staying Local with Blepharitis Treatment: Ways to diagnose and categorize the disease, and thoughts on the best way to treat it when it occurs," Review of Ophthalmology (2012) 7 pages.

Asbell et al., "The International Workshop on Meibomian Gland Dysfunction: Report of the Clinical Trials Subcommittee," Investigative Opthalmology & Visual Science, Special Issue 2011, vol. 52, No. 4, 2065-2085.

Australian New Zealand Clinical Trials Registry, "Ocular safety and efficacy of a skin cream—Lauricidin®, updated from Effect of a wellness agent on signs and symptoms of dry eye" Trial ID ACTRN12616000011482. Date submitted on Dec. 16, 2015. Date last updated on Feb. 15, 2018. 12 pages.

(Continued)

*Primary Examiner* — Barbara P Badio
(74) *Attorney, Agent, or Firm* — MORRISON & FOERSTER LLP

(57) ABSTRACT

Provided herein are pharmaceutical compositions comprising a therapeutically effective amount of a lipophilic compound and a pharmaceutically acceptable carrier adapted for peri-ocular transdermal delivery of the lipophilic compound to one or more periorbital glands and/or the ocular surface tissues of a subject. Further provided herein are methods of using such pharmaceutical compositions for providing relief of one or more signs or symptoms of an ocular disease, methods of using one or more Meibomian glands (and meibum therein) as a drug delivery system for a lipophilic compound (e.g., a steroid) to the ocular surface, and kits related thereto.

24 Claims, 10 Drawing Sheets

(56) References Cited

OTHER PUBLICATIONS

Australian New Zealand Clinical Trials Registry, "Ocular safety and efficacy of a skin cream—Lauricidin®," Trial ID ACTRN12616000011482. Date submitted on Dec. 16, 2015. Date last updated on Feb. 15, 2018. 6 pages.
Avunduk et al., "The comparison of efficacies of topical corticosteroids and nonsteroidal anti-inflammatory drops on dry eye patients: A clinical and immunocytochemical study," Am J Ophthalmol. (2003) 136:593-602.
Cutolo et al., "The Use of Topical Corticosteroids for Treatment of Dry Eye Syndrome," Ocul. Immunol. Inlamm. (2019) 27(2):266-275.
Daull et al., "A preliminary evaluation of dexamethasone palmitate emulsion: a novel intravitreal sustained delivery of corticosteroid for treatment of macular edema," J. Ocul. Pharmacol. Ther. (2013) 29(2):258-269.
Dews, "2007 Report of the international dry eye workshop," Ocul Surf. (2007) 5(2):65-204.
Guan (ed.), Pharmaceutical Excipients and Packaging Materials, edition 1 (Jan. 31, 2017) pp. 112-113.
Jamal et al., "The role of difluprednate ophthalmic emulsion in clinical practice," Clin. Ophthalmol. (2009) 3:381-390.
Lee et al., "Ocular hypertensive response to topical dexamethasone ointment in children," Korean Journal of Ophthalmolgy (2006) 20(3):166-170.
Li et al. (eds.), Handbook of Common Pharmaceutical Excipients, edition 1 (Jun. 30, 2000) pp. 119-120.
Mah et al., "PERSIST: Physician's evaluation of Restasis(®) satisfaction in second trial of topical cyclosporine ophthalmic emulsion 0.05% for dry eye: a retrospective review," Clin Ophthalmol. 2012;6:1971-1976.
Notice on the First Office Action (translation) for CN 201880074872.9, issued Feb. 18, 2023, 16 pages.
Pan et al., "Application of Triamcinolone Acetonide in Orbital Diseases," Recent Advances in Ophthalmology (2007) 27(27):233-238.
Patel et al., "Preparation of ready to use ophthalmic gel for the treatment of ocular inflammation and infection based on QbD theory," Chinese Journal of Pharmaceuticals (2016) 47(7):939.
Raghava et al., "Periocular routes for retinal drug delivery," Expert Opin. Drug Deliv. (2004) 1(1):99-114.
Souza et al., "Topical delivery of ocular therapeutics: carrier systems and physical methods," J. Pharm. Pharmacol. (2014) 66(4):507-530.
Stamer et al., "Unique Response Profile of Trabecular Meshwork Cells to the Novel Selective Glucocorticoid Receptor Agonist, GW870086X," IOVS, 2013, vol. 54, No. 3, pp. 2100-2107.
Sun et al., "New dosage forms for ocular administration," Chinese Pharmaceutical Journal (2016) 51(23):1993-1998.
Tsubota et al., "New treatment of dry eye: the effect of calcium ointment through eyelid skin delivery," Br J Ophthalmol (1999) 83:767-770.
Uings et al., "Research Paper Discovery of GW870086: a potent anti-inflammatory steroid with a unique pharmacological profile," British Journal of Pharmacology (2013) 169(6):1389-1403.
Waite et al., "Posterior drug delivery via periocular route: challenges and opportunities," Ther. Deliv. (2017) 8(8):685-699.
Wilson et al., "Effect of dexamethasone on corneal endothelial function in Fuchs' dystrophy," Invest Ophthalmol Vis Sci. 1988;29(3):357-361.
Yang et al., "A clinical study of the efficacy of topical corticosteroids on dry eye," J Zhejiang Univ Sci B. (2006) 7(8):675-678.
Yang et al., "Preparation of Dexamethasone Ocular Implant," Chinese Journal of Pharmaceuticals (2008) 39(10):741-744.

COMPOSITIONS AND METHODS OF USE FOR TREATING ABERRANT INFLAMMATION IN PERI-OCULAR SECRETORY GLANDS OR AT THE OCULAR SURFACE

CROSS-REFERENCE TO RELATED APPLICATIONS

This application is a continuation of U.S. application Ser. No. 16/221,135, filed Dec. 14, 2018, which is a continuation of International Patent Application No. PCT/US2018/062298, filed Nov. 21, 2018, which claims priority from U.S. provisional application 62/589,493, filed Nov. 21, 2017, the contents of which are incorporated by reference in their entirety.

FIELD OF THE INVENTION

The present disclosure relates to pharmaceutical compositions adapted for peri-ocular transdermal delivery of one or more lipophilic compounds; to methods of use thereof; and to kits comprising such pharmaceutical compositions.

BACKGROUND

Topical drops have become the delivery method of choice for eye-care practitioners especially for diseases like dry eye, uveitis, bacterial conjunctivitis, and glaucoma because the ocular surface is seen as the primary target tissue for drug delivery. When a drop hits the eye, three parts of the anterior segment (i.e., cornea, conjunctiva, and sclera) act as routes for the drug's absorption with the cornea representing the primary route for ocular penetration. Drops are perceived as having significant advantages over other methods of delivery, including the minimization of adverse systemic effects as well as the avoidance of first-pass metabolism, which restricts the concentration of drug that ultimately reaches the target tissue (Abelson et al, 2012).

Topical eye drops, however, have several shortcomings: 1) They are difficult for patients to physically manage; 2) There are physical and physiological barriers that protect the eye and significantly diminish the amount of drug being delivered (e.g., low corneal permeability, blinking reflex, and tear turnover); and 3) Epithelial tight junctions prevent diffusion of larger molecules.

The lacrimal glands are paired, exocrine glands, one for each eye. They are located in the upper lateral region of each orbit, in the lacrimal fossa formed by the frontal bone. The lacrimal gland is the main contributor to the aqueous layer of the tear film. The meibomian glands are sebaceous glands in the eyelids inside the tarsal plate, responsible for the supply of meibum that prevents evaporation of the eye's tear film.

Disruption of the normal function of lacrimal and meibomian glands can result in aqueous deficient and/or evaporative forms of dry eye disease (DED), as well as a whole host of "plus" inflammatory eye diseases, such as exacerbated inflammatory ocular surface disease, phlyctenular keratitis, chalazion, and anterior blepharitis (See e.g., the Tear Film and Ocular Surface Society 2011 report on meibomian gland dysfunction (MGD); Nichols et al., 2011). Dry eye disease is a multifactorial disease of the ocular surface characterized by a loss of homeostasis of the tear film, and accompanied by ocular symptoms in which tear film instability and hyperosmolarity, ocular surface inflammation and damage, and neuronal sensory abnormalities play etiological roles (Craig et al., 2017). No matter what initiates a patient's DED (e.g., allergic eye disease, topical preservative toxicity, or xerophthalmia), patients eventually enter a chain of inflammatory events that perpetuate the disease. This inflammatory response can infiltrate the glands themselves. Indeed, tear dysfunction occurs when the lacrimal functional unit (LFU), composed of the tear secreting glands, the ocular surface, and the sensory and motor nerves which connect these tissues, is no longer able to maintain a stable precorneal tear layer (Beuerman et al., 1998; Stern et al., 1998a; Stern et al., 1998b). Disease or dysfunction of one or more components of the LFU may lead to an altered tear film. While the etiology of DED is multifactorial, significant evidence supports the hypothesis that the signs and symptoms are driven by inflammation of one or more components of the LFU.

Corticosteroid pharmacology targets inflammatory mediators underlying the signs and symptoms of DED. A number of studies and reports support the short-term use of topical corticosteroid eye drops in the treatment of patients with DED (Avunduk et al., 2003; DEWS, 2007; Pflugfelder et al., 1999; Yang et al., 2006). However, topical ocular corticosteroids administered as eye drops are generally recommended only for short-term use, as prolonged use may result in adverse ocular events, including elevated intraocular pressure (TOP), cataracts, and ocular infection (Becker, 1964; Bowling and Russell, 2011; Dinning, 1976).

While steroid ointments/creams are extensively prescribed to control long term or chronic non-ophthalmic inflammatory conditions (due to their low penetration/permeation), the long term use of current steroid ointment/cream formulations on or near the eyes is strongly disfavored, as ophthalmic use of these formulations is likely to induce serious adverse events, such as increased TOP (which may result in ocular hypertension or glaucoma, or induce loss of sight), posterior subcapsular cataracts, retardation of corneal epithelial healing, corticosteroid uveitis, mydriasis and ptosis, infection, and other possible side effects (e.g., transient ocular discomfort, steroid-induced calcium deposits, etc.). In fact, topical application of a typical dexamethasone ointment formulation to the eyelids of children was shown to sharply increase IOP. "Ocular hypertensive response after dexamethasone ointment to the eyelids occurred frequently in children, especially those 5 years old or younger" (See page 166 of Lee et al., Korean J Ophthalmol. 2006 Sep.; 20(3):166-70). Thus, steroid formulations/routes of administration appropriate for the long term or even chronic therapy of inflammatory conditions of the eye are lacking.

All references cited herein, including patent applications, patent publications, and non-patent literature are herein incorporated by reference in their entirety, as if each individual reference were specifically and individually indicated to be incorporated by reference.

BRIEF SUMMARY

To meet the above and other needs, disclosed herein are pharmaceutical compositions adapted for peri-ocular transdermal delivery of one or more lipophilic compounds. In some embodiments, the pharmaceutical compositions are adapted for peri-ocular transdermal delivery to significantly enhance the ocular safety of the delivered lipophilic compound by: 1) decreasing the concentration of the permeation enhancer in the pharmaceutical composition relative to the concentration used in a standard ointment/cream or ophthalmic formulation; 2) using a permeation enhancer (not typically found in topical steroid ointment/cream formulations) that is suitable for transdermal delivery of the compound into the eyelid (e.g., Tween-80); 3) formulating the pharmaceutical composition to achieve improved spreadability on the peri-ocular surface relative to an ointment base; 4) formulating the pharmaceutical composition to avoid flow from the pen-ocular surface onto the corneal surface; 5) using a novel steroid such as the compound of Formula I (which has been specifically developed with an ability to enable the glucocorticoid receptor to transrepress gene activation with less or little transactivation) in an effort to reduce the side effects of glucocorticoids that are thought to be mediated through transactivation; 6) using the Meibomian glands, meibum, and other fatty structures in the eyelids as a drug depot of a lipophilic compound for sustained delivery to the ocular surface; and/or 7) use of the Meibomian glands and meibum as a novel drug delivery system for a pharmaceutical formulation of a lipophilic compound applied peri-ocularly to the outside of the upper and/or lower eyelid(s). Accordingly, the present disclosure is directed, in part, to a safer method for treating ocular surface conditions as well as within the peri-ocular glands and lids by transdermally administering a pharmaceutical formulation (e.g., via topical application of the formulation to the outside of the upper and/or lower eyelids) as described herein in order to deliver a therapeutically active concentration of a lipophilic compound to the meibomian glands, the lacrimal glands, the accessory lacrimal glands, and the ocular surface. Without wishing to be bound by theory it is thought that lipophilic compounds (e.g., steroids) will preferentially accumulate in/partition to lipid-producing (e.g., meibum) pen-ocular glands (e.g., the Meibomian glands) and other fatty/lipophilic structures in the eyelids. Consequently, the present disclosure is believed to provide a novel therapeutic strategy for treating inflammation within the lacrimal functional unit (LFU), other ocular inflammatory diseases, bacterial infections of the eye, glaucoma, and ocular hypertension by delivering anti-glaucoma agents, antibiotics and other lipophilic compounds via transdermal pen-ocular delivery that diminishes or avoids some or all of the adverse events associated with the use of standard topical formulations in an ophthalmic setting, such as increased TOP, BAK sensitivity, and disruption of the pre-corneal tear film (e.g., blurred vision). In addition, the present disclosure is believed to provide a novel strategy for longer term/chronic ophthalmic therapy than may be used with current short-term topical ocular regimens (e.g., corticosteroids).

Accordingly, in one aspect, provided herein are pharmaceutical compositions comprising a therapeutically effective amount of a lipophilic compound, and a pharmaceutically acceptable carrier adapted for per-ocular transdermal delivery of the lipophilic compound to one or more peri-orbital (e.g., oil-secreting pen-orbital) glands of a subject. In one aspect, provided herein are pharmaceutical compositions comprising a therapeutically effective amount of a lipophilic compound, and a pharmaceutically acceptable carrier adapted for per-ocular transdermal delivery of the lipophilic compound to one or more pen-orbital (e.g., oil-secreting pen-orbital) glands of a subject, wherein the pharmaceutical composition is specifically formulated for pen-ocular delivery. In some embodiments, the lipophilic compound is not delivered systemically to the subject. In some embodiments, the lipophilic compound is not delivered to a tear or tear duct of the subject. In some embodiments, the lipophilic compound is not delivered by direct application to an ocular surface of the subject. In some embodiments, the pharmaceutical composition is not a liquid topical ocular suspension, emulsion, or solution. In some embodiments, the one or more peri-orbital glands are selected from the group consisting of a meibomian gland, a lacrimal gland, an accessory lacrimal gland, and any combinations thereof. In some embodiments, the lipophilic compound is delivered to an ocular surface of the subject via the meibomian gland and meibum. In some embodiments, the lipophilic compound is selected from the group consisting of steroids, antibiotics, immunomodulatory drugs, integrin antagonists, anti-inflammatory agents, and anti-glaucoma or ocular anti-hypertension agents.

In one aspect, provided herein are pharmaceutical compositions comprising a therapeutically effective amount of a steroid, and a pharmaceutically acceptable carrier adapted for per-ocular transdermal delivery of the steroid to one or more pen-orbital (e.g., oil-secreting pen-orbital) glands of a subject. In some embodiments, the pharmaceutical composition is specifically formulated for pen-ocular delivery. In some embodiments, the steroid is not delivered systemically to the subject. In some embodiments, the steroid is not delivered to a tear or tear duct of the subject. In some embodiments, the steroid is not delivered by direct application to an ocular surface of the subject. In some embodiments, the pharmaceutical composition is not a liquid topical ocular suspension, emulsion, or solution. In some embodiments, the one or more pen-orbital glands are selected from the group consisting of a meibomian gland, a lacrimal gland, an accessory lacrimal gland, and any combinations thereof. In some embodiments, the steroid is delivered to an ocular surface of the subject via the meibomian gland and meibum.

The steroid can be any steroid. In some embodiments that may be combined with any of the preceding embodiments, the steroid is selected from the compound of Formula I, fluocinolone, difluprednate, fluticasone, fluorometholone, loteprednol, dexamethasone, prednisolone, triamcinolone acetonide, rimexolone, cortisol, cortisone, hydrocortisone, testosterone, and ester derivatives thereof. In some embodiments, the steroid is selected from the compound of Formula I, difluprednate, loteprednol, dexamethasone, prednisolone, triamcinolone acetonide, and ester derivatives thereof. In some embodiments, the steroid is the compound of Formula I. In some embodiments, the pharmaceutical composition comprises the steroid at a concentration between 0.001% and 10% weight per weight (w/w). In some embodiments, the pharmaceutical composition comprises the steroid at a concentration between 0.01% and 2% w/w.

In one aspect, provided herein are pharmaceutical compositions comprising a therapeutically effective amount of an antibiotic, and a pharmaceutically acceptable carrier adapted for per-ocular transdermal delivery of the antibiotic to one or more pen-orbital (e.g., oil-secreting peri-orbital) glands of a subject. In one aspect, provided herein are pharmaceutical compositions comprising a therapeutically effective amount of an antibiotic, and a pharmaceutically acceptable carrier adapted for per-ocular transdermal delivery of the antibiotic to one or more pen-orbital (e.g., oil-secreting peri-orbital) glands of a subject, wherein the pharmaceutical composition is specifically formulated for pen-ocular delivery. In some embodiments, the antibiotic is not delivered systemically to the subject. In some embodiments, the antibiotic is not delivered to a tear or tear duct of the subject. In some embodiments, the antibiotic is not delivered by direct application to an ocular surface of the subject. In some embodiments, the pharmaceutical composition is not a liquid topical ocular suspension, emulsion, or solution. In some embodiments, the one or more pen-orbital glands are selected from the group consisting of a meibomian gland, a lacrimal gland, an accessory lacrimal gland, and any combinations thereof. In some embodiments, the antibiotic is delivered to an ocular surface of the subject via the meibomian gland and meibum.

The antibiotic can be any antibiotic. In some embodiments, the antibiotic is selected from the group consisting of sulfonamides, macrolides, chloramphenicol, aminoglycosides, fluoroquinolones, vancomycin, and tetracyclines. In some embodiments, the antibiotic is selected from the group consisting of azithromycin, erythromycin, gentamicin, natamycin, neomycin, tobramycin, vancomycin, bacitracin, besifloxacin, ciprofloxacin, gatifloxacin, levofloxacin, moxifloxacin, oxifloxacin, chloramphenicol, doxycycline, tetracyclin, gramicidin, mupirocin, polymyxin B, and sulfacetamide. In some embodiments, the pharmaceutical composition comprises the antibiotic at a concentration between 0.01% and 10% weight per weight (w/w). In some embodiments, the pharmaceutical composition comprises the antibiotic at a concentration between 0.1% and 2% w/w.

In one aspect, provided herein are pharmaceutical compositions comprising a therapeutically effective amount of an immunomodulatory drug, and a pharmaceutically acceptable carrier adapted for per-ocular transdermal delivery of the immunomodulatory drug to one or more pen-orbital (e.g., oil-secreting pen-orbital) glands of a subject. In one aspect, provided herein are pharmaceutical compositions comprising a therapeutically effective amount of an immunomodulatory drug, and a pharmaceutically acceptable carrier adapted for per-ocular transdermal delivery of the immunomodulatory drug to one or more pen-orbital (e.g., oil-secreting pen-orbital) glands of a subject, wherein the pharmaceutical composition is specifically formulated for pen-ocular delivery. In some embodiments, the immunomodulatory drug is not delivered systemically to the subject. In some embodiments, the immunomodulatory drug is not delivered to a tear or tear duct of the subject. In some embodiments, the immunomodulatory drug is not delivered by direct application to an ocular surface of the subject. In some embodiments, the pharmaceutical composition is not a liquid topical ocular suspension, emulsion, or solution. In some embodiments, the one or more peri-orbital glands are selected from the group consisting of a meibomian gland, a lacrimal gland, an accessory lacrimal gland, and any combinations thereof. In some embodiments, the immunomodulatory drug is delivered to an ocular surface of the subject via the meibomian gland and meibum.

The immunomodulatory drug can be any immunomodulatory drug. In some embodiments, the immunomodulatory drug is selected from the group consisting of calcineurin inhibitors and thalidomide analogues. In some embodiments, the immunomodulatory drug is selected from the group consisting of cyclosporine A, voclosporine, tacrolimus, pimecrolimus, thalidomide, lenalidomide, and pomalidomide. In some embodiments, the immunomodulatory drug is cyclosporine A. In some embodiments, the pharmaceutical composition comprises the immunomodulatory drug at a concentration between 0.01% and 10% weight per weight (w/w). In some embodiments, the pharmaceutical composition comprises the immunomodulatory drug at a concentration between 0.1% and 2% w/w.

In one aspect, provided herein are pharmaceutical compositions comprising a therapeutically effective amount of an integrin antagonist, and a pharmaceutically acceptable carrier adapted for per-ocular transdermal delivery of the integrin antagonist to one or more pen-orbital (e.g., oil-secreting pen-orbital) glands of a subject. In one aspect, provided herein are pharmaceutical compositions comprising a therapeutically effective amount of an integrin antagonist, and a pharmaceutically acceptable carrier adapted for per-ocular transdermal delivery of the integrin antagonist to one or more pen-orbital (e.g., oil-secreting pen-orbital) glands of a subject, wherein the pharmaceutical composition is specifically formulated for pen-ocular delivery. In some embodiments, the integrin antagonist is not delivered systemically to the subject. In some embodiments, the integrin antagonist is not delivered to a tear or tear duct of the subject. In some embodiments, the integrin antagonist is not delivered by direct application to an ocular surface of the subject. In some embodiments, the pharmaceutical composition is not a liquid topical ocular suspension, emulsion, or solution. In some embodiments, the one or more pen-orbital glands are selected from the group consisting of a meibomian gland, a lacrimal gland, an accessory lacrimal gland, and any combinations thereof. In some embodiments, the integrin antagonist is delivered to an ocular surface of the subject via the meibomian gland and meibum.

The integrin antagonist can be any integrin antagonist. In some embodiments, the integrin antagonist is selected from the group consisting of lifitegrast and GW559090, and ester derivatives thereof. In some embodiments, the pharmaceutical composition comprises the integrin antagonist at a concentration between 0.01% and 10% weight per weight (w/w). In some embodiments, the pharmaceutical composition comprises the integrin antagonist at a concentration between 0.1% and 5% w/w.

In one aspect, provided herein are pharmaceutical compositions comprising a therapeutically effective amount of an anti-inflammatory agent, and a pharmaceutically acceptable carrier adapted for per-ocular transdermal delivery of the anti-inflammatory agent to one or more pen-orbital (e.g., oil-secreting pen-orbital) glands of a subject. In one aspect, provided herein are pharmaceutical compositions comprising a therapeutically effective amount of an anti-inflammatory agent, and a pharmaceutically acceptable carrier adapted for per-ocular transdermal delivery of the anti-inflammatory agent to one or more pen-orbital (e.g., oil-secreting pen-orbital) glands of a subject, wherein the pharmaceutical composition is specifically formulated for pen-ocular delivery. In some embodiments, the anti-inflammatory agent is not delivered systemically to the subject. In some embodiments, the anti-inflammatory agent is not delivered to a tear or tear duct of the subject. In some embodiments, the anti-inflammatory agent is not delivered by direct application to an ocular surface of the subject. In some embodiments, the pharmaceutical composition is not a liquid topical ocular suspension, emulsion, or solution. In some embodiments, the one or more peri-orbital glands are selected from the group consisting of a meibomian gland, a lacrimal gland, an accessory lacrimal gland, and any combinations thereof. In some embodiments, the anti-inflammatory agent is delivered to an ocular surface of the subject via the meibomian gland and meibum.

The anti-inflammatory agent can be any anti-inflammatory agent. In some embodiments, the anti-inflammatory agent is selected from the group consisting of omega 3 fatty acids and non-steroidal anti-inflammatory drugs (NSAIDs). In some embodiments, the omega 3 fatty acids are selected from the group consisting of eicosapentaenoic acid (EPA), docosahexaenoic acid (DHA), alpha-linolenic acid (ALA), and any combinations thereof. In some embodiments, the NSAIDs are selected from the group consisting of bromfenac, diclofenac, indomethacin, flurbiprofen, ketorolac, nepafenac, and any combinations thereof. In some embodiments, the anti-inflammatory agent is selected from flurbiprofen and ketorolac. In some embodiments, the pharmaceutical composition comprises the anti-inflammatory agent at a concentration between 0.001% and 10% weight per weight (w/w). In some embodiments, the pharmaceutical composition comprises the anti-inflammatory agent at a concentration between 0.1% and 2% w/w.

In one aspect, provided herein are pharmaceutical compositions comprising a therapeutically effective amount of an anti-glaucoma or ocular anti-hypertension agent, and a pharmaceutically acceptable carrier adapted for per-ocular transdermal delivery of the anti-glaucoma or ocular anti-hypertension agent to one or more pen-orbital (e.g., oil-secreting pen-orbital) glands of a subject. In one aspect, provided herein are pharmaceutical compositions comprising a therapeutically effective amount of an anti-glaucoma or ocular anti-hypertension agent, and a pharmaceutically acceptable carrier adapted for per-ocular transdermal delivery of the anti-glaucoma or ocular anti-hypertension agent to one or more pen-orbital (e.g., oil-secreting pen-orbital) glands of a subject, wherein the pharmaceutical composition is specifically formulated for pen-ocular delivery. In some embodiments, the anti-glaucoma or ocular anti-hypertension agent is not delivered systemically to the subject. In some embodiments, the anti-glaucoma or ocular anti-hypertension agent is not delivered to a tear or tear duct of the subject. In some embodiments, the anti-glaucoma or ocular anti-hypertension agent is not delivered by direct application to an ocular surface of the subject. In some embodiments, the pharmaceutical composition is not a liquid topical ocular suspension, emulsion, or solution. In some embodiments, the one or more pen-orbital glands are selected from the group consisting of a meibomian gland, a lacrimal gland, an accessory lacrimal gland, and any combinations thereof. In some embodiments, the anti-glaucoma or ocular anti-hypertension agent is delivered to an ocular surface of the subject via the meibomian gland and meibum.

The anti-glaucoma or ocular anti-hypertension agent can be any anti-glaucoma agent or any ocular anti-hypertension agent. In some embodiments, the anti-glaucoma or ocular anti-hypertension agent is selected from the group consisting of bimatoprost, latanoprost, travoprost, tafluprost, latanoprostene-bunod, timolol, betaxolol, levobunolol, dorzolamide, brinzolamide, and acetazolamide. In some embodiments, the anti-glaucoma or ocular anti-hypertension agent is selected from bimatoprost, latanoprost, travoprost, tafluprost, latanoprostene-bunod, timolol, betaxolol, levobunolol, metipranolol, brimonidine, clonidine, apraclonidine, dorzolamide, brinzolamide, acetazolamide, methazolamide, netarsudil, and any combinations thereof. In some embodiments the anti-glaucoma drug is selected from bimatoprost, latanoprost, travoprost, brimonidine, brinzolamide, netarsudil and timolol. In some embodiments the anti-glaucoma agent is bimatoprost. In some embodiments, the pharmaceutical composition comprises the anti-glaucoma drug at a concentration between 0.0001% and 10% weight per weight (w/w). In some embodiments, the pharmaceutical composition comprises the anti-glaucoma drug or ocular anti-hypertension agent at a concentration between 0.01% and 2% w/w.

In some embodiments that may be combined with any of the preceding embodiments, the pharmaceutical composition further comprises a therapeutically effective amount of an additional steroid. In some embodiments, the additional steroid is selected from the compound of Formula I, fluocinolone, difluprednate, fluticasone, fluorometholone, loteprednol, dexamethasone, prednisolone, triamcinolone acetonide, rimexolone, cortisol, cortisone, hydrocortisone, testosterone, and ester derivatives thereof. In some embodiments, the lipophilic compound and the additional steroid are different.

In some embodiments that may be combined with any of the preceding embodiments, the pharmaceutical composition further comprises a therapeutically effective amount of one or more antibiotics. In some embodiments, the one or more antibiotics are selected from sulfonamides, macrolides, chloramphenicol, aminoglycosides, fluoroquinolones, vancomycin, tetracyclines, and any combinations thereof. In some embodiments, the one or more antibiotics are selected from azithromycin, erythromycin, gentamicin, natamycin, neomycin, tobramycin, vancomycin, bacitracin, besifloxacin, ciprofloxacin, gatifloxacin, levofloxacin, moxifloxacin, oxifloxacin, chloramphenicol, doxycycline, tetracyclin, gramicidin, mupirocin, polymyxin B, sulfacetamide, and any combinations thereof. In some embodiments, the one or more antibiotics are selected from azithromycin, gentamicin, tobramycin, bacitracin, besifloxacin, gatifloxacin, moxifloxacin, chloramphenicol, and doxycycline. In some embodiments, the pharmaceutical composition comprises the one or more antibiotics at a concentration between 0.01% and 10% weight per weight (w/w). In some embodiments, the pharmaceutical composition comprises the one or more antibiotics at a concentration between 0.1% and 2% w/w. In some embodiments, the lipophilic compound and the one or more antibiotics are different.

In some embodiments that may be combined with any of the preceding embodiments, the pharmaceutical composition further comprises a therapeutically effective amount of one or more immunomodulatory drugs. In some embodiments, the one or more immunomodulatory drugs are selected from calcineurin inhibitors, thalidomide analogues, and any combinations thereof. In some embodiments, the one or more immunomodulatory drugs are selected from cyclosporine A, voclosporine, tacrolimus, pimecrolimus, thalidomide, lenalidomide, pomalidomide, and any combinations thereof. In some embodiments, the immunomodulatory drug is cyclosporine A. In some embodiments, the pharmaceutical composition comprises the one or more immunomodulatory drugs at a concentration between 0.01% and 10% weight per weight (w/w). In some embodiments, the pharmaceutical composition comprises the one or more immunomodulatory drugs at a concentration between 0.1% and 2% w/w. In some embodiments, the lipophilic compound and the one or more immunomodulatory drugs are different.

In some embodiments that may be combined with any of the preceding embodiments, the pharmaceutical composition further comprises a therapeutically effective amount of one or more integrin antagonists. In some embodiments, the one or more integrin antagonists are selected from lifitegrast, GW559090, ester derivatives thereof, and any combinations thereof. In some embodiments, the integrin antagonist is GW559090. In some embodiments, the pharmaceutical composition comprises the one or more integrin antagonists at a concentration between 0.01% and 10% weight per weight (w/w). In some embodiments, the pharmaceutical composition comprises the one or more integrin antagonists at a concentration between 0.1% and 5% w/w. In some embodiments, the lipophilic compound and the one or more integrin antagonists are different.

In some embodiments that may be combined with any of the preceding embodiments, the pharmaceutical composition further comprises a therapeutically effective amount of one or more anti-inflammatory agents. In some embodiments, the one or more anti-inflammatory agents are selected from omega 3 fatty acids, non-steroidal anti-inflammatory drugs (NSAIDs), and any combinations thereof. In some embodiments, the omega 3 fatty acids are selected from eicosapentaenoic acid (EPA), docosahexaenoic acid (DHA), alpha-linolenic acid (ALA), and any combinations thereof. In some embodiments, the NSAIDs are selected from bromfenac, diclofenac, indomethacin, flurbiprofen, ketorolac, nepafenac, and any combinations thereof. In some embodiments, the one or more anti-inflammatory agents is selected from flurbiprofen and ketorolac. In some embodiments, the pharmaceutical composition comprises the one or more anti-inflammatory agents at a concentration between 0.001% and 10% weight per weight (w/w). In some embodiments, the pharmaceutical composition comprises the one or more anti-inflammatory agents at a concentration between 0.1% and 2% w/w. In some embodiments, the lipophilic compound and the one or more anti-inflammatory agents are different.

In some embodiments that may be combined with any of the preceding embodiments, the pharmaceutical composition further comprises a therapeutically effective amount of one or more anti-glaucoma drugs or ocular anti-hypertension agents. In some embodiments, the one or more anti-glaucoma drugs or ocular anti-hypertension agents are selected from bimatoprost, latanoprost, travoprost, tafluprost, latanoprostene-bunod, timolol, betaxolol, levobunolol, metipranolol, brimonidine, clonidine, apraclonidine, dorzolamide, brinzolamide, acetazolamide, methazolamide, netarsudil, and any combinations thereof. In some embodiments the anti-glaucoma drug or ocular anti-hypertension agent is selected from bimatoprost, latanoprost, travoprost, brimonidine, brinzolamide, netarsudil and timolol. In some embodiments the anti-glaucoma drug is bimatoprost. In some embodiments, the pharmaceutical composition comprises the one or more anti-glaucoma drugs or ocular anti-hypertension agents at a concentration between 0.0001% and 10% weight per weight (w/w). In some embodiments, the pharmaceutical composition comprises the one or more anti-glaucoma drugs or ocular anti-hypertension agents at a concentration between 0.01% and 2% w/w. In some embodiments, the lipophilic compound and the one or more anti-glaucoma drugs or ocular anti-hypertension agents are different.

In some embodiments that may be combined with any of the preceding embodiments, the pharmaceutically acceptable carrier is selected from an ointment, cream, lotion, gel, emulsion, suspension, oil, foam, transdermal patch, spray, and any combinations thereof. In some embodiments, the pharmaceutically acceptable carrier is an ointment. In some embodiments, the ointment comprises a paraffinic or a water-miscible ointment base. In some embodiments, the ointment comprises 61.5% w/w white soft paraffin, 8% w/w mineral oil, 8% w/w propylene glycol, 5% w/w of St. cyclomethicone-5NF, 5% w/w of labrasol, 5% w/w of propylene carbonate, 2.5% w/w of steareth 2, 2.5% w/w of St. emulsifier 10, and 2.5% w/w of St. elastomer-10. In some embodiments, the pharmaceutically acceptable carrier is a cream. In some embodiments, the cream comprises an oil-in-water base or a water-in-oil base. In some embodiments, the cream comprises 48% w/w soft paraffin, 8% w/w mineral oil, 8% w/w propylene glycol, 6.6% w/w ST-cyclomethicone-5NF, 3.3% w/w ST-emulsifier-10, 2% w/w ST-elastomer-10, 0.08% w/w methylparaben, 0.06% w/w dibasic sodium phosphate, 0.05% w/w citric acid, 0.02% w/w propylparaben, and q.s. purified water. In some embodiments, the cream comprises 48% w/w white petrolatum, 8% w/w mineral oil, 8% w/w propylene glycol, 6.6% w/w ST-cyclomethicone-SNF, 3.3% w/w emulsifier 10, 2% w/w ST-elastomer-10, 0.08% w/w methylparaben, 0.06% w/w sodium phosphate dibasic anhydrous, 0.05% w/w citric acid anhydrous, 0.02% w/w propylparaben, and q.s. purified water. In some embodiments, the cream comprises 48% w/w white petrolatum, 8% w/w mineral oil, 8% w/w propylene glycol, 6.6% w/w ST-cyclomethicone-SNF, 3.3% w/w emulsifier 10, 2% w/w ST-elastomer-10, 0.06% w/w sodium phosphate dibasic anhydrous, 0.05% w/w citric acid anhydrous, 0.02% w/w benzalkonium chloride, and q.s. purified water. In some embodiments, the cream is preservative-free comprising 48% w/w white petrolatum, 8% w/w mineral oil, 8% w/w propylene glycol, 6.6% w/w ST-cyclomethicone-SNF, 3.3% w/w emulsifier 10, 2% w/w ST-elastomer-10, 0.06% w/w sodium phosphate dibasic anhydrous, 0.05% w/w citric acid anhydrous, and q.s. purified water.

In some embodiments, one or more active pharmaceutical ingredients are incorporated at the desired final concentration (w/w) into a cream vehicle comprised of 48% w/w white petrolatum, 8% w/w mineral oil, 8% w/w propylene glycol, 6.6% w/w ST-cyclomethicone-SNF, 3.3% w/w emulsifier 10, 2% w/w ST-elastomer-10, 0.08% w/w methylparaben, 0.06% w/w sodium phosphate dibasic anhydrous, 0.05% w/w citric acid anhydrous, 0.02% w/w propylparaben, and q.s. purified water. In some embodiments, the cream vehicle comprises 48% w/w white petrolatum, 8% w/w mineral oil, 8% w/w propylene glycol, 6.6% w/w ST-cyclomethicone-SNF, 3.3% w/w emulsifier 10, 2% w/w ST-elastomer-10, 0.06% w/w sodium phosphate dibasic anhydrous, 0.05% w/w citric acid anhydrous, 0.02% w/w benzalkonium chloride, and q.s. purified water. In some embodiments, the cream vehicle is preservative-free comprising 48% w/w white petrolatum, 8% w/w mineral oil, 8% w/w propylene glycol, 6.6% w/w ST-cyclomethicone-SNF, 3.3% w/w emulsifier 10, 2% w/w ST-elastomer-10, 0.06% w/w sodium phosphate dibasic anhydrous, 0.05% w/w citric acid anhydrous, and q.s. purified water.

In some embodiments, one or more active pharmaceutical ingredients are incorporated at the desired final concentration by substituting an equal amount of white petrolatum or paraffin (w/w). As an example, one such embodiment comprises 46% w/w white petrolatum, 8% w/w mineral oil, 8% w/w propylene glycol, 6.6% w/w ST-cyclomethicone-SNF, 3.3% w/w emulsifier 10, 2% w/w ST-elastomer-10, 0.08% w/w methylparaben, 0.06% w/w sodium phosphate dibasic anhydrous, 0.05% w/w citric acid anhydrous, 0.02% w/w propylparaben, 2% w/w compound of Formula I and q.s. purified water. Another such embodiment is preservative-free and comprises 46% w/w white petrolatum, 8% w/w mineral oil, 8% w/w propylene glycol, 6.6% w/w ST-cyclomethicone-5NF, 3.3% w/w emulsifier 10, 2% w/w ST-elastomer-10, 0.06% w/w sodium phosphate dibasic anhydrous, 0.05% w/w citric acid anhydrous, 2% w/w compound of Formula I and q.s. purified water.

In some embodiments, the pharmaceutical composition comprises the lipophilic compound at a concentration between about 0.001% and about 10% weight per weight (w/w), between about 0.0001% and about 10% weight per weight (w/w), or between about 0.0001% and about 5% weight per weight (w/w). In some embodiments, the pharmaceutical composition comprises the lipophilic compound at a concentration between about 0.01% and about 2% w/w.

In some embodiments, the pharmaceutically acceptable carrier comprises benzalkonium chloride (BAK). In some embodiments, the pharmaceutically acceptable carrier comprises 48% w/w white petrolatum, 8% w/w mineral oil, 8% w/w propylene glycol, 6.6% w/w ST-cyclomethicone-SNF, 3.3% w/w emulsifier 10, 2% w/w ST-elastomer-10, 0.06% w/w sodium phosphate dibasic anhydrous, 0.05% w/w citric acid anhydrous, 0.02% w/w benzalkonium chloride, and purified water. In some embodiments, the pharmaceutically acceptable carrier is preservative-free. In some embodiments, the pharmaceutically acceptable carrier comprises white soft paraffin/petrolatum, mineral oil, propylene glycol, ST-cyclomethicone-SNF, ST-emulsifier-10, ST-elastomer-10, dibasic sodium phosphate, citric acid, and purified water. In some embodiments, the pharmaceutically acceptable carrier comprises 48% w/w white petrolatum, 8% w/w mineral oil, 8% w/w propylene glycol, 6.6% w/w ST-cyclomethicone-SNF, 3.3% w/w emulsifier 10, 2% w/w ST-elastomer-10, 0.06% w/w sodium phosphate dibasic anhydrous, 0.05% w/w citric acid anhydrous, and purified water.

In some embodiments that may be combined with any of the preceding embodiments, the subject is a human or a non-human animal. In some embodiments that may be combined with any of the preceding embodiments, the subject is suffering from, or is suspected and/or expected to be suffering from, inflammation of one or more peri-orbital glands. In some embodiments that may be combined with any of the preceding embodiments, the subject suffers from an ocular disease. In some embodiments, the ocular disease is selected from inflammation of the peri-ocular glands, meibomitis, dry eye disease, allergic eye disease, topical preservative toxicity, xerophthalmia, loss of homeostasis of the tear film, tear film instability and hyperosmolarity, ocular surface inflammation and damage, neuronal sensory abnormalities, meibomian gland dysfunction, exacerbated inflammatory ocular surface disease, phlyctenular keratitis, chalazion, anterior blepharitis, posterior blepharitis, bacterial infection, glaucoma, ocular hypertension, and any combinations thereof.

In another aspect, provided herein are methods of providing prophylactic palliative, or therapeutic relief of one or more signs or symptoms of an ocular disease in a subject comprising administering to the subject any of the pharmaceutical compositions described herein. In some embodiments, the subject is a human or a non-human animal. In some embodiments, the subject is suffering from, or is suspected and/or expected to be suffering from, inflammation of one or more peri-orbital glands. In some embodiments, the subject suffers from an ocular disease. In some embodiments, the ocular disease is selected from inflammation of the pen-ocular glands, meibomitis, dry eye disease, allergic eye disease, topical preservative toxicity, xerophthalmia, loss of homeostasis of the tear film, tear film instability and hyperosmolarity, ocular surface inflammation and damage, neuronal sensory abnormalities, meibomian gland dysfunction, exacerbated inflammatory ocular surface disease, phlyctenular keratitis, chalazion, anterior blepharitis, posterior blepharitis, bacterial infection, glaucoma, ocular hypertension, and any combinations thereof.

In some embodiments that may be combined with any of the preceding embodiments, the pharmaceutical composition is topically administered to an external portion of an eyelid of the subject, including the upper lateral region of an orbit of the subject. In some embodiments, the pharmaceutical composition is topically administered to the external portion of the upper and/or lower eyelid of the subject. In some embodiments, the lipophilic compound is delivered to an ocular surface of the subject via the meibomian gland. In some embodiments, the pharmaceutical composition is administered one, two, three, four, five, six or more times per day. In some embodiments, the pharmaceutical composition is administered for one day, two days, three days, four days, five days, six days, one week, two weeks, three weeks, four weeks, five weeks, six weeks, seven weeks, eight weeks, nine weeks, 10 weeks, 11 weeks, 12 weeks or more, 24 weeks, 36 weeks, 48 weeks or more. In some embodiments, prolonged administration of the pharmaceutical composition does not result in an adverse ocular event in the subject. In some embodiments, the adverse ocular event is selected from elevated intraocular pressure, cataracts, ocular infection, and any combinations thereof. In some embodiments, the lipophilic compound is not delivered systemically to the subject by the administration of the pharmaceutical composition. In some embodiments, the lipophilic compound is not delivered to a tear or tear duct of the subject by the administration of the pharmaceutical composition. In some embodiments, the lipophilic compound is not delivered directly to an ocular surface of the subject by the administration of the pharmaceutical composition.

In another aspect, provided herein are articles of manufacture or kits comprising any of the pharmaceutical compositions described herein. In some embodiments, the article of manufacture or kit further comprises a package insert comprising instructions for administering the pharmaceutical composition.

It is to be understood that one, some, or all of the properties of the various embodiments described above and herein may be combined to form other embodiments of the present disclosure. These and other aspects of the present disclosure will become apparent to one of skill in the art. These and other embodiments of the present disclosure are further described by the detailed description that follows.

BRIEF DESCRIPTION OF THE DRAWINGS

(FIG. 4A); b) white petrolatum at 37° C. (FIG. 4B); c) placebo cream at 25° C. (FIG. 4C); d) 2% triamcinolone acetonide (sample K) cream at 25° C. (FIG. 4D).

DETAILED DESCRIPTION

Figure 1:
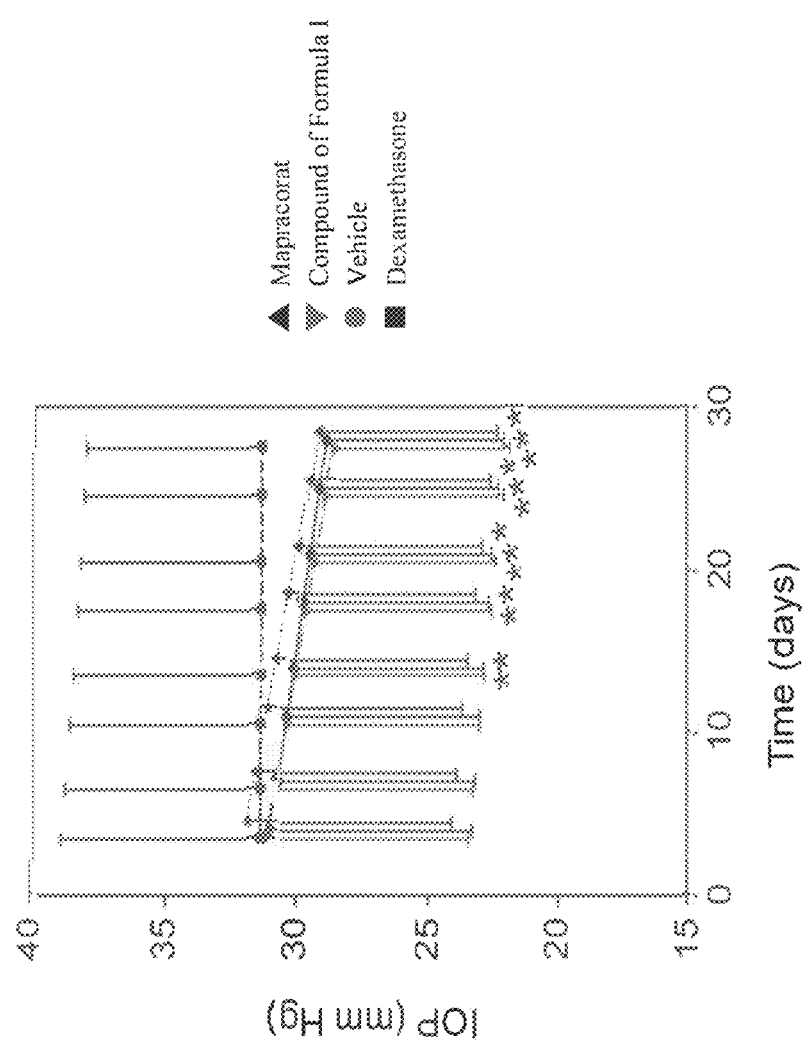
FIG. 1 shows the average diurnal intraocular pressure (IOP) during a 4-week treatment period with the indicated treatments administered topically to the eye. Analysis was conducted by a mixed effects model on the raw IOP data. Data are presented as the fitted TOP means±95% confidence limits; a * indicates a p<0.05, as compared to the dexamethasone-treated group.

Provided herein are pharmaceutical compositions comprising a therapeutically effective amount of a lipophilic compound, and a pharmaceutically acceptable carrier adapted for peri-ocular transdermal delivery of the lipophilic compound to one or more pen-orbital glands (e.g., the meibomian, lacrimal, and/or accessory lacrimal glands) of a subject. In some embodiments, the pharmaceutical composition is specifically formulated for pen-ocular delivery in accordance with the teachings herein. Also provided herein are methods of providing prophylactic, palliative, and/or therapeutic relief of one or more signs or symptoms of an ocular disease (e.g., an ocular inflammatory condition, bacterial infection, or glaucoma) comprising administering a therapeutically effective amount of any of the pharmaceutical compositions of the present disclosure to a subject in need thereof. Also provided herein are articles of manufacture or kits comprising one or more of the pharmaceutical compositions described herein.

Topical drops have become the delivery method of choice for eye-care practitioners especially for diseases like dry eye, uveitis, bacterial conjunctivitis, and glaucoma because the ocular surface is seen as the primary target tissue for drug delivery. However, the eye's rapid turnover of tears creates a significant problem for an ocular drop. The tear film is only about 7 µL in volume. An eye drop is about 30 to 50 µL, depending on the surface tension characteristics of the drug; therefore, only up to 1 to 3 percent of an active pharmaceutical ingredient (API) in a topical drop penetrates to the intended target tissues in the eye. The remainder of the drop drains from the tear film through the nasolacrimal system. Finally, the contact time of a drug with the ocular tissues is only around one minute due to the constant production of lacrimal fluid (0.5 to 2.2 µl/min.) and drainage (Abelson et al, 2012). Methods that increase a drug's retention time on the treated eye include high-viscosity solutions (e.g., Tobradex ST) and novel technologies such as mucous membrane penetrating technologies (e.g., Kala Pharmaceuticals, KPI-121), bioadhesive gels and fibrin sealant-based approaches (Gaudana R et al, 2010). Pen-ocular routes of delivery for ocular conditions include subconjunctival, subtenon, retrobulbar, and peribulbar administration (See FIG. 1 in Gaudana R et al, 2010).

Applying a drug directly to the eyelids has been envisioned as a route of drug delivery for lid conditions such as Meibomian Gland Dysfunction (MGD) and blepharitis. Meibomian gland dysfunction (MGD) is a chronic, diffuse abnormality of the meibomian glands (which reside in the eyelids), commonly characterized by terminal duct obstruction and/or qualitative/quantitative changes in the glandular secretion (Nichols et al, 2011). Blepharitis is inflammation of the eyelids. Local lid delivery has been envisioned for diseases impacting the lids because as Abelson and colleagues (2012) stated, "When you want to treat a local condition, the more local the delivery, the better the result will be. What better example of this need is there than the delivery of therapeutics for blepharitis directly to the affected lids?"

MacKeen et al (1995) reported on a unique drug delivery system that consists of applying petrolatum ointment vehicle to the lower eyelid. The ointment melts at skin temperature and gradually moves over the skin onto the ocular surface. The movement of the petrolatum ointment was termed supracutaneous. For this method to work, the musculature of the lower lid must move the drug toward and over the lid margin. Thus, this method of drug delivery envisions that the applied drug does not penetrate the skin of the lower lid, but instead travels on the surface of the skin around the eyelid where it physically mixes with the tear film (see also Tsubota et al, 1999).

The pharmaceutical compositions and methodologies of the present invention are based upon the unexpected finding that, when properly formulated in a suitable vehicle that, following topical pen-ocular application to one or both eyelids of an eye, does not melt and flow or move onto the ocular surface, but, instead, penetrates into the eyelid along with its API payload, lipophilic drugs delivered topically to the lids in such a manner can access the meibomian glands, meibum and other fatty structures within the eyelids which themselves can act as a drug depot resulting in sustained delivery to the ocular surface. Thus, "the more local the delivery, the better the result will be" is not an accurate way to conceive of delivering a lipophilic compound to the ocular surface. The current method of drug delivery also relies upon penetration of the eyelid skin, which is inconsistent with prior art that envisions the eyelid skin as a barrier to successful ocular surface drug delivery.

Commonly used lipophilic, topical, ocular therapeutics that could benefit from this new delivery method include treatments for inflammatory eye diseases, which include dry eye disease (e.g., RESTASIS® and corticosteroids), glaucoma (e.g., latanoprost), and bacterial conjunctivitis (e.g., AzaSite).

Pflugfelder and colleagues (2004) demonstrated that a topical corticosteroid may achieve the objective of a short-term treatment of acute exacerbations of DED signs or symptoms. They evaluated loteprednol etabonate ophthalmic suspension (0.5%) dosed 4 times daily versus placebo for the treatment of DED in patients with delayed tear clearance. In patients with at least moderate clinical inflammation, significant differences in clinical signs (nasal and tarsal hyperemia) between groups were observed as early as week 2 and persisted through week 4 of the study. In addition, the improvement in the redness visual analog scale (VAS) score was consistently 20% better in the loteprednol-treated patients compared with the vehicle-treated patients.

Capitalizing on the known safety profile of loteprednol etabonate, Kala Pharmaceuticals, Inc is developing KPI-121 as a novel nanoparticle formulation of loteprednol etabonate using mucus-penetrating particle (MPP) technology. In October of 2017, Kala filed an IND for KPI-121 1% as a treatment for inflammation and pain following ocular surgery. In January of 2018, they announced top line results for KPI-121 0.25% for the temporary relief of the signs and symptoms of DED. Their two Phase 3 DED studies (STRIDE 1 and STRIDE 2) demonstrated that KPI-121 0.25% dosed four-times-daily (QID) could provide statistically significant reductions in conjunctival hyperemia and marginal reductions in ocular discomfort severity at Day 15. Their topical ocular route of delivery results in several significant challenges for the introduction of a successful treatment: 1) QID dosing is inconvenient for patients and likely to result in poor compliance; 2) the need for frequent administration to maintain therapeutically active drug levels for anti-inflammatory efficacy; 3) potential safety concerns related to frequent administration; and 4) the need for a vehicle that can itself alter the functional characteristics of a normal tear film.

In addition to seeking sustained release formulations for inflammatory eye conditions to improve patient adherence by reducing dosing frequency and increasing efficacy by establishing more sustained suppression of inflammation, sustained release formulations are being developed in glaucoma to additionally remove preservatives such as benzalkonium chloride (BAK) and for bacterial conjunctivitis to prevent periods of regrowth. Thus, there is a need across ophthalmic conditions for a sustained release formulation that is less invasive, reduces dosing frequency, maintains constant therapeutic exposures at the site of action, minimizes disruption of the pre-corneal tear film, and reduces ocular exposure to formulation excipients.

I. Pharmaceutical Compositions

Certain aspects of the present disclosure relate to a pharmaceutical composition comprising a therapeutically effective amount of a lipophilic compound, and a pharmaceutically acceptable carrier adapted for peri-ocular transdermal delivery of the lipophilic compound to one or more peri-orbital glands (e.g., the meibomian, lacrimal, and/or accessory lacrimal glands) of a subject. The term "peri-ocular" refers to the area surrounding the eyeball but within the orbit, including eyelids and lateral regions of the orbit. The peri-orbital glands are the glands in the area around the eyeball including, for example, the meibomian, lacrimal, and/or accessory lacrimal glands. In some embodiments, the pharmaceutical composition is specifically formulated for peri-ocular delivery. In some embodiments, the pharmaceutically acceptable carrier is adapted for peri-ocular transdermal delivery by: 1) decreasing the concentration of the permeation enhancer in the carrier relative to the concentration used in a standard ointment/cream or ophthalmic formulation; 2) using a permeation enhancer (not typically found in topical steroid ointment/cream formulations) that is suitable for transdermal delivery of the compound into the eyelid (e.g., Tween-80); 3) formulating the pharmaceutical composition to achieve improved spreadability on the peri-ocular surface relative to an ointment base; and/or 4) formulating the pharmaceutical composition to avoid flow from the peri-ocular surface onto the corneal surface. In some embodiments, the pharmaceutical compositions are adapted for peri-ocular transdermal delivery to significantly enhance the ocular safety of the delivered lipophilic compound by: 1) decreasing the concentration of the permeation enhancer in the pharmaceutical composition relative to the concentration used in a standard ointment/cream or ophthalmic formulation; 2) using a permeation enhancer (not typically found in topical steroid ointment/cream formulations) that is suitable for transdermal delivery of the compound into the eyelid (e.g., Tween-80); 3) formulating the pharmaceutical composition to achieve improved spreadability on the peri-ocular surface relative to an ointment base; 4) formulating the pharmaceutical composition to avoid flow from the peri-ocular surface onto the corneal surface; 5) using a novel steroid such as the compound of Formula I (which has been specifically developed with an ability to enable the glucocorticoid receptor to transrepress gene activation with less or little transactivation) in an effort to reduce the side effects of glucocorticoids that are thought to be mediated through transactivation; 6) using the Meibomian glands, meibum, and other fatty structures in the eyelids as a drug depot of a lipophilic compound for sustained delivery to the ocular surface; and/or 7) use of the Meibomian glands and meibum as a novel drug delivery system for a pharmaceutical formulation of a lipophilic compound applied peri-ocularly to the outside of the upper and/or lower eyelid(s).

In some embodiments, the pharmaceutical composition further comprises a therapeutically effective amount of at least one additional steroid, antibiotic, immunomodulatory drug, integrin antagonist, anti-inflammatory agent, and/or anti-glaucoma or ocular anti-hypertension agent, in any combination. In some embodiments comprising a lipophilic compound and further comprising at least one additional steroid, antibiotic, immunomodulatory drug, integrin antagonist, anti-inflammatory agent, and/or anti-glaucoma or ocular anti-hypertension agent, the lipophilic compound is different from the at least one additional steroid, antibiotic, immunomodulatory drug, integrin antagonist, anti-inflammatory agent, and/or anti-glaucoma or ocular anti-hypertension agent. In some embodiments, the pharmaceutical composition is specifically formulated for peri-ocular delivery in accordance with the teachings herein.

In some embodiments, the lipophilic compound is not delivered systemically when the pharmaceutical composition is administered to the subject. In some embodiments, the lipophilic compound is not delivered by direct application into the tears and/or tear ducts of the subject. In some embodiments, the lipophilic compound is not delivered by direct application to an ocular surface of the subject (e.g., the cornea, conjunctiva). In some embodiments, the pharmaceutical composition is not a liquid topical ocular suspension, emulsion, or suspension (i.e., eye drops). In some embodiments, the lipophilic compound is a steroid. In some embodiments, the lipophilic compound is an antibiotic. In some embodiments, the lipophilic compound is an immunomodulatory drug. In some embodiments, the lipophilic compound is an integrin antagonist. In some embodiments, the lipophilic compound is an anti-inflammatory agent. In some embodiments, the lipophilic compound is an anti-glaucoma or ocular anti-hypertension agent.

Steroids

In some aspects, the present disclosure relates to a pharmaceutical composition comprising a steroid as the lipophilic compound. Accordingly, in some embodiments, the pharmaceutical composition comprises a therapeutically effective amount of a steroid, and a pharmaceutically acceptable carrier adapted for pen-ocular transdermal delivery of the steroid to one or more pen-orbital (e.g., oil-secreting pen-orbital) glands of a subject, wherein the pharmaceutical composition is specifically formulated for pen-ocular delivery. Any suitable steroid known in the art may be used in a pharmaceutical composition of the present disclosure, including, for example, the compound of Formula I, fluocinolone, medrysone, difluprednate, fluticasone, fluorometholone, loteprednol, dexamethasone, prednisolone, triamcinolone acetonide, rimexolone, cortisol, cortisone, hydrocortisone, and testosterone, or any ester derivatives thereof. In some embodiments, the steroid is a glucocorticoid. In some embodiments, the steroid is the compound of Formula I, difluprednate, loteprednol, dexamethasone, prednisolone, triamcinolone acetonide, or any ester derivative thereof. In some embodiments, the steroid is the compound of Formula I. As used herein, "the compound of Formula I" refers to the compound 6α,9α-difluoro-11 β-hydroxy-16α-methyl-3-oxo-17α-(2,2,3,3-tetramethycyclopropylcarbonyl)oxy-androsta-1,4-diene-17β-carboxylic acid cyanomethyl ester. See e.g., U.S. Pat. No. 7,291,609, including for methods of making the same. A structure of the compound of Formula I is shown below:

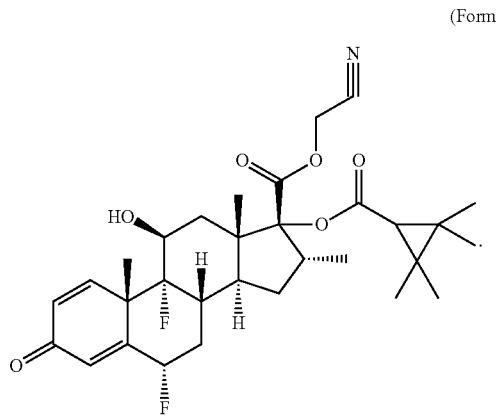

(Formula I)

In some embodiments, the pharmaceutical composition comprises the steroid at a concentration between 0.001% and 10% weight per weight (w/w). For example, the pharmaceutical composition may comprise the steroid at a concentration from about 0.001% to about 10%, from about 0.001% to about 9%, from about 0.001% to about 8%, from about 0.001% to about 7%, from about 0.001% to about 6%, from about 0.001% to about 5%, from about 0.001% to about 4%, from about 0.001% to about 3%, from about 0.001% to about 2%, from about 0.001% to about 1%, from about 0.001% to about 0.5%, from about 0.001% to about 0.1%, from about 0.001% to about 0.05%, from about 0.001% to about 0.01%, from about 0.001% to about 0.005%, from about 0.01% to about 10%, from about 0.01% to about 9%, from about 0.01% to about 8%, from about 0.01% to about 7%, from about 0.01% to about 6%, from about 0.01% to about 5%, from about 0.01% to about 4%, from about 0.01% to about 3%, from about 0.01% to about 2%, from about 0.01% to about 1%, from about 0.01% to about 0.5%, from about 0.01% to about 0.1%, from about 0.01% to about 0.05%, from about 0.05% to about 10%, from about 0.05% to about 9%, from about 0.05% to about 8%, from about 0.05% to about 7%, from about 0.05% to about 6%, from about 0.05% to about 5%, from about 0.05% to about 4%, from about 0.05% to about 3%, from about 0.05% to about 2%, from about 0.05% to about 1%, from about 0.05% to about 0.5%, from about 0.05% to about 0.1%, from about 0.1% to about 10%, from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.1% to about 0.5%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 0.5% to about 1%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 2% to about 10%, from about 2% to about 9%, from about 2% to about 8%, from about 2% to about 7%, from about 2% to about 6%, from about 2% to about 5%, from about 2% to about 4%, from about 2% to about 3%, from about 3% to about 10%, from about 3% to about 9%, from about 3% to about 8%, from about 3% to about 7%, from about 3% to about 6%, from about 3% to about 5%, from about 3% to about 4%, from about 4% to about 10%, from about 4% to about 9%, from about 4% to about 8%, from about 4% to about 7%, from about 4% to about 6%, from about 4% to about 5%, from about 5% to about 10%, from about 5% to about 9%, from about 5% to about 8%, from about 5% to about 7%, from about 5% to about 6%, from about 6% to about 10%, from about 6% to about 9%, from about 6% to about 8%, from about 6% to about 7%, from about 7% to about 10%, from about 7% to about 9%, from about 7% to about 8%, from about 8% to about 10%, from about 8% to about 9%, or from about 9% to about 10% w/w. In some embodiments, the pharmaceutical composition comprises the steroid from about 0.01% to about 2% w/w. In some embodiments, the pharmaceutical composition comprises the steroid at any of a concentration of about 0.001%, 0.005%, 0.01%, 0.05%, 0.1%, 0.2%, 0.3%, 0.4%, 0.5%, 0.6%, 0.7%, 0.8%, 0.9%, 1%, 1.25%, 1.5%, 1.75%, 2%, 2.25%, 2.5%, 2.75%, 3%, 3.5%, 4%, 4.5%, 5%, 5.5%, 6%, 6.5%, 7%, 7.5%, 8%, 8.5%, 9%, 9.5%, or 10% w/w.

Antibiotics

In some aspects, the present disclosure relates to a pharmaceutical composition comprising a therapeutically effective amount of an antibiotic as the lipophilic compound. In some embodiments, the pharmaceutical composition comprises two or more (e.g., two or more, three or more, four or more, five or more, etc.) antibiotics. Accordingly, in some embodiments, the pharmaceutical composition comprises a therapeutically effective amount of an antibiotic, and a pharmaceutically acceptable carrier adapted for peri-ocular transdermal delivery of the antibiotic to one or more peri-orbital (e.g., oil-secreting peri-orbital) glands of a subject, wherein the pharmaceutical composition is specifically formulated for peri-ocular delivery. Any suitable antibiotic known in the art may be used in the pharmaceutical compositions of the present disclosure, including, for example, sulfonamides, macrolides, chloramphenicol, aminoglycosides, fluoroquinolones, vancomycin, tetracyclines, and any combinations thereof. Examples of such antibiotics include, without limitation, azithromycin, erythromycin, gentamicin, natamycin, neomycin, tobramycin, vancomycin, bacitracin, besifloxacin, ciprofloxacin, gatifloxacin, levofloxacin, moxifloxacin, oxifloxacin, chloramphenicol, doxycycline, tetracyclin, gramicidin, mupirocin, polymyxin B, sulfacetamide.

In some embodiments, the pharmaceutical composition comprises the antibiotic at a concentration between 0.0001% and 10% weight per weight (w/w). For example, the pharmaceutical composition may comprise the antibiotic at a concentration from about from about 0.0001% to about 10%, from about 0.0001% to about 9%, from about 0.0001% to about 8%, from about 0.0001% to about 7%, from about 0.0001% to about 6%, from about 0.0001% to about 5%, from about 0.0001% to about 4%, from about 0.0001% to about 3%, from about 0.0001% to about 2%, from about 0.0001% to about 1%, from about 0.0001% to about 0.5%, from about 0.0001% to about 0.1%, from about 0.0001% to about 0.05%, from about 0.0001% to about 0.01%, from about 0.0001% to about 0.005%, about 0.0001% to about 0.001%, about 0.0001% to about 0.0005%, about 0.0005% to about 10%, from about 0.0005% to about 9%, from about 0.0005% to about 8%, from about 0.0005% to about 7%, from about 0.0005% to about 6%, from about 0.0005% to about 5%, from about 0.0005% to about 4%, from about 0.0005% to about 3%, from about 0.0005% to about 2%, from about 0.0005% to about 1%, from about 0.0005% to about 0.5%, from about 0.0005% to about 0.1%, from about 0.0005% to about 0.05%, from about 0.0005% to about 0.01%, from about 0.0005% to about 0.005%, about 0.0005% to about 0.001%, about 0.001% to about 10%, from about 0.001% to about 9%, from about 0.001% to about 8%, from about 0.001% to about 7%, from about 0.001% to about 6%, from about 0.001% to about 5%, from about 0.001% to about 4%, from about 0.001% to about 3%, from about 0.001% to about 2%, from about 0.001% to about 1%, from about 0.001% to about 0.5%, from about 0.001% to about 0.1%, from about 0.001% to about 0.05%, from about 0.001% to about 0.01%, from about 0.001% to about 0.005%, from about 0.01% to about 10%, from about 0.01% to about 9%, from about 0.01% to about 8%, from about 0.01% to about 7%, from about 0.01% to about 6%, from about 0.01% to about 5%, from about 0.01% to about 4%, from about 0.01% to about 3%, from about 0.01% to about 2%, from about 0.01% to about 1%, from about 0.01% to about 0.5%, from about 0.01% to about 0.1%, from about 0.01% to about 0.05%, from about 0.05% to about 10%, from about 0.05% to about 9%, from about 0.05% to about 8%, from about 0.05% to about 7%, from about 0.05% to about 6%, from about 0.05% to about 5%, from about 0.05% to about 4%, from about 0.05% to about 3%, from about 0.05% to about 2%, from about 0.05% to about 1%, from about 0.05% to about 0.5%, from about 0.05% to about 0.1%, from about 0.1% to about 10%, from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.1% to about 0.5%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 0.5% to about 1%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 2% to about 10%, from about 2% to about 9%, from about 2% to about 8%, from about 2% to about 7%, from about 2% to about 6%, from about 2% to about 5%, from about 2% to about 4%, from about 2% to about 3%, from about 3% to about 10%, from about 3% to about 9%, from about 3% to about 8%, from about 3% to about 7%, from about 3% to about 6%, from about 3% to about 5%, from about 3% to about 4%, from about 4% to about 10%, from about 4% to about 9%, from about 4% to about 8%, from about 4% to about 7%, from about 4% to about 6%, from about 4% to about 5%, from about 5% to about 10%, from about 5% to about 9%, from about 5% to about 8%, from about 5% to about 7%, from about 5% to about 6%, from about 6% to about 10%, from about 6% to about 9%, from about 6% to about 8%, from about 6% to about 7%, from about 7% to about 10%, from about 7% to about 9%, from about 7% to about 8%, from about 8% to about 10%, from about 8% to about 9%, or from about 9% to about 10% w/w. In some embodiments, the pharmaceutical composition comprises the antibiotic at a concentration between 0.0001% and 5% weight per weight (w/w). In some embodiments, the pharmaceutical composition comprises the antibiotic at any of a concentration of about 0.0001%, 0.0005%, 0.001%, 0.005%, 0.01%, 0.02%, 0.03%, 0.04%, 0.05%, 0.06%, 0.07%, 0.08%, 0.09%, 0.1%, 0.125%, 0.15%, 0.175%, 0.2%, 0.225%, 0.25%, 0.275%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.25%, 1.5%, 1.75%, 2%, 2.25%, 2.5%, 2.75%, 3%, 3.5%, 4%, 4.5%, 5%, 5.5%, 6%, 6.5%, 7%, 7.5%, 8%, 8.5%, 9%, 9.5%, or 10% w/w.

Immunomodulatory Drugs

In some aspects, the present disclosure relates to a pharmaceutical composition comprising a therapeutically effective amount of an immunomodulatory drug as the lipophilic compound. In some embodiments, the pharmaceutical composition comprises two or more (e.g., two or more, three or more, four or more, five or more, etc.) immunomodulatory drugs. Accordingly, in some embodiments, the pharmaceutical composition comprises a therapeutically effective amount of an immunomodulatory drug, and a pharmaceutically acceptable carrier adapted for peri-ocular transdermal delivery of the immunomodulatory drug to one or more peri-orbital (e.g., oil-secreting peri-orbital) glands of a subject, wherein the pharmaceutical composition is specifically formulated for peri-ocular delivery. Any suitable immunomodulatory drug known in the art may be used in the pharmaceutical compositions of the present disclosure, including, for example, calcineurin inhibitors, thalidomide analogues, and any combinations thereof. Examples of such immunomodulatory drugs include, without limitation, cyclosporine A, voclosporine, tacrolimus, pimecrolimus, thalidomide, lenalidomide, and pomalidomide. In some embodiments, the immunomodulatory drug is cyclosporine A.

In some embodiments, the pharmaceutical composition comprises the immunomodulatory drug at a concentration between 0.0001% and 5% weight per weight (w/w). For example, the pharmaceutical composition may comprise the immunomodulatory drug at a concentration from about 0.0001% to about 5%, from about 0.0001% to about 4%, from about 0.0001% to about 3%, from about 0.0001% to about 2%, from about 0.0001% to about 1%, from about 0.0001% to about 0.5%, from about 0.0001% to about 0.1%, from about 0.0001% to about 0.05%, from about 0.0001% to about 0.01%, from about 0.0001% to about 0.005%, from about 0.0001% to about 0.001%, from about 0.0001% to about 0.0005%, from about 0.0005% to about 5%, from about 0.0005% to about 4%, from about 0.0005% to about 3%, from about 0.0005% to about 2%, from about 0.0005% to about 1%, from about 0.0005% to about 0.5%, from about 0.0005% to about 0.1%, from about 0.0005% to about 0.05%, from about 0.0005% to about 0.01%, from about 0.0005% to about 0.005%, from about 0.0005% to about 0.001%, from about 0.001% to about 5%, from about 0.001% to about 4%, from about 0.001% to about 3%, from about 0.001% to about 2%, from about 0.001% to about 1%, from about 0.001% to about 0.5%, from about 0.001% to about 0.1%, from about 0.001% to about 0.05%, from about 0.001% to about 0.01%, from about 0.001% to about 0.005%, from about 0.005% to about 5%, from about 0.005% to about 4%, from about 0.005% to about 3%, from about 0.005% to about 2%, from about 0.005% to about 1%, from about 0.005% to about 0.5%, from about 0.005% to about 0.1%, from about 0.005% to about 0.05%, from about 0.005% to about 0.01%, from about 0.01% to about 5%, from about 0.01% to about 4%, from about 0.01% to about 3%, from about 0.01% to about 2%, from about 0.01% to about 1%, from about 0.01% to about 0.5%, from about 0.01% to about 0.1%, from about 0.01% to about 0.05%, from about 0.05% to about 5%, from about 0.05% to about 4%, from about 0.05% to about 3%, from about 0.05% to about 2%, from about 0.05% to about 1%, from about 0.05% to about 0.5%, from about 0.05% to about 0.1%, from about 0.1% to about 5%, from about 0.1% to about 4%, from about 0.1% to about 3%, from about 0.1% to about 2%, from about 0.1% to about 1%, from about 0.1% to about 0.5%, from about 0.5% to about 5%, from about 0.5% to about 4%, from about 0.5% to about 3%, from about 0.5% to about 2%, from about 0.5% to about 1%, from about 1% to about 5%, from about 1% to about 4%, from about 1% to about 3%, from about 1% to about 2%, from about 2% to about 5%, from about 2% to about 4%, from about 2% to about 3%, from about 3% to about 5%, from about 3% to about 4%, or from about 4% to about 5% w/w. In some embodiments, the pharmaceutical composition comprises the immunomodulatory drug at any of a concentration of about 0.0001%, 0.0005%, 0.001%, 0.005%, 0.01%, 0.02%, 0.03%, 0.04%, 0.05%, 0.06%, 0.07%, 0.08%, 0.09%, 0.1%, 0.125%, 0.15%, 0.175%, 0.2%, 0.225%, 0.25%, 0.275%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 2%, 3%, 4%, or 5% w/w.

Integrin Antagonists

In some aspects, the present disclosure relates to a pharmaceutical composition comprising a therapeutically effective amount of an integrin antagonist as the lipophilic compound. In some embodiments, the pharmaceutical composition comprises two or more (e.g., two or more, three or more, four or more, five or more, etc.) integrin antagonists. Accordingly, in some embodiments, the pharmaceutical composition comprises a therapeutically effective amount of an integrin antagonist, and a pharmaceutically acceptable carrier adapted for peri-ocular transdermal delivery of the integrin antagonist to one or more pen-orbital (e.g., oil-secreting pen-orbital) glands of a subject, wherein the pharmaceutical composition is specifically formulated for pen-ocular delivery. Any suitable integrin antagonist known in the art may be used in the pharmaceutical compositions of the present disclosure, including, for example, lifitegrast, GW559090, ester derivatives thereof, and any combinations thereof. In some embodiments, the pharmaceutical composition comprises GW559090 (See Krauss et al. Invest. Ophthalmol. Vis. Sci. 2015; 56(10):5888-95).

In some embodiments, the pharmaceutical composition comprises the integrin antagonist at a concentration between 0.0001% and 10% weight per weight (w/w). For example, the pharmaceutical composition may comprise the integrin antagonist at a concentration from about 0.0001% to about 10%, from about 0.0001% to about 9%, from about 0.0001% to about 8%, from about 0.0001% to about 7%, from about 0.0001% to about 6%, from about 0.0001% to about 5%, from about 0.0001% to about 4%, from about 0.0001% to about 3%, from about 0.0001% to about 2%, from about 0.0001% to about 1%, from about 0.0001% to about 0.5%, from about 0.0001% to about 0.1%, from about 0.0001% to about 0.05%, from about 0.0001% to about 0.01%, from about 0.0001% to about 0.005%, about 0.0001% to about 0.001%, about 0.0001% to about 0.0005%, about 0.0005% to about 10%, from about 0.0005% to about 9%, from about 0.0005% to about 8%, from about 0.0005% to about 7%, from about 0.0005% to about 6%, from about 0.0005% to about 5%, from about 0.0005% to about 4%, from about 0.0005% to about 3%, from about 0.0005% to about 2%, from about 0.0005% to about 1%, from about 0.0005% to about 0.5%, from about 0.0005% to about 0.1%, from about 0.0005% to about 0.05%, from about 0.0005% to about 0.01%, from about 0.0005% to about 0.005%, about 0.0005% to about 0.001%, about 0.001% to about 10%, from about 0.001% to about 9%, from about 0.001% to about 8%, from about 0.001% to about 7%, from about 0.001% to about 6%, from about 0.001% to about 5%, from about 0.001% to about 4%, from about 0.001% to about 3%, from about 0.001% to about 2%, from about 0.001% to about 1%, from about 0.001% to about 0.5%, from about 0.001% to about 0.1%, from about 0.001% to about 0.05%, from about 0.001% to about 0.01%, from about 0.001% to about 0.005%, from about 0.01% to about 10%, from about 0.01% to about 9%, from about 0.01% to about 8%, from about 0.01% to about 7%, from about 0.01% to about 6%, from about 0.01% to about 5%, from about 0.01% to about 4%, from about 0.01% to about 3%, from about 0.01% to about 2%, from about 0.01% to about 1%, from about 0.01% to about 0.5%, from about 0.01% to about 0.1%, from about 0.01% to about 0.05%, from about 0.05% to about 10%, from about 0.05% to about 9%, from about 0.05% to about 8%, from about 0.05% to about 7%, from about 0.05% to about 6%, from about 0.05% to about 5%, from about 0.05% to about 4%, from about 0.05% to about 3%, from about 0.05% to about 2%, from about 0.05% to about 1%, from about 0.05% to about 0.5%, from about 0.05% to about 0.1%, from about 0.1% to about 10%, from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.1% to about 0.5%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 0.5% to about 1%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 2% to about 10%, from about 2% to about 9%, from about 2% to about 8%, from about 2% to about 7%, from about 2% to about 6%, from about 2% to about 5%, from about 2% to about 4%, from about 2% to about 3%, from about 3% to about 10%, from about 3% to about 9%, from about 3% to about 8%, from about 3% to about 7%, from about 3% to about 6%, from about 3% to about 5%, from about 3% to about 4%, from about 4% to about 10%, from about 4% to about 9%, from about 4% to about 8%, from about 4% to about 7%, from about 4% to about 6%, from about 4% to about 5%, from about 5% to about 10%, from about 5% to about 9%, from about 5% to about 8%, from about 5% to about 7%, from about 5% to about 6%, from about 6% to about 10%, from about 6% to about 9%, from about 6% to about 8%, from about 6% to about 7%, from about 7% to about 10%, from about 7% to about 9%, from about 7% to about 8%, from about 8% to about 10%, from about 8% to about 9%, or from about 9% to about 10% w/w. In some embodiments, the pharmaceutical composition comprises the integrin antagonist at any of a concentration of about 0.0001%, 0.0005%, 0.001%, 0.005%, 0.01%, 0.02%, 0.03%, 0.04%, 0.05%, 0.06%, 0.07%, 0.08%, 0.09%, 0.1%, 0.125%, 0.15%, 0.175%, 0.2%, 0.225%, 0.25%, 0.275%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.25%, 1.5%, 1.75%, 2%, 2.25%, 2.5%, 2.75%, 3%, 3.5%, 4%, 4.5%, 5%, 5.5%, 6%, 6.5%, 7%, 7.5%, 8%, 8.5%, 9%, 9.5%, or 10% w/w.

Anti-Inflammatory Agents

In some aspects, the present disclosure relates to a pharmaceutical composition comprising a therapeutically effective amount of an anti-inflammatory agent as the lipophilic compound. In some embodiments, the pharmaceutical composition comprises two or more (e.g., two or more, three or more, four or more, five or more, etc.) anti-inflammatory agents. Accordingly, in some embodiments, the pharmaceutical composition comprises a therapeutically effective amount of an anti-inflammatory agent, and a pharmaceutically acceptable carrier adapted for peri-ocular transdermal delivery of the anti-inflammatory agent to one or more pen-orbital (e.g., oil-secreting pen-orbital) glands of a subject, wherein the pharmaceutical composition is specifically formulated for peri-ocular delivery. Any suitable anti-inflammatory agent known in the art may be used in the pharmaceutical compositions of the present disclosure, including, for example, omega 3 fatty acids, non-steroidal anti-inflammatory drugs (NSAIDS), and any combinations thereof. Examples of suitable omega 3 fatty acids may include, without limitation, eicosapentaenoic acid (EPA), docosahexaenoic acid (DHA), alpha-linolenic acid (ALA), and any combinations thereof. Examples of suitable NSAIDS may include, without limitation, bromfenac, diclofenac, indomethacin, flurbiprofen, ketorolac, nepafenac, and any combinations thereof.

In some embodiments, the pharmaceutical composition comprises the anti-inflammatory agent at a concentration between 0.0001% and 5% weight per weight (w/w). For example, the pharmaceutical composition may comprise the anti-inflammatory agent at a concentration from about 0.0001% to about 5%, from about 0.0001% to about 4%, from about 0.0001% to about 3%, from about 0.0001% to about 2%, from about 0.0001% to about 1%, from about 0.0001% to about 0.5%, from about 0.0001% to about 0.1%, from about 0.0001% to about 0.05%, from about 0.0001% to about 0.01%, from about 0.0001% to about 0.005%, from about 0.0001% to about 0.001%, from about 0.0001% to about 0.0005%, from about 0.0005% to about 5%, from about 0.0005% to about 4%, from about 0.0005% to about 3%, from about 0.0005% to about 2%, from about 0.0005% to about 1%, from about 0.0005% to about 0.5%, from about 0.0005% to about 0.1%, from about 0.0005% to about 0.05%, from about 0.0005% to about 0.01%, from about 0.0005% to about 0.005%, from about 0.0005% to about 0.001%, from about 0.001% to about 5%, from about 0.001% to about 4%, from about 0.001% to about 3%, from about 0.001% to about 2%, from about 0.001% to about 1%, from about 0.001% to about 0.5%, from about 0.001% to about 0.1%, from about 0.001% to about 0.05%, from about 0.001% to about 0.01%, from about 0.001% to about 0.005%, from about 0.005% to about 5%, from about 0.005% to about 4%, from about 0.005% to about 3%, from about 0.005% to about 2%, from about 0.005% to about 1%, from about 0.005% to about 0.5%, from about 0.005% to about 0.1%, from about 0.005% to about 0.05%, from about 0.005% to about 0.01%, from about 0.01% to about 5%, from about 0.01% to about 4%, from about 0.01% to about 3%, from about 0.01% to about 2%, from about 0.01% to about 1%, from about 0.01% to about 0.5%, from about 0.01% to about 0.1%, from about 0.01% to about 0.05%, from about 0.05% to about 5%, from about 0.05% to about 4%, from about 0.05% to about 3%, from about 0.05% to about 2%, from about 0.05% to about 1%, from about 0.05% to about 0.5%, from about 0.05% to about 0.1%, from about 0.1% to about 5%, from about 0.1% to about 4%, from about 0.1% to about 3%, from about 0.1% to about 2%, from about 0.1% to about 1%, from about 0.1% to about 0.5%, from about 0.5% to about 5%, from about 0.5% to about 4%, from about 0.5% to about 3%, from about 0.5% to about 2%, from about 0.5% to about 1%, from about 1% to about 5%, from about 1% to about 4%, from about 1% to about 3%, from about 1% to about 2%, from about 2% to about 5%, from about 2% to about 4%, from about 2% to about 3%, from about 3% to about 5%, from about 3% to about 4%, or from about 4% to about 5% w/w. In some embodiments, the pharmaceutical composition comprises the anti-inflammatory agent at any of a concentration of about 0.0001%, 0.0005%, 0.001%, 0.005%, 0.01%, 0.02%, 0.03%, 0.04%, 0.05%, 0.06%, 0.07%, 0.08%, 0.09%, 0.1%, 0.125%, 0.15%, 0.175%, 0.2%, 0.225%, 0.25%, 0.275%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 2%, 3%, 4%, or 5% w/w.

Anti-Glaucoma Drugs or Ocular Anti-Hypertension Agents

In some aspects, the present disclosure relates to a pharmaceutical composition comprising a therapeutically effective amount of an anti-glaucoma drug or ocular anti-hypertension agent as the lipophilic compound. In some embodiments, the pharmaceutical composition comprises two or more (e.g., two or more, three or more, four or more, five or more, etc.) anti-glaucoma drugs or ocular anti-hypertension agents. Accordingly, in some embodiments, the pharmaceutical composition comprises a therapeutically effective amount of an anti-glaucoma drug or ocular anti-hypertension agent, and a pharmaceutically acceptable carrier adapted for peri-ocular transdermal delivery of the anti-glaucoma drug or ocular anti-hypertension agents to one or more pen-orbital (e.g., oil-secreting peri-orbital) glands of a subject, wherein the pharmaceutical composition is specifically formulated for pen-ocular delivery. Any suitable anti-glaucoma drug or ocular anti-hypertension agent known in the art may be used in the pharmaceutical compositions of the present disclosure, including, for example, prostaglandin analogs, beta blockers, alpha-2 agonists, carbonic anhydrase inhibitors, Rho kinase inhibitors, and any combinations thereof. Examples of suitable prostaglandin analogs may include, without limitiation, bimatoprost, latanoprost, travoprost, tafluprost, latanoprostene-bunod, and any combinations thereof. Examples of suitable beta blockers may include, without limitiation, timolol, betaxolol, levobunolol, metipranolol, and any combinations thereof. Examples of suitable alpha-2 agonists may include brimonidine, clonidine, apraclonidine, and any combinations thereof. Examples of suitable carbonic anhydrase inhibitors may include, without limitiation, dorzolamide, brinzolamide, acetazolamide, methazolamide, and any combinations thereof. Examples of suitable Rho kinase inhibitors may include, without limitiation, netarsudil, and any combinations thereof.

In some embodiments, the pharmaceutical composition comprises the anti-glaucoma drug or ocular anti-hypertension agent at a concentration between 0.0001% and 10% weight per weight (w/w). For example, the pharmaceutical composition may comprise the anti-glaucoma drug or ocular anti-hypertension agent at a concentration from about 0.0001% to about 10%, from about 0.0001% to about 9%, from about 0.0001% to about 8%, from about 0.0001% to about 7%, from about 0.0001% to about 6%, from about 0.0001% to about 5%, from about 0.0001% to about 4%, from about 0.0001% to about 3%, from about 0.0001% to about 2%, from about 0.0001% to about 1%, from about 0.0001% to about 0.5%, from about 0.0001% to about 0.1%, from about 0.0001% to about 0.05%, from about 0.0001% to about 0.01%, from about 0.0001% to about 0.005%, about 0.0001% to about 0.001%, about 0.0001% to about 0.0005%, about 0.0005% to about 10%, from about 0.0005% to about 9%, from about 0.0005% to about 8%, from about 0.0005% to about 7%, from about 0.0005% to about 6%, from about 0.0005% to about 5%, from about 0.0005% to about 4%, from about 0.0005% to about 3%, from about 0.0005% to about 2%, from about 0.0005% to about 1%, from about 0.0005% to about 0.5%, from about 0.0005% to about 0.1%, from about 0.0005% to about 0.05%, from about 0.0005% to about 0.01%, from about 0.0005% to about 0.005%, about 0.0005% to about 0.001%, about 0.001% to about 10%, from about 0.001% to about 9%, from about 0.001% to about 8%, from about 0.001% to about 7%, from about 0.001% to about 6%, from about 0.001% to about 5%, from about 0.001% to about 4%, from about 0.001% to about 3%, from about 0.001% to about 2%, from about 0.001% to about 1%, from about 0.001% to about 0.5%, from about 0.001% to about 0.1%, from about 0.001% to about 0.05%, from about 0.001% to about 0.01%, from about 0.001% to about 0.005%, from about 0.01% to about 10%, from about 0.01% to about 9%, from about 0.01% to about 8%, from about 0.01% to about 7%, from about 0.01% to about 6%, from about 0.01% to about 5%, from about 0.01% to about 4%, from about 0.01% to about 3%, from about 0.01% to about 2%, from about 0.01% to about 1%, from about 0.01% to about 0.5%, from about 0.01% to about 0.1%, from about 0.01% to about 0.05%, from about 0.05% to about 10%, from about 0.05% to about 9%, from about 0.05% to about 8%, from about 0.05% to about 7%, from about 0.05% to about 6%, from about 0.05% to about 5%, from about 0.05% to about 4%, from about 0.05% to about 3%, from about 0.05% to about 2%, from about 0.05% to about 1%, from about 0.05% to about 0.5%, from about 0.05% to about 0.1%, from about 0.1% to about 10%, from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.1% to about 0.5%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 0.5% to about 1%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 2% to about 10%, from about 2% to about 9%, from about 2% to about 8%, from about 2% to about 7%, from about 2% to about 6%, from about 2% to about 5%, from about 2% to about 4%, from about 2% to about 3%, from about 3% to about 10%, from about 3% to about 9%, from about 3% to about 8%, from about 3% to about 7%, from about 3% to about 6%, from about 3% to about 5%, from about 4% to about 10%, from about 4% to about 9%, from about 4% to about 8%, from about 4% to about 7%, from about 4% to about 6%, from about 5% to about 10%, from about 5% to about 9%, from about 5% to about 8%, from about 5% to about 7%, from about 5% to about 6%, from about 6% to about 10%, from about 6% to about 9%, from about 6% to about 8%, from about 6% to about 7%, from about 7% to about 10%, from about 7% to about 9%, from about 7% to about 8%, from about 8% to about 10%, from about 8% to about 9%, or from about 9% to about 10% w/w. In some embodiments, the pharmaceutical composition comprises the anti-glaucoma drug or ocular anti-hypertension agent at any of a concentration of about 0.0001%, 0.0005%, 0.001%, 0.005%, 0.01%, 0.02%, 0.03%, 0.04%, 0.05%, 0.06%, 0.07%, 0.08%, 0.09%, 0.1%, 0.125%, 0.15%, 0.175%, 0.2%, 0.225%, 0.25%, 0.275%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.25%, 1.5%, 1.75%, 2%, 2.25%, 2.5%, 2.75%, 3%, 3.5%, 4%, 4.5%, 5%, 5.5%, 6%, 6.5%, 7%, 7.5%, 8%, 8.5%, 9%, 9.5%, or 10% w/w.

Pharmaceutically Acceptable Carrier

In some aspects, the present disclosure relates to a pharmaceutical composition comprising a pharmaceutically acceptable carrier adapted for pen-ocular transdermal delivery of a steroid to one or more pen-orbital glands of a subject. In some embodiments, the pharmaceutically acceptable carrier is adapted for peri-ocular transdermal delivery by: 1) decreasing the concentration of the permeation enhancer in the carrier relative to the concentration used in a standard steroid ointment/cream formulation; 2) using a permeation enhancer (not typically found in topical steroid ointment/cream formulations) that is suitable for transdermal delivery of the steroid into the eyelid (e.g., Tween-80); 3) formulating the pharmaceutical composition to achieve improved spreadability on the pen-ocular surface relative to an ointment base; and/or 4) formulating the pharmaceutical composition to avoid flow from the pen-ocular surface onto the corneal surface.

In some embodiments, the pharmaceutically acceptable carrier comprises one or more (e.g., one or more, two or more, three or more, four or more, five or more, etc.) permeation enhancers. As used herein, a "permeation enhancer" or "penetration enhancer" may refer to a compound or mixture of compounds that interact with one or more skin constituents to promote drug penetration into and/or through the skin. Any suitable permeation enhancer known in the art may be used in the pharmaceutical compositions described herein, including, for example, surfactants (e.g., ionic (anionic, cationic, zwitterionic) surfactants (such as sodium lauryl sulfate, sodium laureate, etc.) nonionic surfactants (such as Tween-80, other polysorbates, etc.), and any combinations thereof), bile salts and derivatives thereof (e.g., sodium glyacolate, sodium deoxycholate, etc.), fatty acids and derivatives thereof (e.g., oleic acid, caprylic acid, esters of fatty acids such as isopropyl myristate, etc.), chelating agents (e.g., EDTA, citric acid, etc.), sulphoxides (e.g., DMSO, DMA, DMF, etc.), polyols (e.g., diethylene glycol monoethyl ether, PG, polyethylene glycols (PEGs), glycerol, polyglycols, etc.), alcohols (e.g., alkanols, alkenols, glycols, etc.), hydrocarbons (e.g., alkanes, alkenes, halogenated alkanes, squalene, squalene, mineral oil, etc.), amines, amides (e.g., cyclic amides, acyclic amides, azones, pyrrolidones, urea and derivatives thereof, etc.), others (e.g., terpenes and terpenoids, essential oils (such as *eucalyptus* oil, peppermint oil, turpentine oil, etc.), phospholipids, cyclic oligosaccharides (such as cyclodextrins), amino acids and thioacyl derivatives of amino acids, alkyl amino esters and oxazolidinones, enzymes, ketones (such as macrocyclic ketones), etc.), hyaluronic acid, benzalkonium chloride, and any combinations thereof.

In some embodiments, the pharmaceutically acceptable carrier is adapted for peri-ocular transdermal delivery by comprising a decreased concentration of the permeation enhancer relative to the concentration of permeation enhancer used in a typical steroid ointment/cream formulation. In some embodiments, the pharmaceutically acceptable carrier comprises about 95%, about 90%, about 85%, about 80%, about 75%, about 70%, about 65%, about 60%, about 55%, about 50%, about 45%, about 40%, about 35%, about 30%, about 35%, about 20%, about 15%, about 10%, about 5%, about 1%, about 0.1%, or about 0.01% of the concentration of the permeation enhancer as compared to the concentration of the permeation enhanced used in a typical steroid ointment/cream formulation for dermal application. In some embodiments, the pharmaceutically acceptable carrier comprises about 1-fold, about 2-fold about 3-fold about 4-fold, about 5-fold, about 6-fold, about 7-fold, about 8-fold, about 9-fold, about 10-fold, about 20-fold, about 30-fold, about 40-fold, about 50-fold or about 100-fold less permeation enhancer as compared to the concentration of the permeation enhanced used in a typical steroid ointment/cream formulation for dermal application. For example, if a typical steroid ointment comprises a given permeation enhancer (e.g., hydroxypropyl methylcellulose) at 3% w/w, then the pharmaceutical compositions of the present disclosure may include the same permeation enhancer at about 2.85%, about 2.7%, about 2.55%, about 2.4%, about 2.25%, about 2.1%, about 1.95%, about 1.8%, about 1.65%, about 1.5%, about 1.35%, about 1.2% about 1.05%, about 0.9%, about 0.75%, about 0.6%, about 0.45%, about 0.3%, about 0.03%, or about 0.003% w/w.

In some embodiments, the pharmaceutically acceptable carrier is adapted for peri-ocular transdermal delivery by comprising a permeation enhancer that is suitable for transdermal delivery of a steroid into the eyelid (e.g., but not completely through to the topical surface) of a subject. In some embodiments, the permeation enhancer that is suitable for transdermal delivery into the eyelid is a permeation enhancer specifically suitable for transdermal delivery adjacent to the eye and/or not typically found in topical steroid ointment/cream formulations (for use on other areas of the body of a subject like the hands or feet). Examples of suitable permeation enhancers for delivery into the eyelid of the subject may include, without limitation, Tween-80, polyethylene glycols (PEGs), diethylene glycol monoethyl ether, essential oils, hyaluronic acid, benzalkonium chloride (BAK), and/or any combinations thereof.

In some embodiments, the pharmaceutically acceptable carrier is adapted for peri-ocular transdermal delivery by formulating the carrier to 1) achieve improved spreadability on the pen-ocular surface relative to an ointment base; and/or 2) avoid flow from the peri-ocular surface onto the corneal surface. After application of a typical steroid ointment or cream to the skin, body heat absorbed by the cream or ointment leads to a decrease in viscosity and/or yield stress, causing a decrease in cohesiveness on contact surfaces, such as the pen-ocular skin. Decreasing cohesiveness after heat absorption is problematic for an ointment or cream being applied to the eyelids, as decreased cohesiveness can lead to the cream or ointment spreading/flowing onto the ocular surface. In some embodiments, the pharmaceutically acceptable carrier comprises characteristics and rheological features of improved spreadability, resulting in easier administration and spreading onto the eyelid surface, and absence of flow at the body temperature of a subject (e.g., 31° C., 33° C., 35° C., 37° C., etc.), particularly after being applied to the skin of a subject. In some embodiments, pharmaceutical compositions of the present disclosure are formulated such that the cohesiveness of the formulation does not significantly change after application to the skin (e.g., eyelids) of a subject. Examples of suitable additives that convey a suitable cohesiveness of the formulation may include, for example, additives that increase viscosity of the formulation such as waxes, paraffins, and elastomers. In some embodiments, the viscosity of the pharmaceutically acceptable carrier does not significantly change when heated from room temperature (e.g., 25° C.) to a temperature closer to the body temperature of a subject (e.g., 31° C., 33° C., 35° C., 37° C., etc.). In some embodiments, the viscosity of the pharmaceutically acceptable carrier does not change by more than about 10%, more than about 9%, more than about 8%, more than about 7%, more than about 6%, more than about 5%, more than about 4%, more than about 3%, more than about 2%, more than about 1%, more than about 0.5%, more than about 0.1%, or more than about 0.01% when heated from room temperature (e.g., approximately 20° C., 21° C., 22° C., 23°, C24° C., or 25° C.) to a temperature (e.g., approximately 30° C., 31° C., 32° C., 33° C., 34° C., 35° C., 36° C., or 37° C.) closer to the body temperature of the subject.

In some embodiments, the pharmaceutically acceptable carrier is an ointment, cream, lotion, gel, emulsion, suspension, oil, foam, transdermal patch, spray, or any combination thereof. In some embodiments, the pharmaceutically acceptable carrier is an ointment. In some embodiments, the pharmaceutically acceptable carrier is a cream. In some embodiments, the pharmaceutically acceptable carrier comprises one or more of buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; polyols such as glycerol (e.g., formulations including 10% glycerol) or propylene glycol; salt-forming counterions such as sodium; metal complexes (e.g. Zn-protein complexes); and/or non-ionic surfactants such as polyethylene glycol (PEG). A thorough discussion of pharmaceutically acceptable carriers is available in REMINGTON'S PHARMACEUTICAL SCIENCES (Mack Pub. Co., N.J. 1991).

In some embodiments, the pharmaceutically acceptable carrier further comprises one or more additional components. Examples of additional components may include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); wetting agents (e.g., sodium lauryl sulphate, etc.); salt solutions; alcohols; polyethylene glycols; gelatin; lactose; amylase; magnesium stearate; talc; silicic acid; viscous paraffin; hydroxymethylcellulose; polyvinylpyrrolidone; perfuming agents; colorants; moisturizers; sunscreens; and the like.

In some embodiments, the pharmaceutically acceptable carrier is an ointment comprising a water-miscible ointment base. In some embodiments, the pharmaceutically acceptable carrier is an ointment comprising a paraffinic ointment base. In some embodiments, the ointment comprises one or more (e.g., one or more, two or more, three or more, four or more, five or more, six or more, seven or more, eight of more, or all nine) of white soft paraffin, mineral oil, propylene glycol, ST cyclomethicone-SNF, labrasol, propylene carbonate, steareth 2, ST emulsifier 10, and ST elastomer-10. In some embodiments, the ointment comprises white soft paraffin, mineral oil, propylene glycol, ST cyclomethicone-SNF, labrasol, propylene carbonate, steareth 2, ST emulsifier 10, and ST elastomer-10. In some embodiments, the ointment comprises about 61.5% w/w white soft paraffin, about 8% w/w mineral oil, about 8% w/w propylene glycol, about 5% w/w of ST cyclomethicone-SNF, about 5% w/w of labrasol, about 5% w/w of propylene carbonate, about 2.5% w/w of steareth 2, about 2.5% w/w of St. emulsifier 10, and about 2.5% w/w of St. elastomer-10.

In some embodiments, the pharmaceutically acceptable carrier is a cream comprising an oil-in-water base. In some embodiments, the pharmaceutically acceptable carrier is a cream comprising a water-in-oil base. In some embodiments, the cream comprises one or more (e.g., one or more, two or more, three or more, four or more, five or more, six or more, seven or more, eight or more, nine or more, 10 or more, 11 or more, 12 or more, or all 13) of white soft paraffin/petrolatum, mineral oil, propylene glycol, cyclomethicone, ST-cyclomethicone-SNF, emulsifier 10, ST-emulsifier, ST-elastomer-10, methylparaben, dibasic sodium phosphate, citric acid, propylparaben, and purified water. In some embodiments, the cream comprises white soft paraffin/petrolatum, mineral oil, propylene glycol, ST-cyclomethicone-SNF, ST-emulsifier, ST-elastomer-10, methylparaben, dibasic sodium phosphate, citric acid, propylparaben, and purified water. In some embodiments, the cream comprises about 48% w/w white soft paraffin/petrolatum, about 8% w/w mineral oil, about 8% w/w propylene glycol, about 6.6% w/w ST-cyclomethicone-SNF, about 3.3% w/w ST-emulsifier, about 2% w/w ST-elastomer-10, about 0.08% w/w methylparaben, about 0.06% w/w dibasic sodium phosphate, about 0.05% w/w citric acid, about 0.02% w/w propylparaben, and q.s. purified water. In some embodiments, the cream comprises white soft paraffin/petrolatum, mineral oil, propylene glycol, cyclomethicone, emulsifier 10, ST-elastomer-10, methylparaben, sodium phosphate dibasic anhydrous, citric acid anhydrous, propylparaben, and purified water. In some embodiments, the cream comprises about 48% w/w white soft paraffin/petrolatum, about 8% w/w mineral oil, about 8% w/w propylene glycol, about 6.6% w/w cyclomethicone, about 3.3% w/w emulsifier 10, about 2% w/w ST-elastomer-10, about 0.08% w/w methylparaben, about 0.06% w/w sodium phosphate dibasic anhydrous, about 0.046% w/w citric acid anhydrous, about 0.02% w/w propylparaben, and q.s. purified water.

In some embodiments, the cream is preservative-free comprising white soft paraffin/petrolatum, mineral oil, propylene glycol, ST-cyclomethicone-SNF, ST-emulsifier-10, ST-elastomer-10, dibasic sodium phosphate, citric acid, and purified water. In some embodiments, the cream is preservative-free comprising 48% w/w white petrolatum, 8% w/w mineral oil, 8% w/w propylene glycol, 6.6% w/w ST-cyclomethicone-SNF, 3.3% w/w emulsifier 10, 2% w/w ST-elastomer-10, 0.06% w/w sodium phosphate dibasic anhydrous, 0.05% w/w citric acid anhydrous, and q.s. purified water.

Pharmaceutical compositions and formulations of the present disclosure may be prepared by mixing the steroid with one or more pharmaceutically acceptable carriers. The formulations to be used for in vivo administration are generally sterile. Sterility may be readily accomplished, e.g., by filtration through sterile filtration membranes, by heat exposure, and/or by gamma irradiation.

Additional Lipophilic Compounds

In some embodiments, a pharmaceutical composition of the present disclosure further comprises at least one (e.g., at least one, at least two, at least three, at least four, or at least five, etc.) additional lipophilic compound. Thus, in some embodiments, the pharmaceutical composition provided herein further comprises one or more lipophilic compounds selected from the group consisting of steroids, antibiotics, immunomodulatory drugs, integrin antagonists, anti-inflammatory agents, anti-glaucoma agents, and ocular anti-hypertension agents, and combinations thereof Steroids as Additional Lipophilic Compounds In some embodiments, a pharmaceutical composition of the present disclosure further comprises at least one additional steroid. In some embodiments, the pharmaceutical composition comprises at least two (e.g., at least two, at least three, at least four, at least five, etc.) additional steroids. Any suitable steroid known in the art may be used as the one or more additional steroids in the pharmaceutical composition, including, for example, the compound of Formula I, fluocinolone, medrysone, difluprednate, fluticasone, fluorometholone, loteprednol, dexamethasone, prednisolone, triamcinolone acetonide, rimexolone, cortisol, cortisone, hydrocortisone, and testosterone, or any ester derivatives thereof. In some embodiments, the additional steroid is a glucocorticoid. In some embodiments, the at least one additional steroid is a different steroid than the first steroid in the pharmaceutical composition. For example, the first steroid may be the compound of Formula I and the additional steroid may be triamcinolone acetonide, dexamethasone, and/or loteprednol etabonate.

In some embodiments, the pharmaceutical composition comprises one or more additional steroids each at a concentration between 0.001% and 10% weight per weight (w/w). For example, the pharmaceutical composition may comprise the additional steroid at a concentration from about 0.001% to about 10%, from about 0.001% to about 9%, from about 0.001% to about 8%, from about 0.001% to about 7%, from about 0.001% to about 6%, from about 0.001% to about 5%, from about 0.001% to about 4%, from about 0.001% to about 3%, from about 0.001% to about 2%, from about 0.001% to about 1%, from about 0.001% to about 0.5%, from about 0.001% to about 0.1%, from about 0.001% to about 0.05%, from about 0.001% to about 0.01%, from about 0.001% to about 0.005%, from about 0.01% to about 10%, from about 0.01% to about 9%, from about 0.01% to about 8%, from about 0.01% to about 7%, from about 0.01% to about 6%, from about 0.01% to about 5%, from about 0.01% to about 4%, from about 0.01% to about 3%, from about 0.01% to about 2%, from about 0.01% to about 1%, from about 0.01% to about 0.5%, from about 0.01% to about 0.1%, from about 0.01% to about 0.05%, from about 0.05% to about 10%, from about 0.05% to about 9%, from about 0.05% to about 8%, from about 0.05% to about 7%, from about 0.05% to about 6%, from about 0.05% to about 5%, from about 0.05% to about 4%, from about 0.05% to about 3%, from about 0.05% to about 2%, from about 0.05% to about 1%, from about 0.05% to about 0.5%, from about 0.05% to about 0.1%, from about 0.1% to about 10%, from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.1% to about 0.5%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 0.5% to about 1%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 2% to about 10%, from about 2% to about 9%, from about 2% to about 8%, from about 2% to about 7%, from about 2% to about 6%, from about 2% to about 5%, from about 2% to about 4%, from about 2% to about 3%, from about 3% to about 10%, from about 3% to about 9%, from about 3% to about 8%, from about 3% to about 7%, from about 3% to about 6%, from about 3% to about 5%, from about 3% to about 4%, from about 4% to about 10%, from about 4% to about 9%, from about 4% to about 8%, from about 4% to about 7%, from about 4% to about 6%, from about 4% to about 5%, from about 5% to about 10%, from about 5% to about 9%, from about 5% to about 8%, from about 5% to about 7%, from about 5% to about 6%, from about 6% to about 10%, from about 6% to about 9%, from about 6% to about 8%, from about 6% to about 7%, from about 7% to about 10%, from about 7% to about 9%, from about 7% to about 8%, from about 8% to about 10%, from about 8% to about 9%, or from about 9% to about 10% w/w. In some embodiments, the pharmaceutical composition comprises the additional steroid at any of a concentration of about 0.001%, 0.005%, 0.01%, 0.05%, 0.1%, 0.2%, 0.3%, 0.4%, 0.5%, 0.6%, 0.7%, 0.8%, 0.9%, 1%, 1.25%, 1.5%, 1.75%, 2%, 2.25%, 2.5%, 2.75%, 3%, 3.5%, 4%, 4.5%, 5%, 5.5%, 6%, 6.5%, 7%, 7.5%, 8%, 8.5%, 9%, 9.5%, or 10% w/w.

In some embodiments, the pharmaceutically acceptable steroid or its formulation has the additional advantage of not inducing thinning of the skin.

Antibiotics as Additional Lipophilic Compounds

In some embodiments, a pharmaceutical composition of the present disclosure further comprises a therapeutically effective amount of one or more antibiotics. In some embodiments, the pharmaceutical composition comprises two or more (e.g., two or more, three or more, four or more, five or more, etc.) antibiotics. Any suitable antibiotic known in the art may be used in the pharmaceutical compositions of the present disclosure, including, for example, sulfonamides, macrolides, chloramphenicol, aminoglycosides, fluoroquinolones, vancomycin, tetracyclines, and any combinations thereof. Examples of such antibiotics include, without limitation, azithromycin, erythromycin, gentamicin, natamycin, neomycin, tobramycin, vancomycin, bacitracin, besifloxacin, ciprofloxacin, gatifloxacin, levofloxacin, moxifloxacin, oxifloxacin, chloramphenicol, doxycycline, tetracyclin, gramicidin, mupirocin, polymyxin B, sulfacetamide.

In some embodiments, the pharmaceutical composition comprises the one or more antibiotics at a concentration between 0.0001% and 10% weight per weight (w/w). For example, the pharmaceutical composition may comprise the one or more antibiotics at a concentration from about from about 0.0001% to about 10%, from about 0.0001% to about 9%, from about 0.0001% to about 8%, from about 0.0001% to about 7%, from about 0.0001% to about 6%, from about 0.0001% to about 5%, from about 0.0001% to about 4%, from about 0.0001% to about 3%, from about 0.0001% to about 2%, from about 0.0001% to about 1%, from about 0.0001% to about 0.5%, from about 0.0001% to about 0.1%, from about 0.0001% to about 0.05%, from about 0.0001% to about 0.01%, from about 0.0001% to about 0.005%, about 0.0001% to about 0.001%, about 0.0001% to about 0.0005%, about 0.0005% to about 10%, from about 0.0005% to about 9%, from about 0.0005% to about 8%, from about 0.0005% to about 7%, from about 0.0005% to about 6%, from about 0.0005% to about 5%, from about 0.0005% to about 4%, from about 0.0005% to about 3%, from about 0.0005% to about 2%, from about 0.0005% to about 1%, from about 0.0005% to about 0.5%, from about 0.0005% to about 0.1%, from about 0.0005% to about 0.05%, from about 0.0005% to about 0.01%, from about 0.0005% to about 0.005%, about 0.0005% to about 0.001%, about 0.001% to about 10%, from about 0.001% to about 9%, from about 0.001% to about 8%, from about 0.001% to about 7%, from about 0.001% to about 6%, from about 0.001% to about 5%, from about 0.001% to about 4%, from about 0.001% to about 3%, from about 0.001% to about 2%, from about 0.001% to about 1%, from about 0.001% to about 0.5%, from about 0.001% to about 0.1%, from about 0.001% to about 0.05%, from about 0.001% to about 0.01%, from about 0.001% to about 0.005%, from about 0.01% to about 10%, from about 0.01% to about 9%, from about 0.01% to about 8%, from about 0.01% to about 7%, from about 0.01% to about 6%, from about 0.01% to about 5%, from about 0.01% to about 4%, from about 0.01% to about 3%, from about 0.01% to about 2%, from about 0.01% to about 1%, from about 0.01% to about 0.5%, from about 0.01% to about 0.1%, from about 0.01% to about 0.05%, from about 0.05% to about 10%, from about 0.05% to about 9%, from about 0.05% to about 8%, from about 0.05% to about 7%, from about 0.05% to about 6%, from about 0.05% to about 5%, from about 0.05% to about 4%, from about 0.05% to about 3%, from about 0.05% to about 2%, from about 0.05% to about 1%, from about 0.05% to about 0.5%, from about 0.05% to about 0.1%, from about 0.1% to about 10%, from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.1% to about 0.5%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 0.5% to about 1%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 2% to about 10%, from about 2% to about 9%, from about 2% to about 8%, from about 2% to about 7%, from about 2% to about 6%, from about 2% to about 5%, from about 2% to about 4%, from about 2% to about 3%, from about 3% to about 10%, from about 3% to about 9%, from about 3% to about 8%, from about 3% to about 7%, from about 3% to about 6%, from about 3% to about 5%, from about 3% to about 4%, from about 4% to about 10%, from about 4% to about 9%, from about 4% to about 8%, from about 4% to about 7%, from about 4% to about 6%, from about 4% to about 5%, from about 5% to about 10%, from about 5% to about 9%, from about 5% to about 8%, from about 5% to about 7%, from about 5% to about 6%, from about 6% to about 10%, from about 6% to about 9%, from about 6% to about 8%, from about 6% to about 7%, from about 7% to about 10%, from about 7% to about 9%, from about 7% to about 8%, from about 8% to about 10%, from about 8% to about 9%, or from about 9% to about 10% w/w. In some embodiments, the pharmaceutical composition comprises the one or more antibiotics at a concentration between 0.0001% and 5% weight per weight (w/w). In some embodiments, the pharmaceutical composition comprises the one or more antibiotics at any of a concentration of about 0.0001%, 0.0005%, 0.001%, 0.005%, 0.01%, 0.02%, 0.03%, 0.04%, 0.05%, 0.06%, 0.07%, 0.08%, 0.09%, 0.1%, 0.125%, 0.15%, 0.175%, 0.2%, 0.225%, 0.25%, 0.275%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.25%, 1.5%, 1.75%, 2%, 2.25%, 2.5%, 2.75%, 3%, 3.5%, 4%, 4.5%, 5%, 5.5%, 6%, 6.5%, 7%, 7.5%, 8%, 8.5%, 9%, 9.5%, or 10% w/w.

Immunomodulatory Drugs as Additional Lipophilic Compounds

In some embodiments, a pharmaceutical composition of the present disclosure further comprises a therapeutically effective amount of one or more immunomodulatory drugs. In some embodiments, the pharmaceutical composition comprises two or more (e.g., two or more, three or more, four or more, five or more, etc.) immunomodulatory drugs. Any suitable immunomodulatory drug known in the art may be used in the pharmaceutical compositions of the present disclosure, including, for example, calcineurin inhibitors, thalidomide analogues, and any combinations thereof. Examples of such immunomodulatory drugs include, without limitation, cyclosporine A, voclosporine, tacrolimus, pimecrolimus, thalidomide, lenalidomide, and pomalidomide.

In some embodiments, the pharmaceutical composition comprises the one or more immunomodulatory drugs at a concentration between 0.0001% and 5% weight per weight (w/w). For example, the pharmaceutical composition may comprise the one or more immunomodulatory drugs at a concentration from about 0.0001% to about 5%, from about 0.0001% to about 4%, from about 0.0001% to about 3%, from about 0.0001% to about 2%, from about 0.0001% to about 1%, from about 0.0001% to about 0.5%, from about 0.0001% to about 0.1%, from about 0.0001% to about 0.05%, from about 0.0001% to about 0.01%, from about 0.0001% to about 0.005%, from about 0.0001% to about 0.001%, from about 0.0001% to about 0.0005%, from about 0.0005% to about 5%, from about 0.0005% to about 4%, from about 0.0005% to about 3%, from about 0.0005% to about 2%, from about 0.0005% to about 1%, from about 0.0005% to about 0.5%, from about 0.0005% to about 0.1%, from about 0.0005% to about 0.05%, from about 0.0005% to about 0.01%, from about 0.0005% to about 0.005%, from about 0.0005% to about 0.001%, from about 0.001% to about 5%, from about 0.001% to about 4%, from about 0.001% to about 3%, from about 0.001% to about 2%, from about 0.001% to about 1%, from about 0.001% to about 0.5%, from about 0.001% to about 0.1%, from about 0.001% to about 0.05%, from about 0.001% to about 0.01%, from about 0.001% to about 0.005%, from about 0.005% to about 5%, from about 0.005% to about 4%, from about 0.005% to about 3%, from about 0.005% to about 2%, from about 0.005% to about 1%, from about 0.005% to about 0.5%, from about 0.005% to about 0.1%, from about 0.005% to about 0.05%, from about 0.005% to about 0.01%, from about 0.01% to about 5%, from about 0.01% to about 4%, from about 0.01% to about 3%, from about 0.01% to about 2%, from about 0.01% to about 1%, from about 0.01% to about 0.5%, from about 0.01% to about 0.1%, from about 0.01% to about 0.05%, from about 0.05% to about 5%, from about 0.05% to about 4%, from about 0.05% to about 3%, from about 0.05% to about 2%, from about 0.05% to about 1%, from about 0.05% to about 0.5%, from about 0.05% to about 0.1%, from about 0.1% to about 5%, from about 0.1% to about 4%, from about 0.1% to about 3%, from about 0.1% to about 2%, from about 0.1% to about 1%, from about 0.1% to about 0.5%, from about 0.5% to about 5%, from about 0.5% to about 4%, from about 0.5% to about 3%, from about 0.5% to about 2%, from about 0.5% to about 1%, from about 1% to about 5%, from about 1% to about 4%, from about 1% to about 3%, from about 1% to about 2%, from about 2% to about 5%, from about 2% to about 4%, from about 2% to about 3%, from about 3% to about 5%, from about 3% to about 4%, or from about 4% to about 5% w/w. In some embodiments, the pharmaceutical composition comprises the one or more immunomodulatory drugs at any of a concentration of about 0.0001%, 0.0005%, 0.001%, 0.005%, 0.01%, 0.02%, 0.03%, 0.04%, 0.05%, 0.06%, 0.07%, 0.08%, 0.09%, 0.1%, 0.125%, 0.15%, 0.175%, 0.2%, 0.225%, 0.25%, 0.275%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 2%, 3%, 4%, or 5% w/w.

Integrin Antagonists as Additional Lipophilic Compounds

In some embodiments, a pharmaceutical composition of the present disclosure further comprises a therapeutically effective amount of one or more integrin antagonists. In some embodiments, the pharmaceutical composition comprises two or more (e.g., two or more, three or more, four or more, five or more, etc.) integrin antagonists. Any suitable integrin antagonist known in the art may be used in the pharmaceutical compositions of the present disclosure, including, for example, lifitegrast, GW559090, ester derivatives thereof, and any combinations thereof. In some embodiments, the pharmaceutical composition comprises GW559090 (See Krauss et al. Invest. Ophthalmol. Vis. Sci. 2015; 56(10):5888-95).

In some embodiments, the pharmaceutical composition comprises the one or more integrin antagonists at a concentration between 0.0001% and 10% weight per weight (w/w). For example, the pharmaceutical composition may comprise the one or more integrin antagonists at a concentration from about 0.0001% to about 10%, from about 0.0001% to about 9%, from about 0.0001% to about 8%, from about 0.0001% to about 7%, from about 0.0001% to about 6%, from about 0.0001% to about 5%, from about 0.0001% to about 4%, from about 0.0001% to about 3%, from about 0.0001% to about 2%, from about 0.0001% to about 1%, from about 0.0001% to about 0.5%, from about 0.0001% to about 0.1%, from about 0.0001% to about 0.05%, from about 0.0001% to about 0.01%, from about 0.0001% to about 0.005%, about 0.0001% to about 0.001%, about 0.0001% to about 0.0005%, about 0.0005% to about 10%, from about 0.0005% to about 9%, from about 0.0005% to about 8%, from about 0.0005% to about 7%, from about 0.0005% to about 6%, from about 0.0005% to about 5%, from about 0.0005% to about 4%, from about 0.0005% to about 3%, from about 0.0005% to about 2%, from about 0.0005% to about 1%, from about 0.0005% to about 0.5%, from about 0.0005% to about 0.1%, from about 0.0005% to about 0.05%, from about 0.0005% to about 0.01%, from about 0.0005% to about 0.005%, about 0.0005% to about 0.001%, about 0.001% to about 10%, from about 0.001% to about 9%, from about 0.001% to about 8%, from about 0.001% to about 7%, from about 0.001% to about 6%, from about 0.001% to about 5%, from about 0.001% to about 4%, from about 0.001% to about 3%, from about 0.001% to about 2%, from about 0.001% to about 1%, from about 0.001% to about 0.5%, from about 0.001% to about 0.1%, from about 0.001% to about 0.05%, from about 0.001% to about 0.01%, from about 0.001% to about 0.005%, from about 0.01% to about 10%, from about 0.01% to about 9%, from about 0.01% to about 8%, from about 0.01% to about 7%, from about 0.01% to about 6%, from about 0.01% to about 5%, from about 0.01% to about 4%, from about 0.01% to about 3%, from about 0.01% to about 2%, from about 0.01% to about 1%, from about 0.01% to about 0.5%, from about 0.01% to about 0.1%, from about 0.01% to about 0.05%, from about 0.05% to about 10%, from about 0.05% to about 9%, from about 0.05% to about 8%, from about 0.05% to about 7%, from about 0.05% to about 6%, from about 0.05% to about 5%, from about 0.05% to about 4%, from about 0.05% to about 3%, from about 0.05% to about 2%, from about 0.05% to about 1%, from about 0.05% to about 0.5%, from about 0.05% to about 0.1%, from about 0.1% to about 10%, from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.1% to about 0.5%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 0.5% to about 1%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 2% to about 10%, from about 2% to about 9%, from about 2% to about 8%, from about 2% to about 7%, from about 2% to about 6%, from about 2% to about 5%, from about 2% to about 4%, from about 2% to about 3%, from about 3% to about 10%, from about 3% to about 9%, from about 3% to about 8%, from about 3% to about 7%, from about 3% to about 6%, from about 3% to about 5%, from about 3% to about 4%, from about 4% to about 10%, from about 4% to about 9%, from about 4% to about 8%, from about 4% to about 7%, from about 4% to about 6%, from about 4% to about 5%, from about 5% to about 10%, from about 5% to about 9%, from about 5% to about 8%, from about 5% to about 7%, from about 5% to about 6%, from about 6% to about 10%, from about 6% to about 9%, from about 6% to about 8%, from about 6% to about 7%, from about 7% to about 10%, from about 7% to about 9%, from about 7% to about 8%, from about 8% to about 10%, from about 8% to about 9%, or from about 9% to about 10% w/w. In some embodiments, the pharmaceutical composition comprises the one or more integrin antagonists at any of a concentration of about 0.0001%, 0.0005%, 0.001%, 0.005%, 0.01%, 0.02%, 0.03%, 0.04%, 0.05%, 0.06%, 0.07%, 0.08%, 0.09%, 0.1%, 0.125%, 0.15%, 0.175%, 0.2%, 0.225%, 0.25%, 0.275%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.25%, 1.5%, 1.75%, 2%, 2.25%, 2.5%, 2.75%, 3%, 3.5%, 4%, 4.5%, 5%, 5.5%, 6%, 6.5%, 7%, 7.5%, 8%, 8.5%, 9%, 9.5%, or 10% w/w.

Anti-Inflammatory Agents as Additional Lipophilic Compounds

In some embodiments, a pharmaceutical composition of the present disclosure further comprises a therapeutically effective amount of one or more anti-inflammatory agents. In some embodiments, the pharmaceutical composition comprises two or more (e.g., two or more, three or more, four or more, five or more, etc.) anti-inflammatory agents. Any suitable anti-inflammatory agent known in the art may be used in the pharmaceutical compositions of the present disclosure, including, for example, omega 3 fatty acids, non-steroidal anti-inflammatory drugs (NSAIDS), and any combinations thereof. Examples of suitable omega 3 fatty acids may include, without limitation, eicosapentaenoic acid (EPA), docosahexaenoic acid (DHA), alpha-linolenic acid (ALA), and any combinations thereof Examples of suitable NSAIDS may include, without limitation, bromfenac, diclofenac, indomethacin, flurbiprofen, ketorolac, nepafenac, and any combinations thereof.

In some embodiments, the pharmaceutical composition comprises the one or more anti-inflammatory agents at a concentration between 0.0001% and 5% weight per weight (w/w). For example, the pharmaceutical composition may comprise the one or more anti-inflammatory agents at a concentration from about 0.0001% to about 5%, from about 0.0001% to about 4%, from about 0.0001% to about 3%, from about 0.0001% to about 2%, from about 0.0001% to about 1%, from about 0.0001% to about 0.5%, from about 0.0001% to about 0.1%, from about 0.0001% to about 0.05%, from about 0.0001% to about 0.01%, from about 0.0001% to about 0.005%, from about 0.0001% to about 0.001%, from about 0.0001% to about 0.0005%, from about 0.0005% to about 5%, from about 0.0005% to about 4%, from about 0.0005% to about 3%, from about 0.0005% to about 2%, from about 0.0005% to about 1%, from about 0.0005% to about 0.5%, from about 0.0005% to about 0.1%, from about 0.0005% to about 0.05%, from about 0.0005% to about 0.01%, from about 0.0005% to about 0.005%, from about 0.0005% to about 0.001%, from about 0.001% to about 5%, from about 0.001% to about 4%, from about 0.001% to about 3%, from about 0.001% to about 2%, from about 0.001% to about 1%, from about 0.001% to about 0.5%, from about 0.001% to about 0.1%, from about 0.001% to about 0.05%, from about 0.001% to about 0.01%, from about 0.001% to about 0.005%, from about 0.005% to about 5%, from about 0.005% to about 4%, from about 0.005% to about 3%, from about 0.005% to about 2%, from about 0.005% to about 1%, from about 0.005% to about 0.5%, from about 0.005% to about 0.1%, from about 0.005% to about 0.05%, from about 0.005% to about 0.01%, from about 0.01% to about 5%, from about 0.01% to about 4%, from about 0.01% to about 3%, from about 0.01% to about 2%, from about 0.01% to about 1%, from about 0.01% to about 0.5%, from about 0.01% to about 0.1%, from about 0.01% to about 0.05%, from about 0.05% to about 5%, from about 0.05% to about 4%, from about 0.05% to about 3%, from about 0.05% to about 2%, from about 0.05% to about 1%, from about 0.05% to about 0.5%, from about 0.05% to about 0.1%, from about 0.1% to about 5%, from about 0.1% to about 4%, from about 0.1% to about 3%, from about 0.1% to about 2%, from about 0.1% to about 1%, from about 0.1% to about 0.5%, from about 0.5% to about 5%, from about 0.5% to about 4%, from about 0.5% to about 3%, from about 0.5% to about 2%, from about 0.5% to about 1%, from about 1% to about 5%, from about 1% to about 4%, from about 1% to about 3%, from about 1% to about 2%, from about 2% to about 5%, from about 2% to about 4%, from about 2% to about 3%, from about 3% to about 5%, from about 3% to about 4%, or from about 4% to about 5% w/w. In some embodiments, the pharmaceutical composition comprises the one or more anti-inflammatory agents at any of a concentration of about 0.0001%, 0.0005%, 0.001%, 0.005%, 0.01%, 0.02%, 0.03%, 0.04%, 0.05%, 0.06%, 0.07%, 0.08%, 0.09%, 0.1%, 0.125%, 0.15%, 0.175%, 0.2%, 0.225%, 0.25%, 0.275%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 2%, 3%, 4%, or 5% w/w.

Anti-Glaucoma Drugs and Ocular Anti-Hypertension Agents and as Additional Lipophilic Compounds In some embodiments, a pharmaceutical composition of the present disclosure further comprises a therapeutically effective amount of one or more anti-glaucoma drugs or ocular anti-hypertension agents. In some embodiments, the pharmaceutical composition comprises two or more (e.g., two or more, three or more, four or more, five or more, etc.) anti-glaucoma drugs or ocular anti-hypertension agents. Any suitable anti-glaucoma drug or ocular anti-hypertension agent known in the art may be used in the pharmaceutical compositions of the present disclosure, including, for example, prostaglandin analogs, beta blockers, alpha-2 agonists, carbonic anhydrase inhibitors, Rho kinase inhibitors, and any combinations thereof. Examples of suitable prostaglandin analogs may include, without limitation, bimatoprost, latanoprost, travoprost, tafluprost, latanoprostenebunod, and any combinations thereof. Examples of suitable beta blockers may include, without limitation, timolol, betaxolol, levobunolol, metipranolol, and any combinations thereof. Examples of suitable alpha-2 agonists may include brimonidine, clonidine, apraclonidine, and any combinations thereof. Examples of suitable carbonic anhydrase inhibitors may include, without limitation, dorzolamide, brinzolamide, acetazolamide, methazolamide, and any combinations thereof. Examples of suitable Rho kinase inhibitors may include, without limitiation, netarsudil, and any combinations thereof.

In some embodiments, the pharmaceutical composition comprises the one or more anti-glaucoma drug or ocular anti-hypertension agent at a concentration between 0.0001% and 10% weight per weight (w/w). For example, the pharmaceutical composition may comprise the one or more anti-glaucoma drug or ocular anti-hypertension agent at a concentration from about 0.0001% to about 10%, from about 0.0001% to about 9%, from about 0.0001% to about 8%, from about 0.0001% to about 7%, from about 0.0001% to about 6%, from about 0.0001% to about 5%, from about 0.0001% to about 4%, from about 0.0001% to about 3%, from about 0.0001% to about 2%, from about 0.0001% to about 1%, from about 0.0001% to about 0.5%, from about 0.0001% to about 0.1%, from about 0.0001% to about 0.05%, from about 0.0001% to about 0.01%, from about 0.0001% to about 0.005%, about 0.0001% to about 0.001%, about 0.0001% to about 0.0005%, about 0.0005% to about 10%, from about 0.0005% to about 9%, from about 0.0005% to about 8%, from about 0.0005% to about 7%, from about 0.0005% to about 6%, from about 0.0005% to about 5%, from about 0.0005% to about 4%, from about 0.0005% to about 3%, from about 0.0005% to about 2%, from about 0.0005% to about 1%, from about 0.0005% to about 0.5%, from about 0.0005% to about 0.1%, from about 0.0005% to about 0.05%, from about 0.0005% to about 0.01%, from about 0.0005% to about 0.005%, about 0.0005% to about 0.001%, about 0.001% to about 10%, from about 0.001% to about 9%, from about 0.001% to about 8%, from about 0.001% to about 7%, from about 0.001% to about 6%, from about 0.001% to about 5%, from about 0.001% to about 4%, from about 0.001% to about 3%, from about 0.001% to about 2%, from about 0.001% to about 1%, from about 0.001% to about 0.5%, from about 0.001% to about 0.1%, from about 0.001% to about 0.05%, from about 0.001% to about 0.01%, from about 0.001% to about 0.005%, from about 0.01% to about 10%, from about 0.01% to about 9%, from about 0.01% to about 8%, from about 0.01% to about 7%, from about 0.01% to about 6%, from about 0.01% to about 5%, from about 0.01% to about 4%, from about 0.01% to about 3%, from about 0.01% to about 2%, from about 0.01% to about 1%, from about 0.01% to about 0.5%, from about 0.01% to about 0.1%, from about 0.01% to about 0.05%, from about 0.05% to about 10%, from about 0.05% to about 9%, from about 0.05% to about 8%, from about 0.05% to about 7%, from about 0.05% to about 6%, from about 0.05% to about 5%, from about 0.05% to about 4%, from about 0.05% to about 3%, from about 0.05% to about 2%, from about 0.05% to about 1%, from about 0.05% to about 0.5%, from about 0.05% to about 0.1%, from about 0.1% to about 10%, from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.1% to about 0.5%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 0.5% to about 1%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 2% to about 10%, from about 2% to about 9%, from about 2% to about 8%, from about 2% to about 7%, from about 2% to about 6%, from about 2% to about 5%, from about 2% to about 4%, from about 2% to about 3%, from about 3% to about 10%, from about 3% to about 9%, from about 3% to about 8%, from about 3% to about 7%, from about 3% to about 6%, from about 3% to about 5%, from about 3% to about 4%, from about 4% to about 10%, from about 4% to about 9%, from about 4% to about 8%, from about 4% to about 7%, from about 4% to about 6%, from about 4% to about 5%, from about 5% to about 10%, from about 5% to about 9%, from about 5% to about 8%, from about 5% to about 7%, from about 5% to about 6%, from about 6% to about 10%, from about 6% to about 9%, from about 6% to about 8%, from about 6% to about 7%, from about 7% to about 10%, from about 7% to about 9%, from about 7% to about 8%, from about 8% to about 10%, from about 8% to about 9%, or from about 9% to about 10% w/w. In some embodiments, the pharmaceutical composition comprises the one or more anti-glaucoma drug or ocular anti-hypertension agent at any of a concentration of about 0.0001%, 0.0005%, 0.001%, 0.005%, 0.01%, 0.02%, 0.03%, 0.04%, 0.05%, 0.06%, 0.07%, 0.08%, 0.09%, 0.1%, 0.125%, 0.15%, 0.175%, 0.2%, 0.225%, 0.25%, 0.275%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.25%, 1.5%, 1.75%, 2%, 2.25%, 2.5%, 2.75%, 3%, 3.5%, 4%, 4.5%, 5%, 5.5%, 6%, 6.5%, 7%, 7.5%, 8%, 8.5%, 9%, 9.5%, or 10% w/w.

II. Methods

Certain aspects of the present disclosure relate to methods of providing prophylactic, palliative, and/or therapeutic relief of one or more signs or symptoms of an ocular disease (e.g., an ocular inflammatory condition, bacterial infection, or glaucoma) comprising administering a therapeutically effective amount of any of the pharmaceutical compositions of the present disclosure to a subject in need thereof. In some embodiments, the present disclosure relates to methods of treating an ocular disease (e.g., an ocular inflammatory condition, bacterial infection, or glaucoma) comprising administering a therapeutically effective amount of any of the pharmaceutical compositions of the present disclosure to a subject in need thereof. In some embodiments, the subject has, or is at risk of developing an ocular disease (e.g., an ocular inflammatory condition, bacterial infection, or glaucoma).

In some embodiments, the lipid structures of the eyelid (e.g., meibomian glands, meibum, other fatty tissues) serve as drug depots for the peri-ocularly delivered pharmaceutical compositions provided herein with the meibum becoming a drug delivery vehicle.

In some embodiments, the subject is a non-human animal, including, without limitation, domesticated animals (e.g., cows, sheep, cats, dogs, horses, etc.), non-human primates (e.g., monkeys), rabbits, and rodents (e.g., mice, hamsters, rats, etc.). In some embodiments, the subject is a human. In some embodiments, the subject suffers from one or more (e.g., one or more, two or more, three or more, four or more, five or more, etc.) ocular diseases and/or conditions. Examples of ocular diseases and/or conditions may include, without limitation, inflammation of the peri-ocular glands, meibomitis, dry eye disease, allergic eye disease, topical preservative toxicity, xerophthalmia, loss of homeostasis of the tear film, tear film instability and hyperosmolarity, ocular surface inflammation and damage, neuronal sensory abnormalities, meibomian gland dysfunction, exacerbated inflammatory ocular surface disease, phlyctenular keratitis, chalazion, anterior blepharitis, posterior blepharitis, bacterial infection, glaucoma, ocular hypertension, and any combinations thereof.

In some embodiments, a pharmaceutical composition of the present disclosure is topically administered to the subject. As used herein, "topically administered", "topical administration", or "topically administering" refers to the delivery of a composition to a subject by contacting, directly or otherwise, a formulation comprising the composition to a portion of the skin of a subject. The term may encompass several routes of administration including, but not limited to, topical and transdermal. Topical administration may be used as a means to deliver a composition to the epidermis or dermis of a subject, or to specific strata thereof.

In some embodiments, a pharmaceutical composition of the present disclosure is topically administered to an external portion of one or all eyelids of a subject (including the upper lateral region of one or both orbits of the subject). In some embodiments, the pharmaceutical composition is topically administered to the external portion of the upper and/or lower eyelid of one or both eyes of the subject. In some embodiments, the pharmaceutical composition is not administered directly and/or indirectly, to the ocular surface.

In some embodiments, a pharmaceutical composition of the present disclosure is topically administered to an external portion of one or all eyelids of a subject (including the upper lateral region of one or both orbits of the subject) in order to deliver lipophilic compounds (e.g., steroids) to one or more meibomian glands of the subject. In some embodiments, one or more components (e.g., a steroid) in the pharmaceutical composition are delivered to the ocular surface of a subject via the one or more meibomian glands. In some embodiments, one or more components (e.g., a steroid) in the pharmaceutical composition are delivered to the ocular surface of a subject via the meibum.

In some embodiments, a pharmaceutical composition of the present disclosure is administered one or more (e.g., one or more, two or more, three or more, four or more, five or more, six or more, seven or more, eight or more, nine or more, ten or more, etc.) times per day. In some embodiments, a pharmaceutical composition of the present disclosure is administered for one, two, three, four, five, six, seven or more consecutive days. In some embodiments, a pharmaceutical composition of the present disclosure is administered for one, two, three, four, five, six, seven or more non-consecutive days. In some embodiments, a pharmaceutical composition of the present disclosure is administered for one, two, three, four, five, six, seven, eight, nine, 10, 11, 12 or more consecutive weeks. In some embodiments, a pharmaceutical composition of the present disclosure is administered for one, two, three, four, five, six, seven, eight, nine, 10, 11, 12 or more non-consecutive weeks. In some embodiments, a pharmaceutical composition of the present disclosure is administered for one, two, three, four, five, six, seven, eight, nine, 10, 11, 12 or more consecutive months. In some embodiments, a pharmaceutical composition of the present disclosure is administered for one, two, three, four, five, six, seven, eight, nine, 10, 11, 12 or more non-consecutive months. In some embodiments, treatment is initiated with a loading dose followed by dose tapering. In some embodiments, treatment is initiated with a loading dose, followed by sustained treatment with a lower dose.

In some embodiments, the exposure level of the lipophilic compound in the eyelids, bulbar conjunctiva, cornea, iris/ciliary body (ICB), and/or aqueous humor (AQH) remains constant or substantially constant for up to 24 hours after the final peri-ocular dose application. In some embodiments, the concentration of the lipophilic compound in one or more compartments selected from the group consisting of the eyelids, bulbar conjunctiva, cornea, iris/ciliary body (ICB), and aqueous humor (AQH) differ by less than 50%, less than 40%, less than 30%, less than 25%, less than 20%, less than 15%, less than 10%, less than 9%, less than 8%, less than 7%, less than 6%, less than 5%, less than 4%, less than 3%, less than 2%, or less than 1% when comparing the concentration at 2 hours and 24 hours after the final peri-ocular dose application. In some embodiments, the concentration of the lipophilic compound in one or more compartments selected from the group consisting of the eyelids, bulbar conjunctiva, cornea, iris/ciliary body (ICB), and aqueous humor (AQH) at 24 hours after the final peri-ocular dose application is within 50%, 40%, 30%, 25%, 20%, 15%, 10%, 9%, 8%, 7%, 6%, 5%, 4%, 3%, 2%, or 1% of the concentration of the lipophilic compound at 2 hours after the final peri-ocular dose application. In some embodiments, the concentration of the lipophilic compound in the eyelids at 24 hours after the final peri-ocular dose application is within 50%, 40%, 30%, 25%, 20%, 15%, 10%, 9%, 8%, 7%, 6%, 5%, 4%, 3%, 2%, or 1% of the concentration of the lipophilic compound at 2 hours after the final peri-ocular dose application. In some embodiments, the concentration of the lipophilic compound in the eyelids at 24 hours after the final peri-ocular dose application is not less than 50%, 40%, 30%, 25%, 20%, 15%, 10%, 9%, 8%, 7%, 6%, 5%, 4%, 3%, 2%, or 1% of the concentration of the lipophilic compound at 2 hours after the final peri-ocular dose application. In some embodiments, the concentration of the lipophilic compound in one or more compartments selected from the group consisting of the eyelids, bulbar conjunctiva, cornea, iris/ciliary body (ICB), and aqueous humor (AQH) at 24 hours after the final peri-ocular dose application is not less than 50%, 40%, 30%, 25%, 20%, 15%, 10%, 9%, 8%, 7%, 6%, 5%, 4%, 3%, 2%, or 1% of the concentration of the lipophilic compound at 2 hours after the final pen-ocular dose application. In some embodiments, the concentration of the lipophilic compound in the eyelids at 24 hours after the final pen-ocular dose application is not less than 25%, 20%, 15%, 10%, 9%, 8%, 7%, 6%, 5%, 4%, 3%, 2%, or 1% of the concentration of the lipophilic compound at 2 hours after the final pen-ocular dose application.

In some embodiments, topical administration of the pharmaceutical composition as described herein provides prophylactic, palliative, and/or therapeutic relief of one or more signs of an ocular disease in a subject. In some embodiments, topical administration of the pharmaceutical composition as described herein reduces or eliminates one or more signs of an ocular disease in a subject. Examples of signs or symptoms of an ocular disease may include, without limitation, eye and/or eyelid margin redness, watery eyes, dry eyes, itching, stinging, or burning sensation of the eyes or orbits, blurry vision, difficulty with nighttime driving, night blindness, conjunctival xerosis, corneal xerosis, corneal ulcers, Bitot's spots, eye fatigue, foreign body sensation in the eye, light sensitivity, stringy mucus in or around the eyes, swelling of the conjunctiva and/or eyelids, dry, flaky, and/or damaged skin of the eyelids and/or orbits, eyelids that appear greasy, eyelid sticking, abnormal eyelash growth, loss of eyelashes, discomfort or pain of the eyes, eyelids, and/or orbits, chronic and episodic punctate keratopathy, filamentary keratopathy, recurrent corneal erosion, persistent epithelial defect, corneal melt, ocular surface failure, blepharospasm, mucopurulent discharge, appearance of a chalazion, and any combinations thereof.

In some embodiments, topical administration of the pharmaceutical composition as described herein reduces inflammation in one or more pen-orbital glands (e.g., one or more, two or more, or all three of the Meibomian, lacrimal, and/or accessory lacrimal glands) of a subject. In some embodiments, topical administration of the pharmaceutical composition as described herein reduces inflammation in one or more pen-orbital glands by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99% relative to the inflammation observed prior to administration of the pharmaceutical composition. In some embodiments, topical administration of the pharmaceutical composition reduces inflammation in one or more peri-orbital glands by about 1-fold, about 2-fold, about 3-fold, about 4-fold, about 5-fold, about 6-fold, about 7-fold, about 8-fold, about 9-fold, about 10-fold, about 100-fold, or about 1000-fold relative to the inflammation observed prior to administration of the pharmaceutical composition. In some embodiments, topical administration of the pharmaceutical composition as described herein eliminates inflammation in one or more pen-orbital glands of the subject. Methods of measuring pen-orbital gland inflammation are known in the art, including, for example, using laser in vivo confocal microscopy (IVCM) (See Qazi et al. Investigative Ophthalmology & Visual Science March 2012, Vol. 53, 593).

In some embodiments, topical administration (e.g., prolonged/protracted administration) of the pharmaceutical composition as described herein does not result in an adverse event in the subject. Examples of adverse events may include, but are not limited to, elevated intraocular pressure, the formation or worsening of cataracts, ocular infection, and any combinations there. In some embodiments, topical administration of the pharmaceutical composition does not increase/elevate intraocular pressure in the subject.

In some embodiments, the lipophilic compound is not delivered systemically to the subject by the administration of the pharmaceutical composition. In some embodiments, the lipophilic compound is not delivered to a tear or tear duct of the subject by the administration of the pharmaceutical composition. In some embodiments, the lipophilic compound is not delivered directly to an ocular surface of the subject by the administration of the pharmaceutical composition.

III. Article of Manufacture or Kit

Certain aspects of the present disclosure relate to an article of manufacture or kit comprising one or more of the pharmaceutical compositions described herein. In some embodiments, the article of manufacture or kit comprises a label and/or package insert comprising instructions for use of the one or more pharmaceutical compositions. In some embodiments, the one or more pharmaceutical compositions are provided in a container. In some embodiments, the components of the pharmaceutical composition are provided in a single container, or in two or more separate containers. In some embodiments, the article of manufacture or kit comprises the container(s) and a label or package insert on or associated with the container(s). Suitable containers may include, for example, tubes, bottles, vials, bags, etc. The container may be formed from a variety of suitable materials such as glass, plastic (such as polyvinyl chloride, polyolefin, or polyethylene), metal, and/or metal alloy (such as stainless steel). The article of manufacture or kit may further include other materials desirable from a commercial and user standpoint, including buffers, diluents, filters, syringes, applicators, and the like.

The foregoing written description is considered to be sufficient to enable one skilled in the art to practice the present disclosure. The following Examples are offered for illustrative purposes only, and are not intended to limit the scope of the present disclosure in any way. Indeed, various modifications of the present disclosure in addition to those shown and described herein will become apparent to those skilled in the art from the foregoing description and fall within the scope of the appended claims.

IV. Definitions

Before describing the present disclosure in detail, it is to be understood that this present disclosure is not limited to particular compositions or biological systems, which can, of course, vary. It is also to be understood that the terminology used herein is for the purpose of describing particular embodiments only, and is not intended to be limiting.

As used herein, the singular forms "a," "an," and "the" include plural reference unless the context clearly indicates otherwise. Thus, for example, reference to "a molecule" optionally includes a combination of two or more such molecules, and the like.

As used herein, the term "about" refers to the usual error range for the respective value readily known to the skilled person in this technical field. Reference to "about" a value or parameter herein includes (and describes) embodiments that are directed to that value or parameter per se.

As used herein, the term "and/or", as in a phrase such as "A and/or B", is intended to include both A and B; A or B; A (alone); and B (alone). Likewise, as used herein, the term "and/or", as in a phrase such as "A, B, and/or C", is intended to encompass each of the following embodiments: A, B, and C; A, B, or C; A or C; A or B; B or C; A and C; A and B; B and C; A (alone); B (alone); and C (alone).

As used herein, the terms "individual", "patient", or "subject" refer to a mammal. Mammals include, but are not limited to, domesticated animals (e.g., cows, sheep, cats, dogs, and horses), primates (e.g., humans and non-human primates such as monkeys), rabbits, and rodents (e.g., mice, hamsters, and rats). In some embodiments, the individual, patient, or subject is a human.

As used herein, the term "pharmaceutical formulation" refers to a preparation which is in such form as to permit the biological activity of an active ingredient contained therein to be effective, and which contains no additional components which are unacceptably toxic to a subject to which the formulation would be administered.

As used herein, the term "pharmaceutically acceptable carrier" refers to an ingredient in a pharmaceutical formulation, other than an active ingredient, which is nontoxic to a subject.

As used herein, the term "prevention" includes providing prophylaxis with respect to occurrence or recurrence of one or more signs or symptoms of a disorder in an individual. An individual may be predisposed to a disorder, susceptible to a disorder, or at risk of developing a disorder, but has not yet been diagnosed with the disorder.

As used herein, an individual "at risk" of developing a disorder may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of the disorder, as known in the art. An individual having one or more of these risk factors has a higher probability of developing the disorder than an individual without one or more of these risk factors.

As used herein, the term "treatment" refers to clinical intervention designed to alter the natural course of the individual or cell being treated during the course of clinical pathology. Desirable effects of treatment include, for example, decreasing the rate of disease progression, ameliorating or palliating the disease state, and improved prognosis. An individual is successfully "treated", for example, if one or more signs or symptoms associated with the disorder are mitigated or eliminated. For example, an individual is successfully "treated" if one or more symptoms associated with an inflammatory disease are mitigated or eliminated, including, but are not limited to, decreasing symptoms resulting from the disease, increasing the quality of life of those suffering from the disease, decreasing the dose of other medications required to treat the disease, and/or delaying the progression of the disease.

An "effective amount" refers to at least an amount effective, at dosages and for periods of time necessary, to achieve the desired or indicated effect, including a therapeutic or prophylactic result. An effective amount can be provided in one or more administrations.

A "therapeutically effective amount" is at least the minimum concentration required to effect a measurable improvement of one or more signs or symptoms of a particular disorder. A therapeutically effective amount herein may vary according to factors such as the disease state, age, sex, and weight of the patient. A therapeutically effective amount is also one in which any detrimental effects of the treatment are outweighed by the therapeutically beneficial effects.

The term "pen-ocular" refers to the area surrounding the eyeball but within the orbit, including eyelids and lateral regions of the orbit.

The "peri-orbital glands" are the glands in the area around the eyeball including, for example, the meibomian, lacrimal, and/or accessory lacrimal glands.

EXAMPLES

Example 1: Effect of Treatment with the Compound of Formula I on Intraocular Pressure (IOP) and Tear Formation The compound of Formula I is a fluorinated glucocorticoid with anti-inflammatory activity (See U.S. Pat. No. 7,288,536). The compound of Formula I showed close to full agonism in a variety of human in vitro assays of glucocorticoid receptor-mediated transrepression activity, and showed a partial response in a number of assays of glucocorticoid receptor-mediated transactivation. In vivo, the compound of Formula I displayed potent anti-inflammatory activity following intratracheal dosing in models of lung inflammation in the mouse and rat, and showed similar activity to fluticasone propionate (FP) in topical delayed type hypersensitivity ear inflammation, tyrosine aminotransferase induction, and chronic house dust mite models in the mouse. Interleukin-1β (IL-1β) and Tumour Necrosis Factor α (TNFα) stimulate the release of the pro-inflammatory cytokines Interleukin-6 (IL-6) and Interleukin-8 (IL-8) from a variety of cell types through activation of the NFκB pathway. FP and the compound of Formula I are able to potently and efficiently transrepress this activation across a number of systems (A549, HeLa, MG63, 16HBE, and H9 cell lines). These are the same inflammatory markers elevated in patients with aberrant inflammation of the peri-ocular glands (DEWS, 2007).

To test the effect of the compound of Formula I on intraocular pressure (IOP), eight female cynomolgus monkeys with unilateral (OS) ocular hypertension induced by prior photocoagulation (laser) procedure to the trabecular meshwork (TM) were used at an age between 11 and 14 years at the start of the study. Laser induced ocular hypertension had been created at least 9 years earlier in the study animals. Animals and treatments were randomized according to a 4×4 replications Williams-type Latin Square design layout. Following random assignment of a number between 1 and 8, the eight primates were randomized two each into four treatment groups (A-D), with treatments masked for the investigators until all data had been collected and entered into a database. The treatment groups A-D were as follows: the compound of Formula I (10 mg/mL suspension in placebo vehicle), mapracorat (10 mg/mL suspension in placebo vehicle), MAXIDEX® (dexamethasone ophthalmic suspension) (1 mg/mL), and placebo control.

Topical bilateral treatment occurred in a randomized, masked crossover format. All four treatments were investigated in parallel in two animals per treatment group during each 4-week treatment period. The assigned, masked formulation (A, B, C, or D) was administered to both eyes (OU) in a 25 μL volume three times daily (TID; at 8:30 am, 1 pm, and 5 pm). Treatment periods were separated by a 4-week washout/recovery period without topical treatment. The first period (period 1) was preceded by a 2-week run-in period during which all animals received placebo topically TID.

Conscious animals were seated in custom-designed chairs, and TOP was measured with a pneumatonometer (Classic 30, Reichert Depew) after topical application of proparacaine hydrochloride (0.13%) in both eyes (FIG. 1). Two to three measurements were taken for each eye and averaged. Data was stored and archived. During run-in and treatment periods, diurnal IOP was determined two times per week at approximately 8:30 am, 1 pm, and 5 pm. For each animal bilateral tonometry was followed immediately by topical instillation of the appropriate drug formulation A, B, C, or D. During washout periods, diurnal IOP was measured once per week in both eyes at approximately 8:30 am, 1 pm, and 5 pm. Surprisingly, topical treatment with the compound of Formula I over 4 weeks did not result in increased IOP in primates (FIG. 1). In fact, IOP in eyes treated with the compound of Formula I was similar to eyes treated with vehicle alone, and was significantly lower than dexamethasone treatment, demonstrating that the compound of Formula I does not produce the IOP increase typically associated with topical corticosteroids (e.g., dexamethasone).

Figure 2:
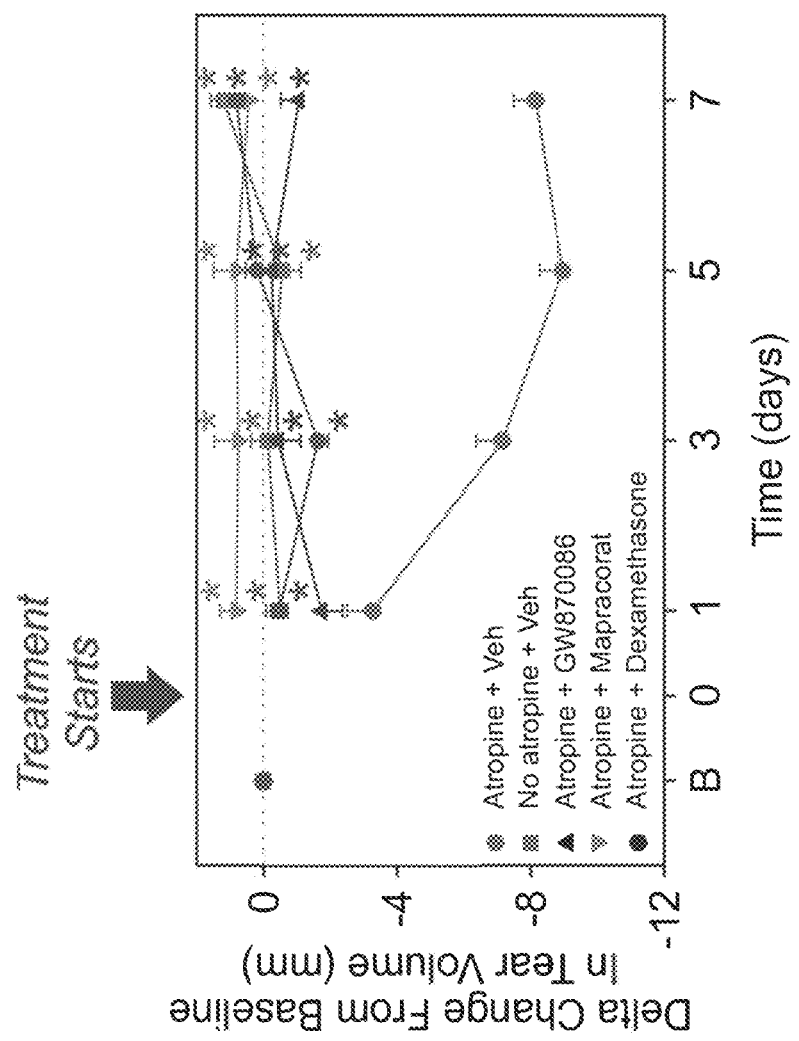
FIG. 2 shows the change in tear formation during 7 days of topical application of the indicated treatments. Repeated measures analysis followed by the Sidak's test; GW870086=compound of formula I; a * indicates a p<0.05, as compared to the atropine+vehicle-treated group.

Next, the effect on tear formation of treatment with the compound of Formula I was examined. Rabbits were placed in a restraining device, and atropine sulfate 1% ophthalmic solution (30 μL) was instilled into the lower conjunctival sac of each eye four times per day. Fifteen minutes after the administration of each dose of atropine sulfate, each eye received 30 μL of eye drops containing the active ingredient, vehicle, or saline. Tear volume was then evaluated by the Schirmer test (FIG. 2). Schirmer strips were carefully placed in the posterior (i.e., temporal) lower fornix for 60 seconds, and the wetted area was read in millimeters as an index of tear volume. Surprisingly, when administered to the ocular surface in vivo for seven days, the compound of Formula I prevented a decrease in tear formation similar to topical dexamethasone in a model of dry eye disease (FIG. 2).

Taken together, the data presented herein demonstrate that the compound of Formula I is equally effective at treating dry eye disease as topical corticosteroids, such as dexamethasone, but does not induce the negative side effect of increased IOP typically associated with administration of corticosteroid compounds to the eye. The absence of effect on TOP indicates an improved, desirable safety profile of the compound of Formula I, as compared to other steroids such as dexamethasone.

Example 2: Determining Characteristics of a Peri-Ocular Cream Formulation

The following active pharmaceutical ingredients (API) were mixed with cream vehicle for the preparation of creams containing 2% API by weight for this study and allowed to rest at room temperature for 24 hours before testing. Cyclosporin A (Sample A), loteprednol etabonate (Sample B), dexamethasone (Sample C), ketorolac tromethamine (Sample D), gatifloxacin, USP (Sample E), gentamicin sulfate (Sample F), prednisolone (Sample G), flurbiprofen (Sample H), azithromycin dihydrated (Sample J), triamcinolone acetonide (Sample K), and doxycycline hydrochloride (Sample L). Vehicle cream comprised 48% w/w white soft petrolatum, 8% w/w mineral oil, 8% w/w propylene glycol, 6.6% w/w ST-cyclomethicone-SNF, 3.3% w/w emulsifier 10, 2% w/w ST-elastomer-10, 0.08% w/w methylparaben, 0.06% w/w sodium phosphate dibasic anhydrous, 0.0546% w/w citric acid anhydrous, 0.02% w/w propylparaben, and q.s. purified water. The compound of Formula I was incorporated into a cream with the following final composition: 2% w/w compound of Formula I, 46% w/w white petrolatum, 8% w/w mineral oil, 8% w/w propylene glycol, 6.6% w/w ST-cyclomethicone-SNF, 3.3% w/w emulsifier 10, 2% w/w ST-elastomer-10, 0.08% w/w methylparaben, 0.06% w/w sodium phosphate dibasic anhydrous, 0.05% w/w citric acid anhydrous, 0.02% w/w propylparaben, and q.s. purified water.

Results of the flow visualization study are qualitative and were recorded by photograph, for each sample and each test condition. Using a wide mouth disposable pipette, a small aliquot of 2% API-containing cream at approximately 1 ml was placed into Kimble 1-dram glass vials, 15×45 mm. The vial was capped and labeled on the glass vial, A through L, as referenced in the preceding paragraph. For each test, sample vials were placed into the thermostatted couette rheometer cup at 37° C., in sets of 2 or 3 vials, and equilibrated at 37° C. for a minimum of 10 minutes. After 10 minutes, sample glass vials were removed, marked with a red line at the fluid surface or meniscus, inverted and returned to the 37° C. rheometer cup. At two time periods, 2 minutes and 5 minutes, vials were removed and photographed to document any movement of the cream.

Figure 3B:
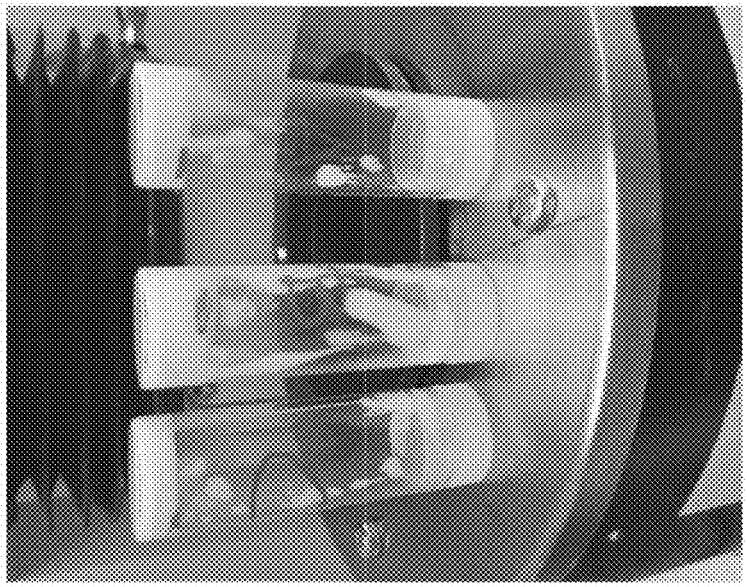
FIG. 3A and FIG. 3B shows the physical rigidity of various cream samples and a high viscosity standard equilibrated at 37° C. in glass vials and inverted for 5 minutes. Samples in FIG. 3A are 2% compound of Formula I cream (left), placebo cream (center), high viscosity polybutene standard N62000 (right); samples in FIG. 3B are 2% dexamethasone cream (vial C on left), 2% loteprednol etabonate cream (vial B in center), 2% cyclosporine A cream (vial A on right). Sample deposition on the inside of the glass vial wall was not caused by sample flow but accidental deposition from the pipette during sample transfer to the vial. That did not interfere with observation of flow or change in the meniscus with thermal treatment and inversion.
Figure 3A:
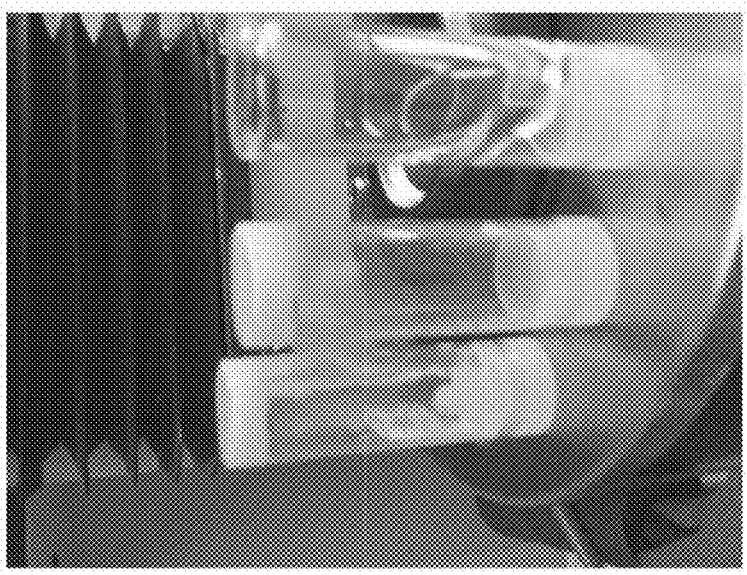
Figure 4A:
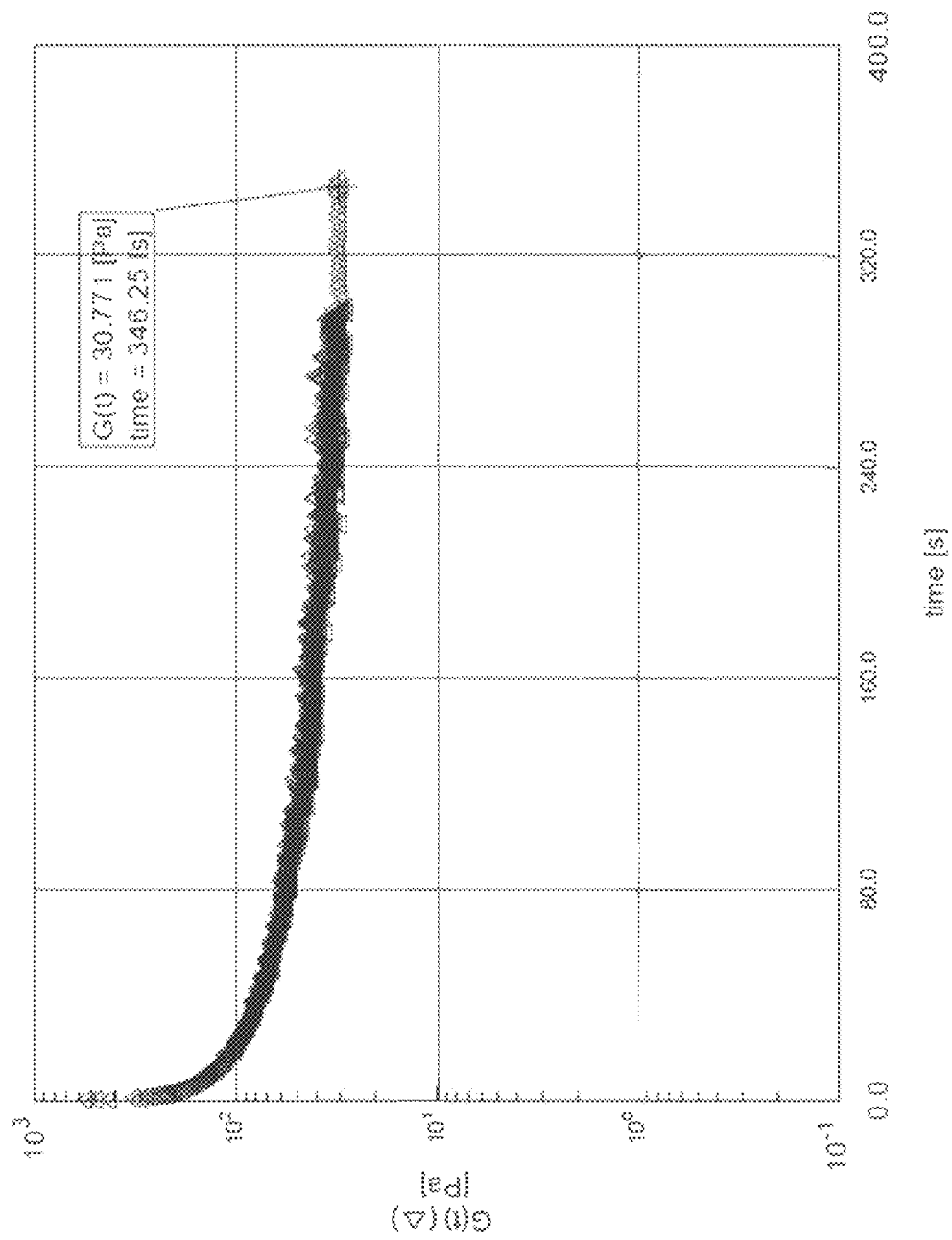
FIGS. 4A-D shows results of the step strain stress relaxation measurements for some of the samples; a) white petrolatum at 25° C.
Figure 4B:
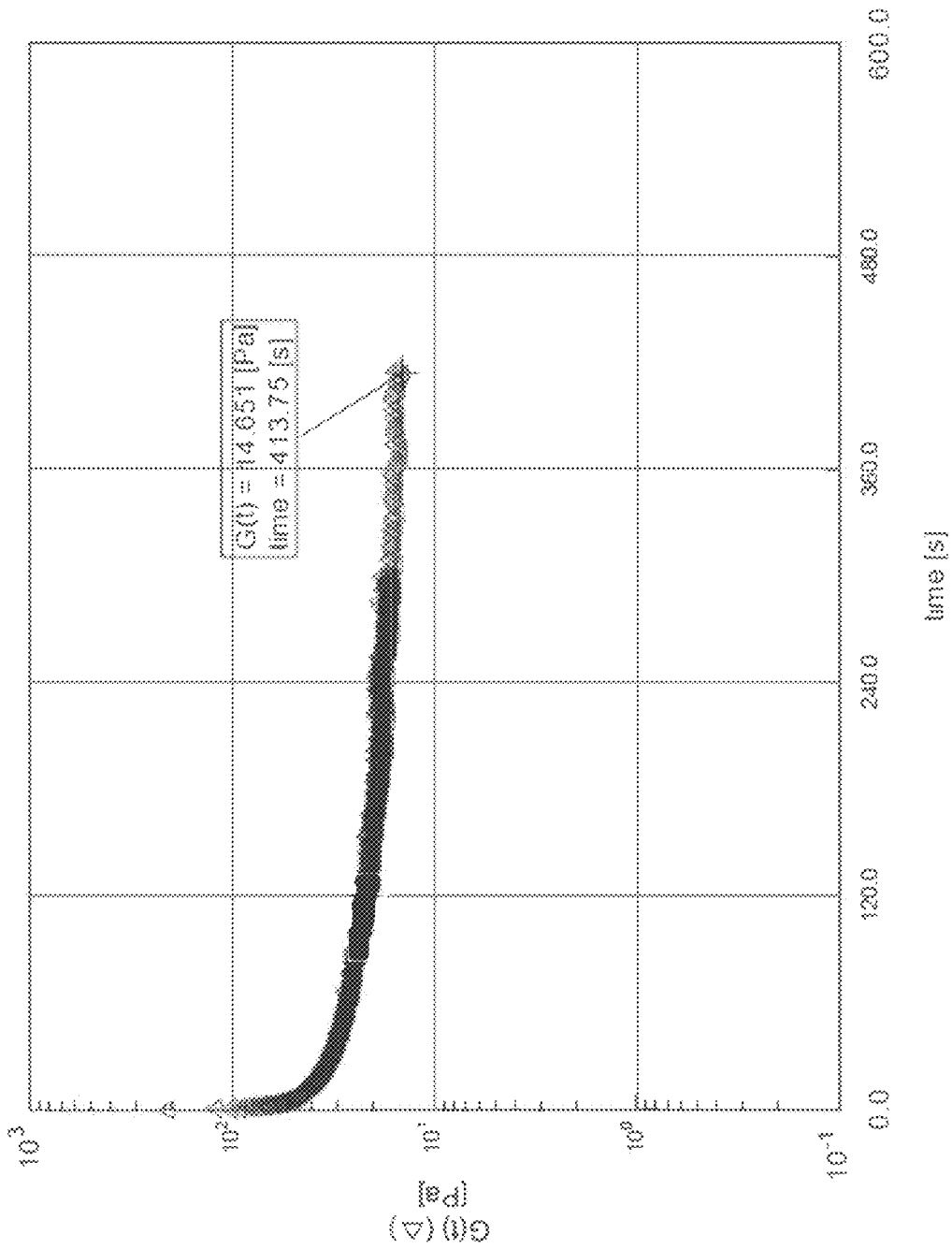
Figure 4C:
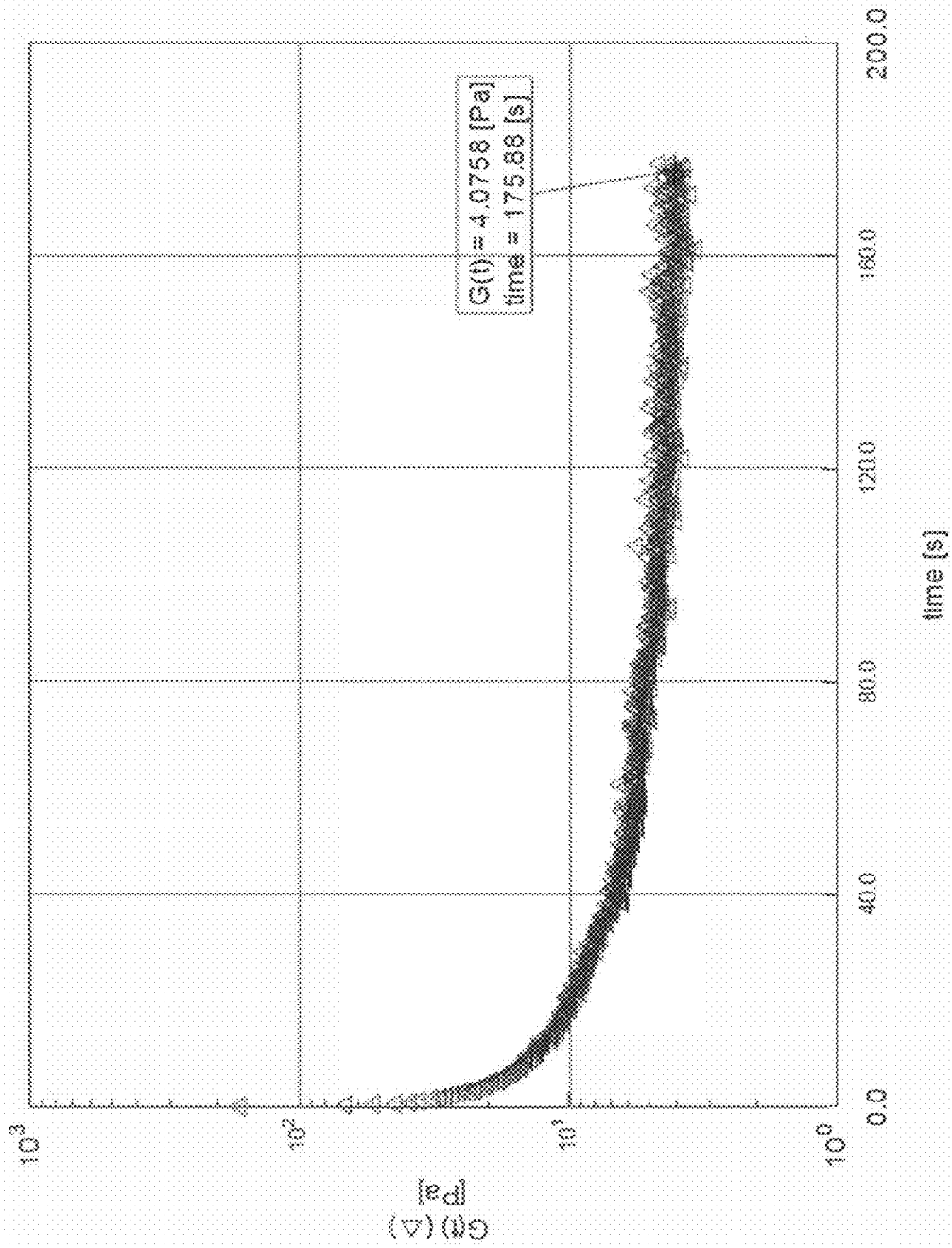
Figure 4D:
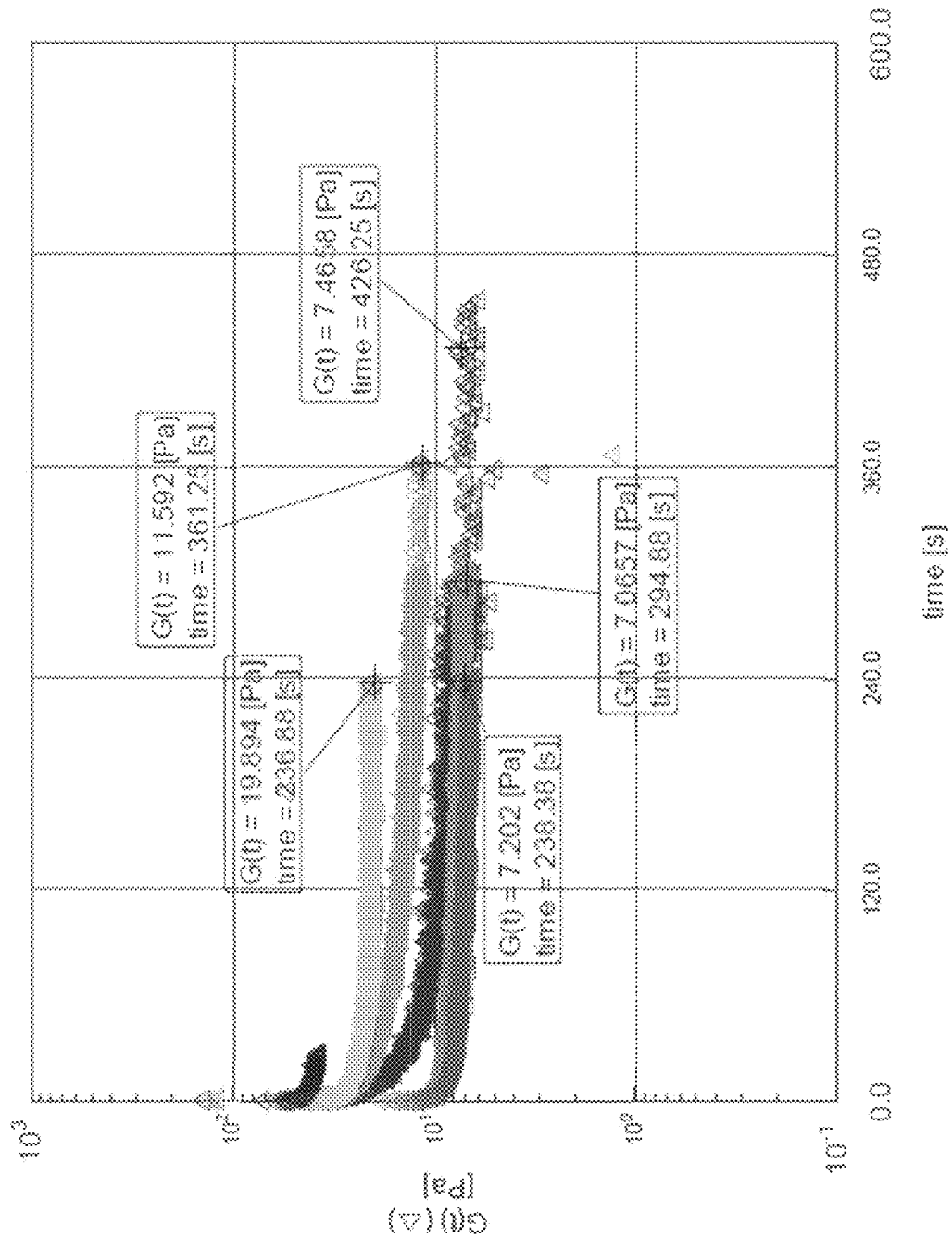

Preliminary measurements with the vehicle cream and the 2% compound of Formula I cream were made in comparison to a high viscosity polybutene standard, N62000. The vehicle cream and the 2% compound of Formula I cream showed no discernible flow at 37° C. at the 2 and 5 minute time points in contrast to the N62000 high viscosity polymer standard where bulk flow was observed (FIG. 3A). The same procedure was used for the 2% API-containing experimental cream samples prepared from the eleven compounds listed above and also tested at 37° C. This simple test shows that none of the eleven prepared 2% API-containing creams exhibited any discernible flow under the prescribed test conditions, as shown for three of the creams in FIG. 3B. In summary, the yield stress at 37° C. is apparently strong enough to prevent flow under the influence of gravity under the test conditions.

The stress relaxation yield stress test employed a rheometer and a 10% Step Strain Stress Relaxation measurement on a 25 mm cone and plate. This test applies an instantaneous motion as a step strain to the samples at t=0 and subsequently measures the shear stress relaxation. For Newtonian fluids, the relaxation is immediate. For non-Newtonian fluids, there can be a delayed stress relaxation with distribution of relaxation times with relaxation to zero. Non-Newtonian materials with yield stress will show a distribution of relaxation times with a non-zero stress relaxation—or infinite relaxation time. This is the equivalent of the yield stress. Testing was performed at both 25 and 37° C.

Measurements with Ultima white petrolatum were compared with vehicle cream and 2% API-containing creams of the compound of Formula I and the eleven APIs described above. All prepared 2% API creams, vehicle cream and Ultima white petrolatum exhibited yield stresses as determined by these step strain stress relaxation measurements. There is some variability in the data. This may be due to the insufficient mixing of the API in each vehicle cream, air entrapment during mixing, particle size of the API used in this study, and other factors. Regardless of the source of variance, each 2% API-containing cream exhibited a yield stress. So did vehicle cream and white petrolatum. Curves (some examples in FIG. 4A-D) very consistently show stress relaxation to a non-zero shear stress value. Noting that the creams are quite shear sensitive, results are summarized in the following table (Table 1) for each sample in each test at both 25 and 37° C., including Ultima petrolatum; 1-5 replicates.

TABLE 1

| Sample ID | T° C. | Yield Stress Values in Units of Pa | | | | |
|---|---|---|---|---|---|---|
| A | 25 | 10.1 | 3.0 | 10.0 | 9.5 | |
| A | 37 | 3.0 | 2.3 | | | |
| B | 25 | 15.5 | 14.6 | | | |
| B | 37 | 3.0 | 2.0 | 1.9 | | |
| C | 25 | 4.2 | 2.9 | | | |
| C | 37 | 3.4 | 1.8 | | | |
| D | 25 | 8.5 | 3.1 | 10.5 | | |
| D | 37 | 2.9 | 1.4 | | | |
| E | 25 | 17.6 | 16.9 | 3.9 | | |
| E | 37 | 5.0 | 4.0 | | | |
| F | 25 | 4.1 | 3.1 | | | |
| F | 37 | 3.6 | 3.5 | | | |
| G | 25 | 3.9 | 3.2 | | | |
| G | 37 | 1.4 | 2.7 | 4.1 | | |
| H | 25 | 18.5 | 18.9 | 5.9 | | |
| H | 37 | 2.0 | 2.3 | | | |
| J | 25 | 8.5 | 9.7 | 4.9 | | |
| J | 37 | 1.8 | 2.1 | | | |
| K | 25 | 11.6 | 7.5 | 7.2 | 7.1 | 19.9 |
| K | 37 | 6.9 | 7.1 | | | |
| L | 25 | 12.9 | 10.3 | 4.4 | | |
| L | 37 | 1.5 | 1.6 | | | |
| Ultima | 25 | 35.2 | 30.8 | | | |
| Ultima | 37 | 14.7 | | | | |

For comparison, yield stress values (in units of Pa) for the vehicle cream were 4.1, 3.3, 2.9 and 1.0, 1.0, 1.5 at 25 and 37° C., respectively (3 replicates each). Yield stress values (in units of Pa) for the 2% compound of Formula I cream were 2.2, 2.8 and 1.0, 0.9, 0.9 at 25 and 37° C., respectively (2-3 replicates each). For comparison, the stress relaxation function for the high viscosity polybutene N62000 standard showed a rapid decay to zero in less than 1 second at room temperature.

For all samples, except Samples F and G, the yield stress decreases with increasing temperature from 25° C. to 37° C. The yield stress of the Ultima petrolatum is much higher than the 2% API-containing or vehicle cream samples indicating a more difficult spreadability of the Ultima petrolatum onto contact surfaces, such as the eyelid. All 2% API creams show extensional viscosity behavior and may be strain thickening. This is a material property that may contribute to increased cohesiveness on contact surfaces, further counteracting the influence of gravity and limiting flow. More importantly, the extensional viscosity may enhance physical stability preventing sedimentation of active ingredients. These data suggest that all of the cream formulations will facilitate application to the intended surfaces (eyelids) compared to an ointment. Because of the lower yield stress of the API-containing creams and the vehicle cream, these formulations will be easier for the consumer to use and apply relative to petrolatum alone. In contrast, a high viscosity polymer such as N62000 is not likely to be suitable for the present invention. The data clearly show that the goal to develop a cream formulation that is easy to apply to a contact surface, such as the eyelid, and that does not flow following eyelid application, so as to prevent formulation flowing onto the ocular surface, has been achieved with the formulations of this invention.

Example 3: Skin Penetration of a Peri-Ocular Cream

An in vitro skin penetration model using human cadaver skin mounted in Franz-type diffusion cells (FDC) was chosen to determine the skin permeation of the compound of Formula I applied as a 2% cream to the epidermal surface. Transdermal flux into a receptor fluid was measured over a period of 46 hours after application of the formulations. At the end of the 46-hour incubation period, the skin was tape-stripped and heat separated based on an established method and the concentration of the compound of Formula I was measured in the residual epidermis and dermis. The applied formulations comprised of 2% w/w compound of Formula I, 46% w/w white petrolatum, 8% w/w mineral oil, 8% w/w propylene glycol, 6.6% w/w ST-cyclomethicone-SNF, 3.3% w/w emulsifier 10, 2% w/w ST-elastomer-10, 0.08% w/w methylparaben, 0.06% w/w sodium phosphate dibasic anhydrous, 0.05% w/w citric acid anhydrous, 0.02% w/w propylparaben, and q.s. purified water. Vehicle cream comprised of 48% w/w white petrolatum, 8% w/w mineral oil, 8% w/w propylene glycol, 6.6% w/w ST-cyclomethicone-SNF, 3.3% w/w emulsifier 10, 2% w/w ST-elastomer-10, 0.08% w/w methylparaben, 0.06% w/w sodium phosphate dibasic anhydrous, 0.05% w/w citric acid anhydrous, 0.02% w/w propylparaben, and q.s. purified water was also tested as a negative control.

Human cadaver skin from the posterior leg of a single donor, dermatomed to a thickness of approximately 250 µm, was obtained from a commercial source, cut into pieces of approximately 2 cm×2 cm with each such piece mounted in an FDC with a 0.55 cm$^2$ diffusional area and 3.3 mL receiver volume. The stratum corneum and the dermis were in contact with the donor and receptor compartments, respectively. Following an integrity check (impedance analysis), 10 µL of cream sample was applied to the epidermal surface of each FDC. An aliquot of the receptor fluid (comprised of phosphate-buffered saline pH 7.4 containing 0.01 wt % Na azide and 1 wt % Brij 020) was sampled 4, 8, 24 and 46 hours after application of test article and stored refrigerated until sample analysis. At the end of the 46-hour period, the epidermal surface of each skin sample was wiped clean, washed twice using 200 µL of a 1:1 volume water/ethanol mixture. The skin was then tapped dry using KimWipes, tape-stripped thrice with cellophane tape to remove the outer-most layers of the stratum corneum. The remaining skin was then split into epidermal and dermal compartments. The compound of Formula I was extracted with 3 mL of a 1:1 volume DMSO/isopropanol mixture at 40° C. for 24 hours.

A high performance liquid chromatography UV ("HPLC-UV") analytical method and an LC-MS/MS method for detecting the compound of Formula I in the skin and in the receptor fluid samples, respectively, was implemented and employed mobile phases A (0.05 mL trifluoroacetic acid (TFA) in 1000 mL LC-MS grade water) and B (0.05 mL TFA in 1000 mL LC-MS grade acetonitrile). The lower level of quantification (LLOQ) for the compound of Formula I for the LC-MS/MS method was determined to be in the 6-10 ng/mL range.

Figure 5:
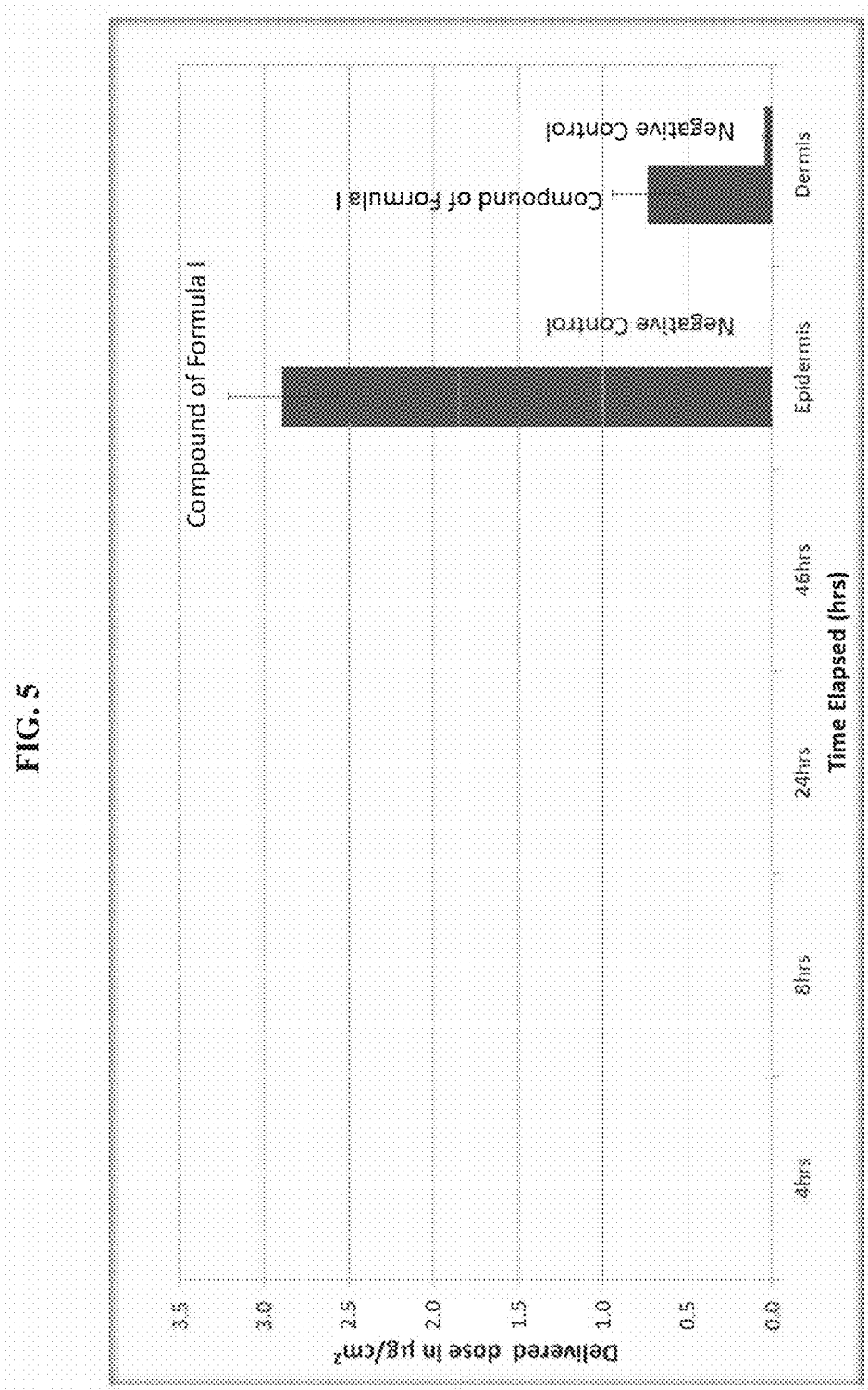
FIG. 5 shows epidermal, dermal, and receptor fluid levels of the compound of Formula I 46 hours after topical application to the epidermis of a 2% compound of Formula I cream. Results were obtained from 6 replicates of an in vitro skin penetration study using human cadaver skin samples mounted in Franz Diffusion Cells; receptor fluid was in contact with the dermis.

The accumulated amount of compound of Formula I in the epidermis and dermis and at each of the time points in the receptor fluid are shown in FIG. 5. A negative control using vehicle cream is also shown. The compound of Formula I was only detected in the epidermis, at 2.89+/−0.32 µg/cm$^2$, and dermis, at 0.73+/−0.21 µg/cm$^2$, but not in the transdermal receptor fluid. With the compound of Formula I being lipophilic with low aqueous solubility (the solubility limit of the compound of Formula I in the receptor fluid was determined to be approximately 35.8 µg/mL, sufficient to maintain sink conditions throughout the experiment), the data very clearly demonstrate the much preferred partitioning of the compound of Formula I into lipid containing compartments, such as tissues, over hydrophilic compartments, such as the receptor fluid. This characteristic most likely translates to lipid containing compartments in the eyelid in general, such as Meibomian glands, meibum, and other fatty structures turning them into drug depot and "extended release" delivery mechanisms (via meibum) to the ocular surface for lipophilic compounds administered peri-ocularly.

Example 4: Ocular and Systemic Exposure Following Peri-Ocular Cream Administration To determine the maximal tolerated dose amount first, two Hanford minipigs were dosed twice-daily (BID) approximately 6 hours apart topically with a cream (comprised of 2% w/w compound of Formula I, 46% w/w white petrolatum, 8% w/w mineral oil, 8% w/w propylene glycol, 6.6% w/w ST-cyclomethicone-SNF, 3.3% w/w emulsifier 10, 2% w/w ST-elastomer-10, 0.08% w/w methylparaben, 0.06% w/w sodium phosphate dibasic anhydrous, 0.05% w/w citric acid anhydrous, 0.02% w/w propylparaben, and q.s. purified water) to the upper and lower eyelids of one eye, with ascending doses (25, 50, 75, 100 µL) over 4 days to determine ocular and dermal tolerability and the maximal feasible amount of the cream formulation on each eyelid. Study variables assessed were mortality, clinical observations of illness or reaction to treatment, ocular observations using a modified Hackett McDonald grading system, and dermal Draize scoring. The cream was generally well tolerated at all four doses administered BID. A dose amount of 75 µL per eyelid was determined to be the maximal feasible dose amount, because of ease of application and minimal risk of cream transfer to the ocular surface, which covered the entire minipig eyelid with a thin layer of the test article formulation with no dripping, flowing or running down of the formulation onto the ocular surface. The dose amount of 75 µL was then used for subsequent studies.

To determine the ocular exposure and pharmacokinetics following topical cream administration to the eyelids, the cream containing 2% of compound of Formula I was applied BID to eyelids of 8 Hanford minipigs for 7 days and one additional application on day 8 for a total of 15 topical doses. After the last dose on day 8, two animals each were euthanized at 2, 4, 8, and 24 hours after the final dose, and eyes were collected for dissection into the following tissues and fluids: eyelids (including palpebral conjunctiva), bulbar conjunctiva, cornea, iris/ciliary body (ICB), and aqueous humor (AQH). Plasma was also collected (prior to dose application on Days 1 and 8, and prior to euthanasia). A decision was made not to attempt to collect meibum, since the amounts expressable from the lid margin were found to be minimal and the procedure of meibum expression through manipulation/rubbing/squeezing of the eyelids would have rendered the eyelid tissues compromised and unusable for further analysis. Meibum was believed to be only one lipid compartment in the eyelids that could act as a depot for lipophilic compounds. Meibomian glands and other fatty tissues were others. Attempts to express meibum from the ducts, thereby rendering the eyelid itself unusable for further analysis, would have not permitted assessment of drug content in other potential lipid structures in the eyelids. Thus, the decision was made to assess drug exposure in the eyelid as an intact tissue to capture all potential drug depots.

Three different extraction and analytical methods were developed for the determination of the compound of Formula I in i) plasma and aqueous humor; ii) bulbar conjunctiva, cornea, ICB; iii) eyelids. Assay ranges were 0.1-100 ng/mL, 1-1000 ng/g, and 1-1000 ng/g, respectively. Briefly, analytical methods were as follows: i) plasma and aqueous humor standards were from minipig and rabbit, respectively; ii) bulbar conjunctiva, cornea, ICB standard was rabbit cornea; iii) eyelid standard was pig skin. The internal standard working solution for analytical purposes was comprised of 20.0 ng/mL $^{13}C_2$, $^{15}N$-labeled compound of Formula I in acetonitrile with 1% formic acid (v/v) which was being added to each sample. The tissue/fluid sample extraction procedure involved i) plasma/aqueous humor sample; ii) bulbar conjunctiva, cornea, ICB homogenization in acetonitrile; iii) eyelid digestion in 1:1 acetonitrile:ammonium hydroxide solution for 1.5 hours at 37° C. followed by acetonitrile addition, homogenization, and neutralization with formic acid; in all cases followed by addition of internal standard working solution, vortexing and centrifugation. Analysis of the samples was then carried out with LC-MS/MS, employing mobile phases A (Water with 0.1% formic acid) and B (acetonitrile with 0.1% formic acid).

Figure 6:
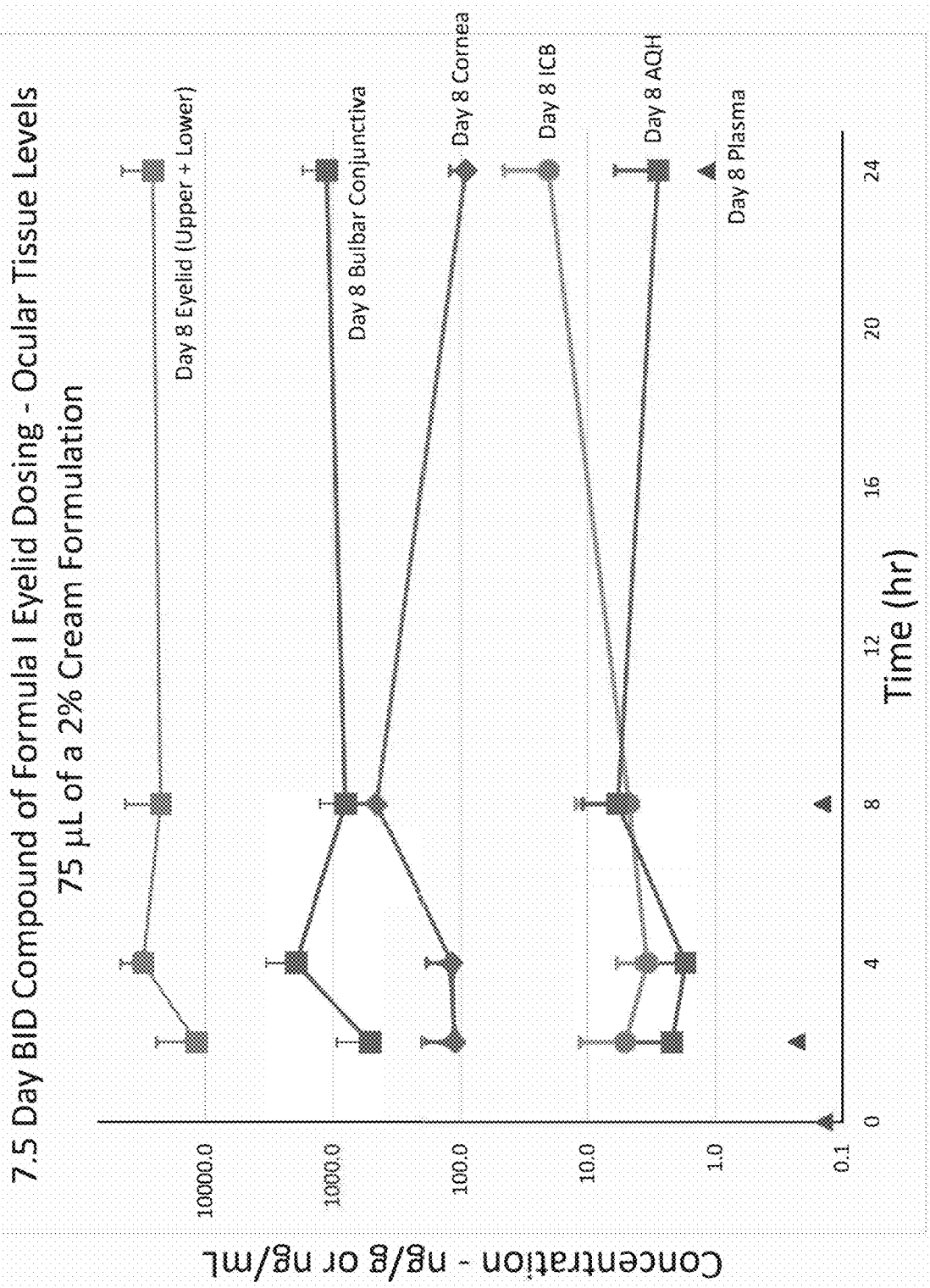
FIG. 6 shows ocular exposure levels in minipig eyes following twice-daily eyelid administration of a 2% compound of Formula I cream over 7.5 days. Time points are 2, 4, 8, and 24 hours after the final dose on day 8.

After 15 topical applications over 7.5 days, the highest ocular exposure levels of the compound of Formula I after the final application were detected in eyelid tissue (highest mean concentration of 30613 ng/g at 4 hours post final dose), followed by bulbar conjunctiva (mean of 1931 ng/g at 4 hours post final dose), cornea (mean of 452 ng/g at 8 hours post final dose), ICB (mean of 20.48 ng/g at 24 hours post final dose), and aqueous humor (mean of 5.81 ng/g at 8 hours post final dose) (FIG. 6). In all tissues, these concentration ranges represent pharmacologically active concentrations of the compound of Formula I even when taking high protein binding of approximately 99% into account resulting in "free" drug concentrations that are approximately $1/100^{th}$ of the total measured concentration. Unexpectedly, in each compartment the exposure levels remained almost constant for up to 24 hours post final pen-ocular dose application. This exposure profile is very different from that of a typical eyedrop application and highly suggestive of a drug depot in the eyelids that "feeds" the downstream compartments (conjunctiva, cornea, ICB, aqueous humor) over at least a 24-hour period. Since lipophilic compounds preferentially partition into lipid compartments and not into aqueous, hydrophilic compartments as evidenced for the compound of Formula I by the aforementioned skin permeation study it can be concluded that the lipid structures of the eyelid (e.g., meibomian glands, meibum, other fatty tissues) serve as drug depots for peri-ocularly delivered drugs with the meibum becoming a drug delivery vehicle since it is constantly produced by the meibomian glands and secreted onto the corneal surface. These conclusions are related to, and consistent with, the lipophilic properties of the compound of Formula I and, as such, are expected to generally translate to all other lipophilic compounds similarly if not equally.

Furthermore, this 24-hour exposure profile following peri-ocular administration of a lipophilic compound, such as the compound of Formula I, translates to a once-daily application regimen representing a major benefit for patients who are often required to administer steroid or other eyedrops up to 4 to 6 or more times each day. A once-daily application regimen provides for improved safety and convenience for patients over eyedrops that have to be administered more frequently.

A further significant benefit of peri-ocular application is the larger dosing volume which allows much greater flexibility with respect to delivery of a wide range of drug doses compared to eyedrop application, making it possible that many more drugs may be applied once-daily than with eyedrops, translating to the aforementioned patient benefit. The volume of eyedrops is typically limited to approximately a 30 µL volume, or up to approximately a 40 µL volume in some cases, per administration per eye. A 75 µL peri-ocular dosing volume for each eyelid, or 150 µL per eye, equates to at least a 4-fold greater dose volume per administration.

Yet a further benefit of peri-ocular application, aside from the larger dosing volume as described above, is that a greater percentage of drug is available for delivery to the target tissues at the ocular surface. Eyedrop application is particularly known for delivering only a small fraction of the API that is applied as part of the eyedrop formulation. The reason is that an eyedrop applied to the ocular surface rapidly drains away from the ocular surface via the nasolacrimal duct and is thus understood to deliver only about up to 1% of its API "payload" contained in the delivered eyedrop to the ocular surface tissues (cornea and conjunctiva). In contrast, peri-ocular administration delivers essentially 100% or close to 100% of the API contained in the peri-ocular formulation to the eyelid tissue. Taken together with the larger delivery volume of a peri-ocularly applied formulation compared to a topically applied eyedrop, the pen-ocular route represents an enormous dosing advantage of API to ocular surface tissues over the topical eyedrop route.

Plasma exposure to the compound of Formula I in this study (for up to 24 hours after the last pen-ocular application) was variable but generally low or below the lower limit of quantification of 0.1 ng/mL (FIG. 6). The highest plasma concentration, 2.22 ng/mL, was observed 24 hours following the final Day 8 dose. The results indicated that there was no or very low systemic accumulation after 7.5 days of multiple topical eyelid application.

Plasma exposure was also determined in another 7-day study in minipigs. The compound of Formula I was formulated in a cream at 4% w/w and 6% w/w additionally comprised of 44% w/w or 42% w/w White Petrolatum, respectively, and 8% w/w mineral oil, 8% w/w propylene glycol, 6.6% w/w ST-cyclomethicone-SNF, 3.3% w/w emulsifier 10, 2% w/w ST-elastomer-10, 0.08% w/w methylparaben, 0.06% w/w sodium phosphate dibasic anhydrous, 0.05% w/w citric acid anhydrous, 0.02% w/w propylparaben, and q.s. purified water. The cream formulation was applied peri-ocularly at a dose volume of 75 µL per eyelid to the upper and lower eyelids of the right eye of 3 minipigs for each concentration 3 times daily (TID) at an 8-hour interval for 6 days and once in the morning on day 7. Plasmas levels of the compound of Formula I were then assessed for up to 7 days post final dosing.

Dermal administration of 4% (18 mg/eye/day) and 6% (27 mg/eye/day) compound of Formula I cream to the upper and lower eyelids of one eye of Hanford minipigs was well tolerated. There were no test article-related effects on body weights, clinical observations, tonometry (intraocular pressure), hematology, or serum chemistry.

In female minipigs receiving multiple doses of compound of Formula I cream at 18 mg/eye/day and 27 mg/eye/day, plasma TK parameters ($C_{max}$, $T_{max}$, $AUC_{last}$, $AUC_{0-24}$) for the compound of Formula I were low and variable. Plasma concentrations persisted for at least 2 to 7 days after the last administered dose.

This is an intriguing and unexpected finding as the data suggest that the ocular drug depot (established following peri-ocular cream application for 7 days) released drug over an extended period of time such that, in some animals, systemic levels of the compound of Formula I could be measured for up to 7 days after the final pen-ocular cream application. Conceptually, these finding are entirely consistent with extended delivery from a Meibomian gland/meibum drug depot to the systemic circulation and, presumably, ocular surface.

Example 5: Manufacturing Process

Figure 7:
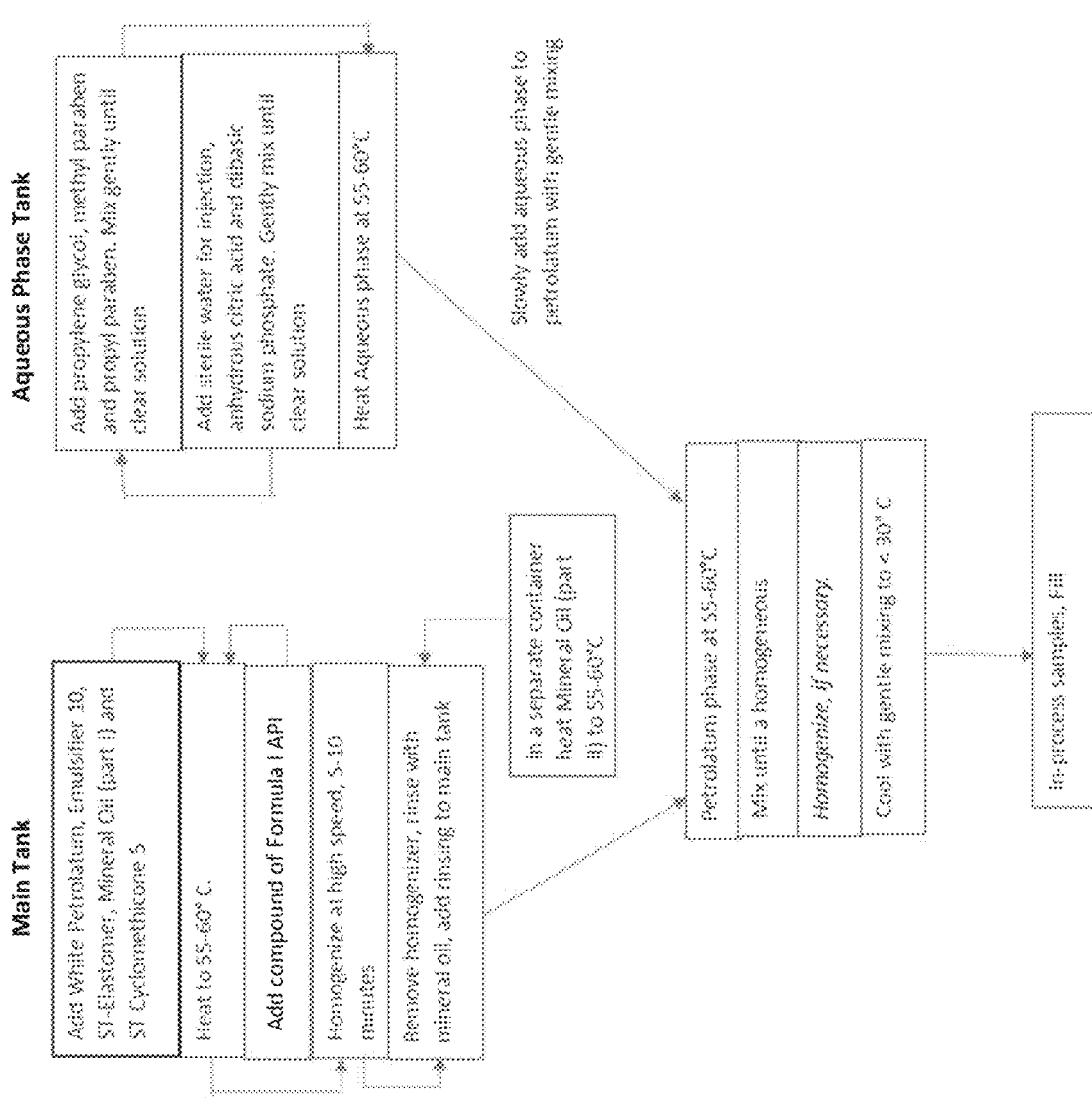
FIG. 7 process flow chart for manufacturing of a cream comprising the compound of Formula I.

Peri-ocular application requires a sterile manufacturing process for ophthalmic drug products, regardless of the presence or absence of preservatives in the formulation. The manufacturing process, as outlined in FIG. 7, is based on the combination under aseptic conditions of hydrophilic and lipophilic components, each presterilized separately by an appropriate sterilization process, such as filtration, heat, gamma or beta or alpha irradiation, or otherwise. The presterilized API (heat, gamma or beta or alpha irradiation, or otherwise) is incorporated into the presterilized lipophilic component at an appropriate temperature using an appropriate mixing process. Then, this lipophilic component is mixed with the presterilized hydrophilic component at an appropriate temperature using an appropriate process, such as stirring, shaking, vortexing, sonication, etc. at a predetermined mixing rate. The final mixture is then allowed to cool to an appropriate temperature necessary for the filling process into appropriate containers for the final drug product, whether for clinical or commercial use.

As one embodiment, the manufacturing process of a cream comprising the compound of Formula I, as described in this application and in FIG. 7, requires a high-speed homogenization procedure to incorporate the API and a gentle mixing/stirring procedure for combining the lipophilic and hydrophilic components. In the same embodiment, the lipophilic component is heated to 55-60° C. for the incorporation of the API, such as the compound of Formula I, and the mixing process with the hydrophilic component. The final product is then slowly cooled to under 30° C. prior to filling into the final containers for a clinical study or commercial use.

In other embodiments, the lipophilic component is heated to a temperature necessary to liquefy this component to make it suitable to a sterilization procedure by filtration, or not heated at all. This includes temperature ranges of 1-10° C., 10-20° C., 20-30° C., 30-40° C., 40-50° C., 50-60° C., 60-70° C., 70-80° C., 80-90° C., 90-100° C., 100-110° C., 110-120° C., 120-130° C., 130-140° C., 140-150° C., 150-160° C., and 160-170° C.

In other embodiments, incorporation of the API requires a slow, high, or intermediate mixing speed at a specific temperature within a range of 1-10° C., 10-20° C., 20-30° C., 30-40° C., 40-50° C., 50-60° C., 60-70° C., 70-80° C., 80-90° C., 90-100° C., 100-110° C., 110-120° C., 120-130° C., 130-140° C., 140-150° C., 150-160° C., and 160-170° C. This process includes mixing, shaking, stirring, vortexing, sonication, etc.

In other embodiments, mixing of the hydrophilic and lipophilic components is achieved at room temperature or temperature ranges of 1-10° C., 10-20° C., 20-30° C., 30-40° C., 40-50° C., 50-60° C., 60-70° C., 70-80° C., 80-90° C., 90-100° C., 100-110° C., 110-120° C., 120-130° C., 130-140° C., 140-150° C., 150-160° C., and 160-170° C.

In other embodiments, the final product is then slowly or rapidly cooled to a temperature necessary for the filling into the final containers for a clinical study or commercial use. This cooling process requires mixing at a slow, rapid or intermediate speed, or no mixing at all.

What is claimed is:

1. A method of providing palliative or therapeutic relief of an ocular disease in a subject, comprising administering to the subject a pharmaceutical composition comprising:
   a) a therapeutically effective amount of a compound of Formula I, and wherein the compound of Formula I is of the structure:

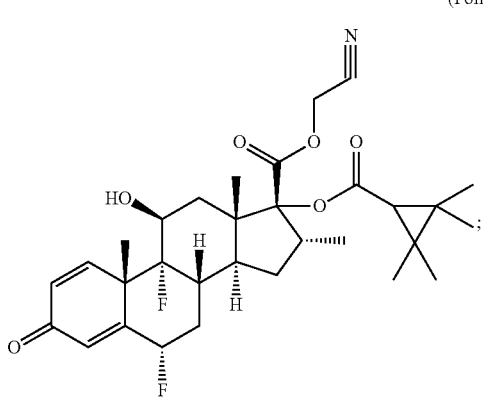

(Formula I)

and
   b) a pharmaceutically acceptable carrier adapted for peri-ocular transdermal delivery of the compound of Formula I to one or more peri-orbital glands of a subject;
   wherein the ocular disease is dry eye disease, meibomitis, loss of homeostasis of the tear film, tear film instability and hyperosmolarity, ocular surface inflammation and damage, Meibomian gland dysfunction, posterior blepharitis, anterior blepharitis, or any combination thereof.

2. The method of claim 1, wherein the pharmaceutical composition is topically administered to the external portion of an upper and/or lower eyelid of the subject.

3. The method of claim 1, wherein the compound of Formula I is delivered to the ocular surface of the subject via the Meibomian gland.

4. The method of claim 1, wherein the one or more peri-orbital glands are selected from the group consisting of a Meibomian gland, a lacrimal gland, an accessory lacrimal gland, and any combinations thereof.

5. The method of claim 1, wherein the pharmaceutical composition comprises the compound of Formula I at a concentration between 0.001% and 10% weight per weight (w/w).

6. The method of claim 1, wherein the pharmaceutical composition comprises the compound of Formula I at a concentration between 0.01% and 1% weight per weight (w/w).

7. The method of claim 1, wherein the pharmaceutical composition comprises the compound of Formula I at a concentration between 0.01% and 0.5% weight per weight (w/w).

8. The method of claim 1, wherein the pharmaceutical composition comprises the compound of Formula I at a concentration of 0.001%, 0.005%, 0.01%, 0.05%, 0.1%, 0.2%, 0.3%, 0.4%, 0.5%, 0.6%, 0.7%, 0.8%, 0.9%, 1%, 1.25%, 1.5%, 1.75%, 2%, 2.25%, 2.5%, 2.75%, 3%, 3.5%, 4%, 4.5%, 5%, 5.5%, 6%, 6.5%, 7%, 7.5%, 8%, 8.5%, 9%, 9.5%, or 10% w/w.

9. The method of claim 1, wherein the pharmaceutical composition comprises the compound of Formula I at a concentration of about 0.2% w/w.

10. The method of claim 1, wherein the pharmaceutically acceptable carrier is selected from the group consisting of an ointment, cream, lotion, gel, emulsion, suspension, oil, foam, transdermal patch, spray, or any combination thereof.

11. The method of claim 10, wherein the pharmaceutically acceptable carrier is a cream.

12. The method of claim 11, wherein the cream comprises an oil-in-water base or a water-in-oil base.

13. The method of claim 11, wherein the cream comprises white petrolatum, mineral oil, propylene glycol, ST-cyclomethicone-5NF, emulsifier 10, ST-elastomer-10, sodium phosphate dibasic anhydrous, citric acid, and purified water.

14. The method of claim 11, wherein:
   the cream comprises 48% w/w white soft paraffin, 8% w/w mineral oil, 8% w/w propylene glycol, 6.6% w/w ST-cyclomethicone-5NF, 3.3% w/w ST-emulsifier, 2% w/w ST-elastomer-10, 0.08% w/w methylparaben, 0.06% w/w dibasic sodium phosphate, 0.05% w/w citric acid, 0.02% w/w propylparaben, and purified water; or
   the cream comprises 48% w/w white soft paraffin, 8% w/w mineral oil, 8% w/w propylene glycol, 6.6% w/w cyclomethicone, 3.3% w/w emulsifier 10, 2% w/w ST-elastomer-10, 0.08% w/w methylparaben, 0.06% w/w sodium phosphate dibasic anhydrous, 0.046% w/w citric acid anhydrous, 0.02% w/w propylparaben, and purified water; or
   the cream comprises 48% w/w white petrolatum, 8% w/w mineral oil, 8% w/w propylene glycol, 6.6% w/w ST-cyclomethicone-5NF, 3.3% w/w emulsifier 10, 2% w/w ST-elastomer-10, 0.06% w/w sodium phosphate dibasic anhydrous, 0.05% w/w citric acid anhydrous, 0.02% w/w benzalkonium chloride, and purified water.

15. The method of claim 11, wherein the cream comprises the compound of Formula I at a concentration of about 0.2% w/w, about 48% w/w white petrolatum, about 8% w/w mineral oil, about 8% w/w propylene glycol, about 6.6% w/w ST-cyclomethicone-5NF, about 3.3% w/w emulsifier 10, about 2% w/w ST-elastomer-10, about 0.06% w/w sodium phosphate dibasic anhydrous, about 0.05% w/w citric acid anhydrous, and purified water.

16. The method of claim 10, wherein the pharmaceutically acceptable carrier is an ointment.

17. The method of claim 16, wherein the ointment comprises 61.5% w/w white soft paraffin, 8% w/w mineral oil, 8% w/w propylene glycol, 5% w/w of St. cyclomethicone-5NF, 5% w/w of labrasol, 5% w/w of propylene carbonate, 2.5% w/w of steareth 2, 2.5% w/w of St. emulsifier 10, and 2.5% w/w of St. elastomer-10.

18. The method of claim 11, wherein the cream is preservative-free.

19. The method of claim 18, wherein the cream that is preservative-free comprises:
   white soft paraffin/petrolatum, mineral oil, propylene glycol, ST-cyclomethicone-5NF, emulsifier-10, ST-elastomer-10, dibasic sodium phosphate, citric acid, and purified water; and/or
   48% w/w white petrolatum, 8% w/w mineral oil, 8% w/w propylene glycol, 6.6% w/w ST-cyclomethicone-5NF, 3.3% w/w emulsifier 10, 2% w/w ST-elastomer-10, 0.06% w/w sodium phosphate dibasic anhydrous, 0.05% w/w citric acid anhydrous, and purified water.

20. The method of claim 11, wherein the cream further comprises benzalkonium chloride (BAK), or propylparaben and methylparaben.

21. The method of claim 1, wherein the pharmaceutical composition is administered one time each day that it is administered.

22. The method of claim 1, wherein the pharmaceutical composition is administered for one day, two days, three days, four days, five days, six days, one week, two weeks, three weeks, four weeks, five weeks, six weeks, seven weeks, eight weeks, nine weeks, 10 weeks, 11 weeks, 12 weeks, 24 weeks, 36 weeks, or 48 weeks or more.

23. The method of claim 1, wherein the subject is a human or a non-human animal.

24. The method of claim 23, wherein the subject is a human.

* * * * *